US00RE43876E

(19) United States
(12) Reissued Patent
Rezania

(10) Patent Number: US RE43,876 E
(45) Date of Reissued Patent: Dec. 25, 2012

(54) CELLS EXPRESSING PLURIPOTENCY MARKERS AND EXPRESSING MARKERS CHARACTERISTIC OF THE DEFINITIVE ENDODERM

(75) Inventor: Alireza Rezania, Belle Mead, NJ (US)

(73) Assignee: Centocor Ortho Biotech Inc., Horsham, PA (US)

(21) Appl. No.: 13/372,641

(22) Filed: Feb. 14, 2012

Related U.S. Patent Documents

Reissue of:
(64) Patent No.: 7,939,322
Issued: May 10, 2011
Appl. No.: 12/108,872
Filed: Apr. 24, 2008

(51) Int. Cl.
*C12N 5/02* (2006.01)
*C12N 5/04* (2006.01)

(52) U.S. Cl. ..... 435/377; 435/375; 435/384

(58) Field of Classification Search ..... None
See application file for complete search history.

(56) References Cited

U.S. PATENT DOCUMENTS

| | | | |
|---|---|---|---|
| 5,834,308 | A | 11/1998 | Peck et al. |
| 5,843,780 | A | 12/1998 | Thomson |
| 6,200,806 | B1 | 3/2001 | Thomson |
| 6,458,589 | B1 | 10/2002 | Rambhatla et al. |
| 6,458,593 | B1 | 10/2002 | Musick et al. |
| 6,642,048 | B2 | 11/2003 | Xu et al. |
| 6,800,480 | B1 | 10/2004 | Bodnar et al. |
| 2002/0072117 | A1 | 6/2002 | Xu et al. |
| 2003/0082155 | A1 | 5/2003 | Habener et al. |
| 2003/0138948 | A1 | 7/2003 | Fisk et al. |
| 2004/0015805 | A1 | 1/2004 | Kidd et al. |
| 2004/0241761 | A1 | 12/2004 | Sarvetnick et al. |
| 2005/0037488 | A1 | 2/2005 | Mitalipova et al. |
| 2005/0148070 | A1 | 7/2005 | Thomson |
| 2005/0158853 | A1 | 7/2005 | D'Amour et al. |
| 2005/0233446 | A1 | 10/2005 | Parsons et al. |
| 2005/0244962 | A1 | 11/2005 | Thomson |
| 2005/0266554 | A1 | 12/2005 | D'Amour et al. |
| 2006/0003446 | A1 | 1/2006 | Keller et al. |
| 2006/0040387 | A1 | 2/2006 | Fisk et al. |
| 2007/0010011 | A1 | 1/2007 | Parsons et al. |
| 2007/0259423 | A1 | 11/2007 | Odorico et al. |
| 2009/0325293 | A1 | 12/2009 | Davis et al. |

FOREIGN PATENT DOCUMENTS

| | | | |
|---|---|---|---|
| EP | 1873237 | A1 | 1/2008 |
| WO | WO 99/20741 | A1 | 4/1999 |
| WO | WO 00/29549 | A | 5/2000 |
| WO | WO 01/51616 | A2 | 7/2001 |
| WO | WO 01/81549 | A2 | 11/2001 |
| WO | WO 01/81549 | A3 | 11/2001 |
| WO | WO 03/102134 | A2 | 12/2003 |
| WO | WO 2004/011621 | A2 | 2/2004 |
| WO | WO 2004/090110 | A2 | 10/2004 |
| WO | WO 2005/014799 | A1 | 2/2005 |
| WO | WO 2005/065354 | A2 | 7/2005 |
| WO | WO 2005/086845 | A2 | 9/2005 |
| WO | WO 2005/116073 | A2 | 12/2005 |
| WO | WO 2005/116073 | A3 | 12/2005 |
| WO | WO 2006/016999 | A | 2/2006 |
| WO | WO 2006/020919 | A3 | 2/2006 |
| WO | WO 2006/094286 | A2 | 9/2006 |
| WO | WO 2007/030870 | A1 | 3/2007 |
| WO | WO 2007027157 | A1 | 3/2007 |
| WO | WO 2007/082963 | A | 7/2007 |
| WO | WO 2007/103282 | A | 9/2007 |
| WO | WO 2007/139929 | A2 | 12/2007 |
| WO | WO 2007/139929 | A3 | 12/2007 |
| WO | WO 2009/012428 | A2 | 1/2009 |

OTHER PUBLICATIONS

Morrison Sean J. et al.: "Culture in reduced levels of oxygen promotes clonogenic sympathoadrenal differentiation by isolated neural crest stem cells" Journal ofNeuroscient, vol. 20, No. 19, Oct. 1, 2000 XP002552625.
Shinozaki et al., Development 131, 1651-1662 (2004).
Wiles et al. (Exp Cell Res. Feb. 25, 1999; 247(1):241-8).
Amit et al (Biol. Reprod 68: 2150-2156, 2003).
Ausubel et al.Current Protocols in Molecular Biology, eds. 2001 supplement.
Benvenistry et al. (Benvenistry et al, Stem Cells 2006; 24:1923-1930).
Blyszczuk et al. (PNAS 100:998, 2003).
Cheon et al BioReprod 77 2007.
Ricordi et al Diabetes 37:413-420 (1988).
D'Amour et al, Nature Biotechnology 24, 1392-1401 (2006).
D'Amour et al, Nature Biotechnology 23, 1534-1541 (2005).
Gordon et al. (PNAS 103: 16806, 2006).
Harlow and Lane, Using Antibodies: A Laboratory Manual, New York: Cold Spring Harbor Laboratory Press (1998).
Hori et al. (PNAS 99: 16105, 2002).
Inzunza et al (Stem Cells 23: 544-549, 2005).
Lee, J.B. et al.: "Establishment and Maintenance of Human Embryonic Stem Cell Lines on Human Feeder Cells Derived from Uterine Endometricum under Serum-Free Condition" Biology of Reproduction, Society for the Study of Reproduction, Campaign, IL, US vol. 72, Jan. 1, 2005 pp. 42-49 XP008083585.
Levenstein et al (Stem Cells 24: 568-574, 2006).
Kroon Evert et al.: "Pancreatic Endoderm Derived from Human Embryonic Stem Cells Generates Glucose-Responsive Insulin-Secreting Cells in Vivo" Nature Biotechnology Apr. 2008, vol. 26, No. 4, Apr. 1, 2008 pp. 443-452, XP002561975.
Shiraki N. et al.: "Guided Differentiation of Embryonic Stem Cells into Pdxl—Expressing Regional—Specific Definitive Endoderm" Stem Cells, Alphamed Press, Dayton, OH US vol. 26, No. 4 Apr. 1, 2008, pp. 874-885, XP002547894.
Ludwig, TE. et al., "Derivation ofHuman Embryonic Stem Cells in Defined Conditions" Nature Biotechnology vol. 24, No. 2, Feb. 2006 pp. 185-187, XP002564246.
Yasuda Emiko et al.: "Development ofCystic Embryoid Bodies with Visceral Yolk-Sac-Like Structures from Mouse Embryonic Stem Cells Using Low-Adherence 96-Well Plate." Journal of Bioscience and Bioengineering, Apr. 4, 2009, vol. 107, o.4, pp. 442-446, XP002564247.
McLean et al, Stem Cells 25, 29-38 (2007).

(Continued)

*Primary Examiner* — Deborah Crouch
(74) *Attorney, Agent, or Firm* — Mark R. Warfield

(57) ABSTRACT

The present invention is directed to pluripotent cells that can be readily expanded in culture on tissue culture substrate that is not pre-treated with protein or an extracellular matrix, and do not require a feeder cell line. The present invention also provides methods to derive the pluripotent cell line from human embryonic stem cells.

16 Claims, 49 Drawing Sheets

OTHER PUBLICATIONS
Micallef et al. (Diabetes 54:301, 2005).
Miyamoto et al (Stem Cells 22: 433-440, 2004).
Richards et al, (Stem Cells 21: 546-556, 2003).
Reubinoff et al (Nature Biotechnology 18: 399-404 (2000).
Shamblott et al., Proc. Natl. Acad. Sci. USA 95:13726, 1998.
Kubo et al, Development 131, 1651-1662 (2004).
Shiraki et al. Genes Cells. Jun. 2005; 10(6): 503-16.
Skoudy et al. (Biochem. J. 379: 749, 2004).
Stojkovic et al (Stem Cells 2005 23: 306-314, 2005).
Thompson et al (Science Nov. 6, 1998: vol. 282. No. 5391, pp. 1145-1147).
Wang et al (Stem Cells 23: 1221-1227, 2005).
Xu et al (Stem Cells 22: 972-980, 2004).
Gershengorn et al Science 306: 2261-2264, 2004.
Seaberg et al Nature Biotechnology 22: 1115-1124, 2004.
Bonner Wier et al Proc Nat Acad Sci 97: 7999-8004, 2000.
Curr. Top. Dev. Biol. 38:133 ff., 1998.
Thomson et al Proc. Natl. Acad. Sci. U.S.A. 92:7844, 1995.
Lumelsky et al. (Science 292:1389, 2001).
Soria et al. (Diabetes 49:157, 2000).
Miyazaki et al. (Diabetes 53: 1030, 2004).
Kleinman, H.K., et al., Biochemistry 25:312 (1986).
Hadley, M.A., et al., J.Cell.Biol. 101:1511 (1985).
Tulachan et al (Developmental Biology, 305, 2007, pp. 508-521).
Ezashi T et al.: "Low 02 tensions and the prevention of differentiation ofhES cells" Proceedings ofthe National Academy of Sciences of USA, National Academy of Science, Washington, DC, US, vol. 102, No. 13, Mar. 29, 2005 pp. 4783-4788 XP002466326.
Koller M.R. et al.: "Effects of Synergistic Cytokine Combinations, low oxygen, and irradiated stroma on the expansion of human cord blood progenitors" Blood, American Society of Hematology, US, vol. 80, No. 2, Jul. 15, 1992, pp. 403-411 XP000604784.
Thompson et al (Science Nov. 6, 1998: vol. 282, No. 5391, pp. 1145-1147).

b) Day 11- 2% FBS + AA + Wnt3A a) Day 11- 2% FBS + AA c) Passage 3 in 2% FBS + AA + WNT-3A Proliferation of EXPRES cells a)

b)

i) DAPI j) CDX-2 10X k)

l)

m)

A)
B)
C)
D)
E)
F)
Anti-BRDU APC
7AAD
P2
P3
P4
P5
P6
(x 1,000)
Frequency %
S
G1
G2/M
AA+Wnt
AA+Wnt+IgF
H9p43
AFDX002
MEF

CXCR4

A) i)

ii)

B) i)

ii)

b)

a)

b)

CELLS EXPRESSING PLURIPOTENCY MARKERS AND EXPRESSING MARKERS CHARACTERISTIC OF THE DEFINITIVE ENDODERM

Matter enclosed in heavy brackets [ ] appears in the original patent but forms no part of this reissue specification; matter printed in italics indicates the additions made by reissue.

FIELD OF THE INVENTION

The present invention is directed to pluripotent stem cells that can be readily expanded in culture on tissue culture polystyrene and do not require a feeder cell line. The present invention also provides methods to derive the pluripotent stem cell line from human embryonic stem cells.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, for example, thyroid, thymus, pancreas, gut, and liver, will develop from the endoderm, via an intermediate stage. The intermediate stage in this process is the formation of definitive endoderm. Definitive endoderm cells express a number of markers, such as, HNF-3 beta, GATA-4, Mixl1, CXCR4 and SOX-17.

Formation of the pancreas arises from the differentiation of definitive endoderm into pancreatic endoderm. Cells of the pancreatic endoderm express the pancreatic-duodenal homeobox gene, PDX-1. In the absence of PDX-1, the pancreas fails to develop beyond the formation of ventral and dorsal buds. Thus, PDX-1 expression marks a critical step in pancreatic organogenesis. The mature pancreas contains, among other cell types, exocrine tissue and endocrine tissue. Exocrine and endocrine tissues arise from the differentiation of pancreatic endoderm.

Cells bearing the features of islet cells have reportedly been derived from embryonic cells of the mouse. For example, Lumelsky et al. (Science 292:1389, 2001) report differentiation of mouse embryonic stem cells to insulin-secreting structures similar to pancreatic islets. Soria et al. (Diabetes 49:157, 2000) report that insulin-secreting cells derived from mouse embryonic stem cells normalize glycemia in streptozotocin-induced diabetic mice.

In one example, Hori et al. (PNAS 99: 16105, 2002) disclose that treatment of mouse embryonic stem cells with inhibitors of phosphoinositide 3-kinase (LY294002) produced cells that resembled β cells.

In another example, Blyszczuk et al. (PNAS 100:998, 2003) reports the generation of insulin-producing cells from mouse embryonic stem cells constitutively expressing Pax4.

Micallef et al. reports that retinoic acid can regulate the commitment of embryonic stem cells to form PDX-1 positive pancreatic endoderm. Retinoic acid is most effective at inducing PDX-1 expression when added to cultures at day 4 of embryonic stem cell differentiation during a period corresponding to the end of gastrulation in the embryo (Diabetes 54:301, 2005).

Miyazaki et al. reports a mouse embryonic stem cell line over-expressing PDX-1. Their results show that exogenous PDX-1 expression clearly enhanced the expression of insulin, somatostatin, glucokinase, neurogenin3, P48, Pax6, and HNF6 genes in the resulting differentiated cells (Diabetes 53: 1030, 2004).

Skoudy et al. reports that activin-A (a member of the TGFβ superfamily) upregulates the expression of exocrine pancreatic genes (p48 and amylase) and endocrine genes (PDX-1, insulin, and glucagon) in mouse embryonic stem cells. The maximal effect was observed using 1 nM activin-A. They also observed that the expression level of insulin and PDX-1 mRNA was not affected by retinoic acid; however, 3 nM FGF-7 treatment resulted in an increased level of the transcript for PDX-1 (Biochem. J. 379: 749, 2004).

Shiraki et al. studied the effects of growth factors that specifically enhance differentiation of embryonic stem cells into PDX-1 positive cells. They observed that TGFβ2 reproducibly yielded a higher proportion of PDX-1 positive cells (Genes Cells. 2005 June; 10(6): 503-16.).

Gordon et al. demonstrated the induction of brachyury+/HNF-3 beta+endoderm cells from mouse embryonic stem cells in the absence of serum and in the presence of activin along with an inhibitor of Wnt signaling (US2006/0003446A1).

Gordon et al. (PNAS, Vol 103, page 16806, 2006) states "Wnt and TGF-beta/nodal/activin signaling simultaneously were required for the generation of the anterior primitive streak".

However, the mouse model of embryonic stem cell development may not exactly mimic the developmental program in higher mammals, such as, for example, humans.

Thomson et al. isolated embryonic stem cells from human blastocysts (Science 282:114, 1998). Concurrently, Gearhart and coworkers derived human embryonic germ (hEG) cell lines from fetal gonadal tissue (Shamblott et al., Proc. Natl. Acad. Sci. USA 95:13726, 1998). Unlike mouse embryonic stem cells, which can be prevented from differentiating simply by culturing with Leukemia Inhibitory Factor (LIF), human embryonic stem cells must be maintained under very special conditions (U.S. Pat. No. 6,200,806; WO 99/20741; WO 01/51616).

D'Amour et al. describes the production of enriched cultures of human embryonic stem cell-derived definitive endoderm in the presence of a high concentration of activin and low serum (D'Amour K A et al. 2005). Transplanting these cells under the kidney capsule of mice resulted in differentiation into more mature cells with characteristics of some endodermal organs. Human embryonic stem cell-derived definitive endoderm cells can be further differentiated into PDX-1 positive cells after addition of FGF-10 (US 2005/0266554A1).

D'Amour et al. (Nature Biotechnology—24, 1392-1401 (2006)) states "We have developed a differentiation process that converts human embryonic stem (hES) cells to endocrine cells capable of synthesizing the pancreatic hormones insulin, glucagon, somatostatin, pancreatic polypeptide and ghrelin. This process mimics in vivo pancreatic organogenesis by directing cells through stages resembling definitive endoderm, gut-tube endoderm, pancreatic endoderm and endocrine precursor en route to cells that express endocrine hormones".

In another example, Fisk et al. reports a system for producing pancreatic islet cells from human embryonic stem cells (US2006/0040387A1). In this case, the differentiation pathway was divided into three stages. Human embryonic stem cells were first differentiated to endoderm using a combination of n-butyrate and activin-A. The cells were then cultured with TGFβ antagonists such as Noggin in combination with EGF or betacellulin to generate PDX-1 positive cells. The terminal differentiation was induced by nicotinamide.

In one example, Benvenistry et al. states: "We conclude that over-expression of PDX-1 enhanced expression of pancreatic enriched genes, induction of insulin expression may require additional signals that are only present in vivo" (Benvenistry et al., Stem Cells 2006; 24:1923-1930).

Current methods to culture human embryonic stem cells requires the use of either extracellular matrix proteins or a fibroblast feeder layer, or the addition of exogenous growth factors, such as, for example, bFGF.

In one example, Cheon et al (BioReprod DOI: 10.1095/biolreprod.105.046870, Oct. 19, 2005) disclose a feeder-free, serum-free culture system in which embryonic stem cells are maintained in unconditioned serum replacement (SR) medium supplemented with different growth factors capable of triggering embryonic stem cell self-renewal.

In another example, Levenstein et al (Stem Cells 24: 568-574, 2006) disclose methods for the long-term culture of human embryonic stem cells in the absence of fibroblasts or conditioned medium, using media supplemented with bFGF.

In another example, US20050148070 discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than just a fibroblast feeder layer, the medium supported the proliferation of stem cells in an undifferentiated state without feeder cells or conditioned medium.

In another example, US20050233446 discloses a defined media useful in culturing stem cells, including undifferentiated primate primordial stem cells. In solution, the media is substantially isotonic as compared to the stem cells being cultured. In a given culture, the particular medium comprises a base medium and an amount of each of bFGF, insulin, and ascorbic acid necessary to support substantially undifferentiated growth of the primordial stem cells.

In another example, U.S. Pat. No. 6,800,480 states "In one embodiment, a cell culture medium for growing primate-derived primordial stem cells in a substantially undifferentiated state is provided which includes a low osmotic pressure, low endotoxin basic medium that is effective to support the growth of primate-derived primordial stem cells. The basic medium is combined with a nutrient serum effective to support the growth of primate-derived primordial stem cells and a substrate selected from the group consisting of feeder cells and an extracellular matrix component derived from feeder cells. The medium further includes nonessential amino acids, an anti-oxidant, and a first growth factor selected from the group consisting of nucleosides and a pyruvate salt."

In another example, US20050244962 states: "In one aspect the invention provides a method of culturing primate embryonic stem cells. One cultures the stem cells in a culture essentially free of mammalian fetal serum (preferably also essentially free of any animal serum) and in the presence of fibroblast growth factor that is supplied from a source other than just a fibroblast feeder layer. In a preferred form, the fibroblast feeder layer, previously required to sustain a stem cell culture, is rendered unnecessary by the addition of sufficient fibroblast growth factor."

In a further example, WO2005065354 discloses a defined, isotonic culture medium that is essentially feeder-free and serum-free, comprising: a. a basal medium; b. an amount of bFGF sufficient to support growth of substantially undifferentiated mammalian stem cells; c. an amount of insulin sufficient to support growth of substantially undifferentiated mammalian stem cells; and d. an amount of ascorbic acid sufficient to support growth of substantially undifferentiated mammalian stem cells.

In another example, WO2005086845 discloses a method for maintenance of an undifferentiated stem cell, said method comprising exposing a stem cell to a member of the transforming growth factor-beta (TGFβ) family of proteins, a member of the fibroblast growth factor (FGF) family of proteins, or nicotinamide (NIC) in an amount sufficient to maintain the cell in an undifferentiated state for a sufficient amount of time to achieve a desired result.

Additionally, formation of pancreatic endocrine cells, pancreatic hormone expressing cells, or pancreatic hormone secreting cells from human embryonic cells may require genetic manipulation of the human embryonic stem cells. Transfection of human embryonic stem cells using traditional techniques, such as, for example, lipofectamine or electroporation is inefficient.

WO2007027157 discloses a method comprising: (a) providing an embryonic stem (ES) cell; and (b) establishing a progenitor cell line from the embryonic stem cell; in which the progenitor cell line is selected based on its ability to self-renew. Preferably, the method selects against somatic cells based on their inability to self renew. Preferably, the progenitor cell line is derived or established in the absence of co-culture, preferably in the absence of feeder cells, which preferably selects against embryonic stem cells. Optionally, the method comprises (d) deriving a differentiated cell from the progenitor cell line.

Therefore, there still remains a significant need to develop conditions for establishing pluripotent stem cell lines that can be expanded to address the current clinical needs, while retaining the potential to differentiate into pancreatic endocrine cells, pancreatic hormone expressing cells, or pancreatic hormone secreting cells.

SUMMARY

The present invention provides a cell population with characteristics of human embryonic stem cells, that can be readily expanded in culture, in low serum, that requires no feeder cell line or a coating of complex matrix proteins, can be passaged in single cell suspension, can be transfected with a very high efficiency, and cultured under hypoxic conditions. This combination of unique attributes separates the cells described in the present invention from the prior art.

In one embodiment, the present invention provides a method for deriving a population of cells comprising cells expressing pluripotency markers, comprising the steps of:

a. Obtaining cells, and
b. Culturing the cells under hypoxic conditions, on a tissue culture substrate that is not pre-treated with a protein or an extracellular matrix prior to culturing the cells.

The cells may be human embryonic stem cells, or they may be cells expressing markers characteristic of the definitive endoderm lineage. The human embryonic stem cells may be cultured in normoxic conditions prior to culturing the cells on a tissue culture substrate that is not pre-treated with a protein or an extracellular matrix. Alternatively, the human embryonic stem cells may be cultured in hypoxic conditions.

The human embryonic stem cells may be cultured in normoxic conditions prior to culturing the cells on a tissue culture substrate that is not pre-treated with a protein or an extracellular matrix, and treated with a Rho kinase inhibitor. Alternatively, the human embryonic stem cells may be cultured in hypoxic conditions, and treated with a Rho kinase inhibitor.

The cells expressing markers characteristic of the definitive endoderm lineage may be cultured in normoxic conditions prior to culturing the cells on a tissue culture substrate that is not pre-treated with a protein or an extracellular matrix. Alternatively, the cells expressing markers characteristic of the definitive endoderm lineage may be cultured in hypoxic conditions.

In one embodiment, the present invention provides a method for deriving a population of cells comprising cells expressing pluripotency markers, comprising the steps of:

a. Culturing human embryonic stem cells,
b. Differentiating the human embryonic stem cells into cells expressing markers characteristic of definitive endoderm cells, and
c. Removing the cells, and subsequently culturing them under hypoxic conditions, on a tissue culture substrate that is not pre-treated with a protein or an extracellular matrix prior to culturing the cells.

The cells may be cultured under hypoxic conditions, on a tissue culture substrate that is not pre-treated with a protein or an extracellular matrix, in medium containing serum, activin-A, and a Wnt ligand. Alternatively, the cells may be cultured under hypoxic conditions, on a tissue culture substrate that is not pretreated with a protein or an extracellular matrix, in medium containing serum, activin-A, a Wnt ligand, and IGF-1.

The cells may be cultured under hypoxic conditions, on a tissue culture substrate that is not pre-treated with a protein or an extracellular matrix, in medium containing serum, a Rho kinase inhibitor, activin-A, and a Wnt ligand. Alternatively, the cells may be cultured under hypoxic conditions, on a tissue culture substrate that is not pretreated with a protein or an extracellular matrix, in medium containing serum, a Rho kinase inhibitor, activin-A, a Wnt ligand, and IGF-1.

In one embodiment, the present invention provides a method for deriving a population of cells comprising cells expressing pluripotency markers, comprising the steps of:

a. Culturing human embryonic stem cells, and
b. Removing the cells, and subsequently culturing them under hypoxic conditions, on a tissue culture substrate that is not pre-treated with a protein or an extracellular matrix.

The cells may be cultured under hypoxic conditions, on a tissue culture substrate that is not pre-treated with a protein or an extracellular matrix, in medium containing serum, activin-A, and a Wnt ligand. Alternatively, the cells may be cultured under hypoxic conditions, on a tissue culture substrate that is not pretreated with a protein or an extracellular matrix, in medium containing serum, activin-A, a Wnt ligand, and IGF-1.

The cells may be cultured under hypoxic conditions, on a tissue culture substrate that is not pre-treated with a protein or an extracellular matrix, in medium containing serum, a Rho kinase inhibitor, activin-A, and a Wnt ligand. Alternatively, the cells may be cultured under hypoxic conditions, on a tissue culture substrate that is not pretreated with a protein or an extracellular matrix, in medium containing serum, a Rho kinase inhibitor, activin-A, a Wnt ligand, and IGF-1.

The cells expressing pluripotency markers derived by the methods of the present invention are capable of expansion in culture under hypoxic conditions, on tissue culture substrate that is not pre-treated with a protein or an extracellular matrix.

In one embodiment, the present invention provides a method to expand cells expressing markers characteristic of the definitive endoderm lineage, comprising the steps of culturing the cells under hypoxic conditions, on a tissue culture substrate that is not pre-treated with a protein or an extracellular matrix. In one embodiment, the cells expressing markers characteristic of the definitive endoderm lineage are derived from pluripotent cells formed by the methods of the present invention.

The cells may be cultured under hypoxic conditions, on a tissue culture substrate that is not pre-treated with a protein or an extracellular matrix, in medium containing serum, activin-A, a Wnt ligand, and a GSK-3B inhibitor.

100 ng/ml of AA+20 ng/ml of WNT-3A+50 ng/ml of IGF-I and EXPRES 02 cells were cultured in 2% FBS+DM-F12+100 ng/ml of AA+20 ng/ml of WNT-3A.

Figure 10:
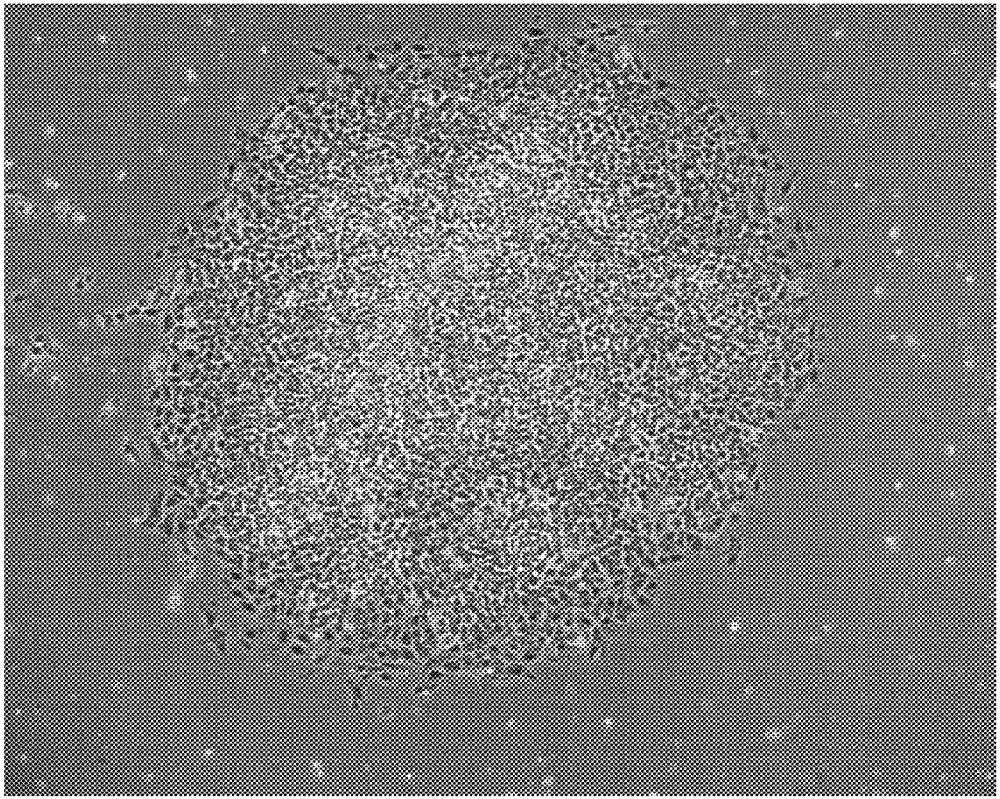

FIG. 10 shows the morphology of EXPRES cells derived from single cell suspension of undifferentiated ES cells on TCPS (tissue culture polystyrene) in DM-F12+2% FBS+100 ng/ml AA+20 ng/ml WNT3A+50 ng/ml of IGF-1.

Figure 11:
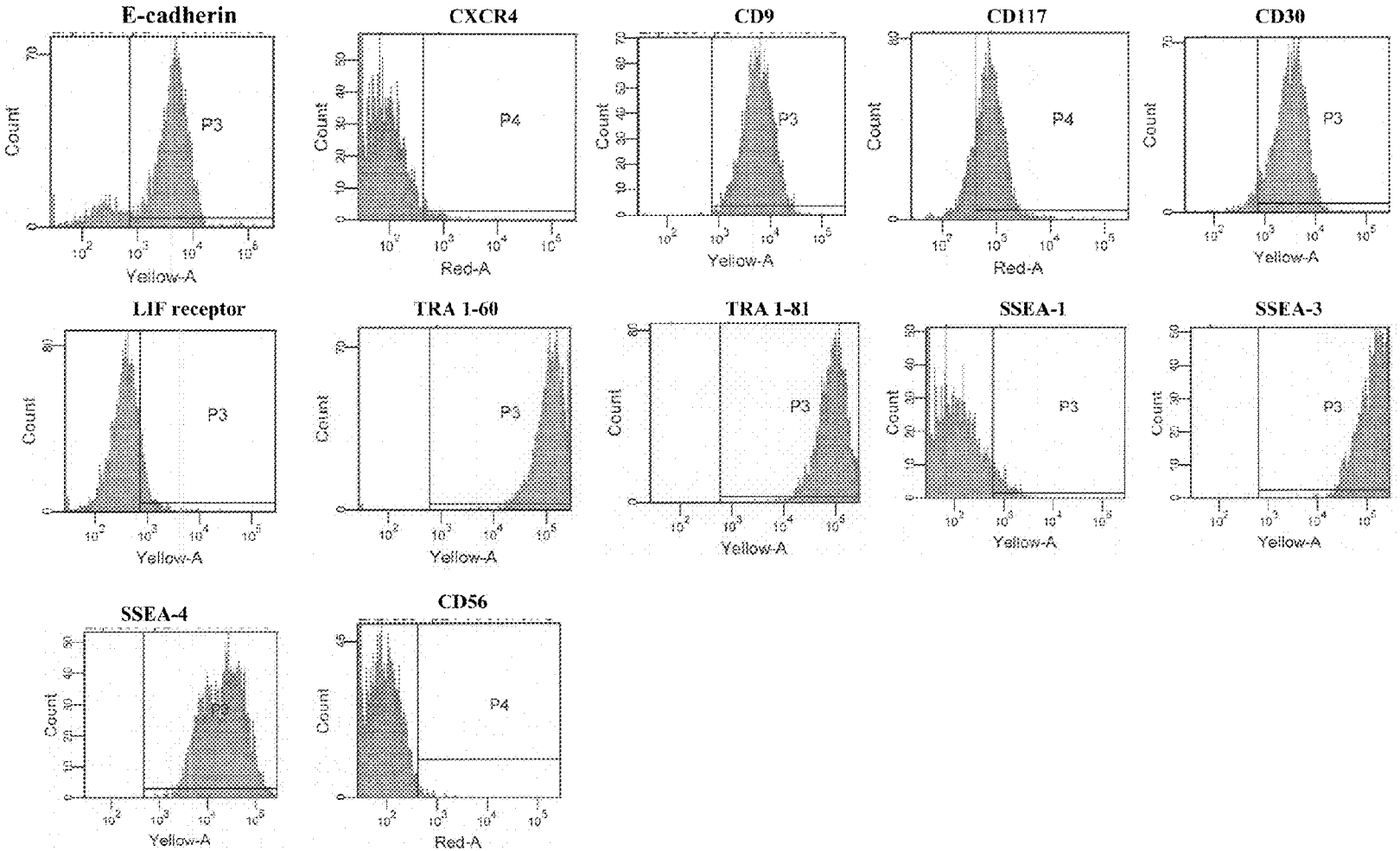

FIG. 11 shows the protein expression as determined by FACS in EXPRES 01 cells at passage 24 cells. Panel a) shows the expression levels of E-cadherin, panel b) shows the expression levels of CXCR4, panel c) shows the expression levels of CD9, panel d) shows the expression levels of CD117, panel e) shows the expression levels of CD30, panel f) shows the expression levels of LIF receptor, panel g) shows the expression levels of TRA 1-60, panel h) shows the expression levels of TRA 1-81, panel i) shows the expression levels of SSEA-1, panel j) shows the expression levels of SSEA-3, panel k) shows the expression levels of SSEA-4, and Panel l) shows the expression levels of CD56.

Figure 12:
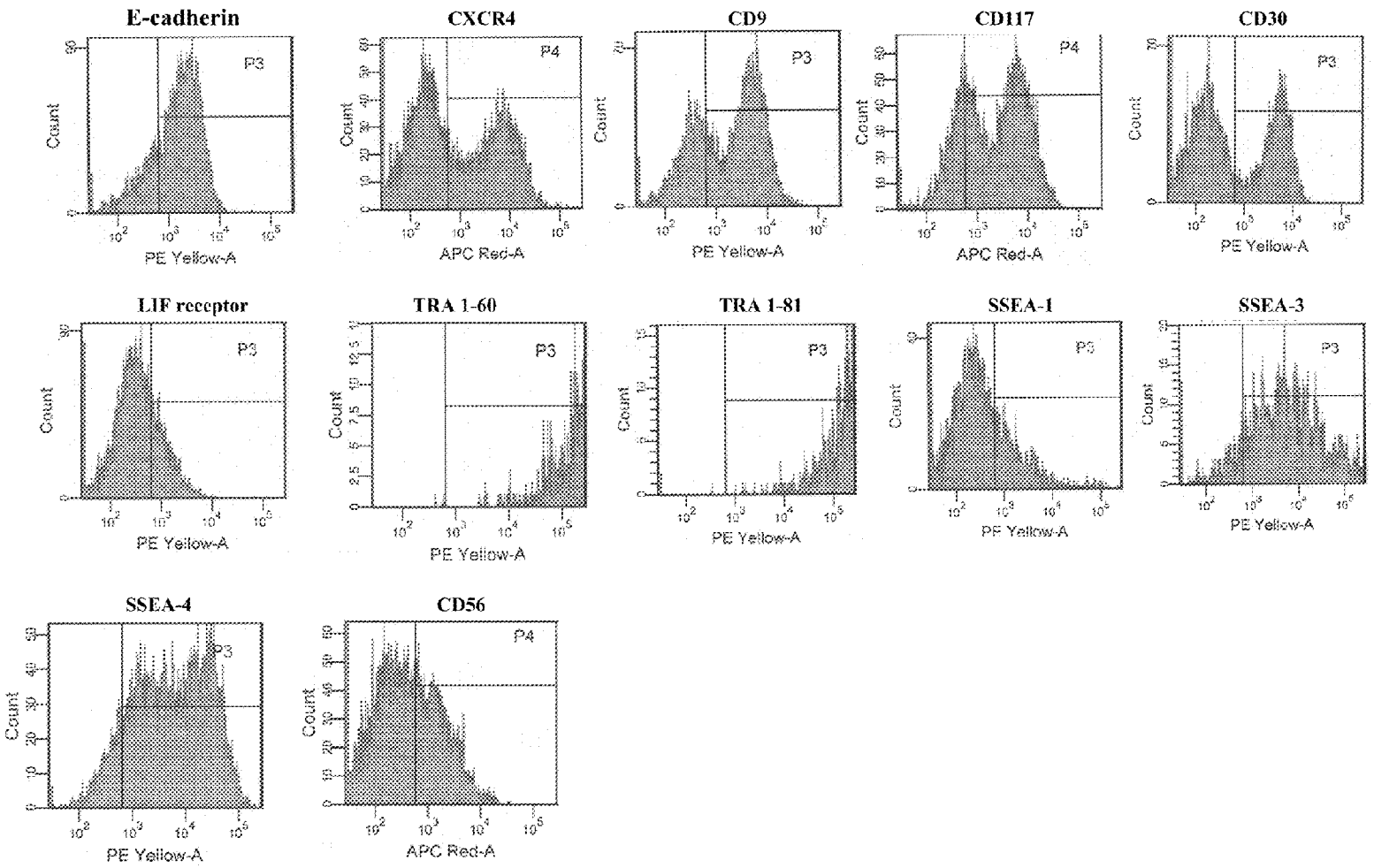

FIG. 12 shows the protein expression as determined by FACS in EXPRES 02 at passage 21 cells. Panel a) shows the expression levels of E-cadherin, panel b) shows the expression levels of CXCR4, panel c) shows the expression levels of CD9, panel d) shows the expression levels of CD117, panel e) shows the expression levels of CD30, panel f) shows the expression levels of LIF receptor, panel g) shows the expression levels of TRA 1-60, panel h) shows the expression levels of TRA 1-81, panel i) shows the expression levels of SSEA-1, panel j) shows the expression levels of SSEA-3, panel k) shows the expression levels of SSEA-4, and panel l) shows the expression levels of CD56.

Figure 13:
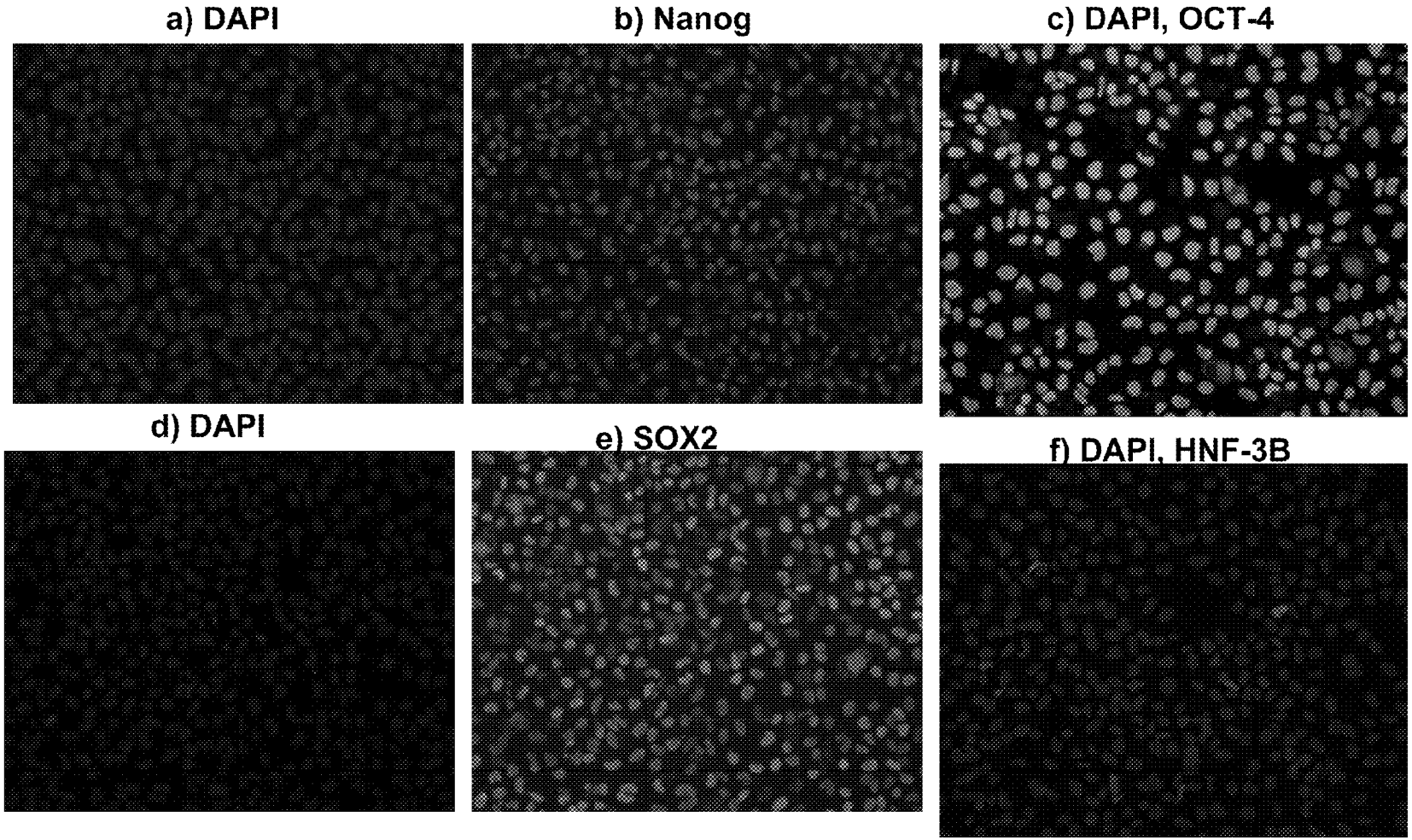

FIG. 13 shows immuno fluorescent images of EXPRES 01 at passage 10 cultured in 2% FBS+DMEM-F12+100 ng/ml of AA+20 ng/ml of WNT-3A+50 ng/ml of IGF-I. Panel a) DAPI image for panel b, panel b) Nanog, panel c) DAPI (blue) and Oct-4 (green) co-staining, panel d) DAPI image for panel e, panel e) SOX-2, and panel f) DAPI (blue) and HNF-3 beta (green) co-staining.

Figure 14:
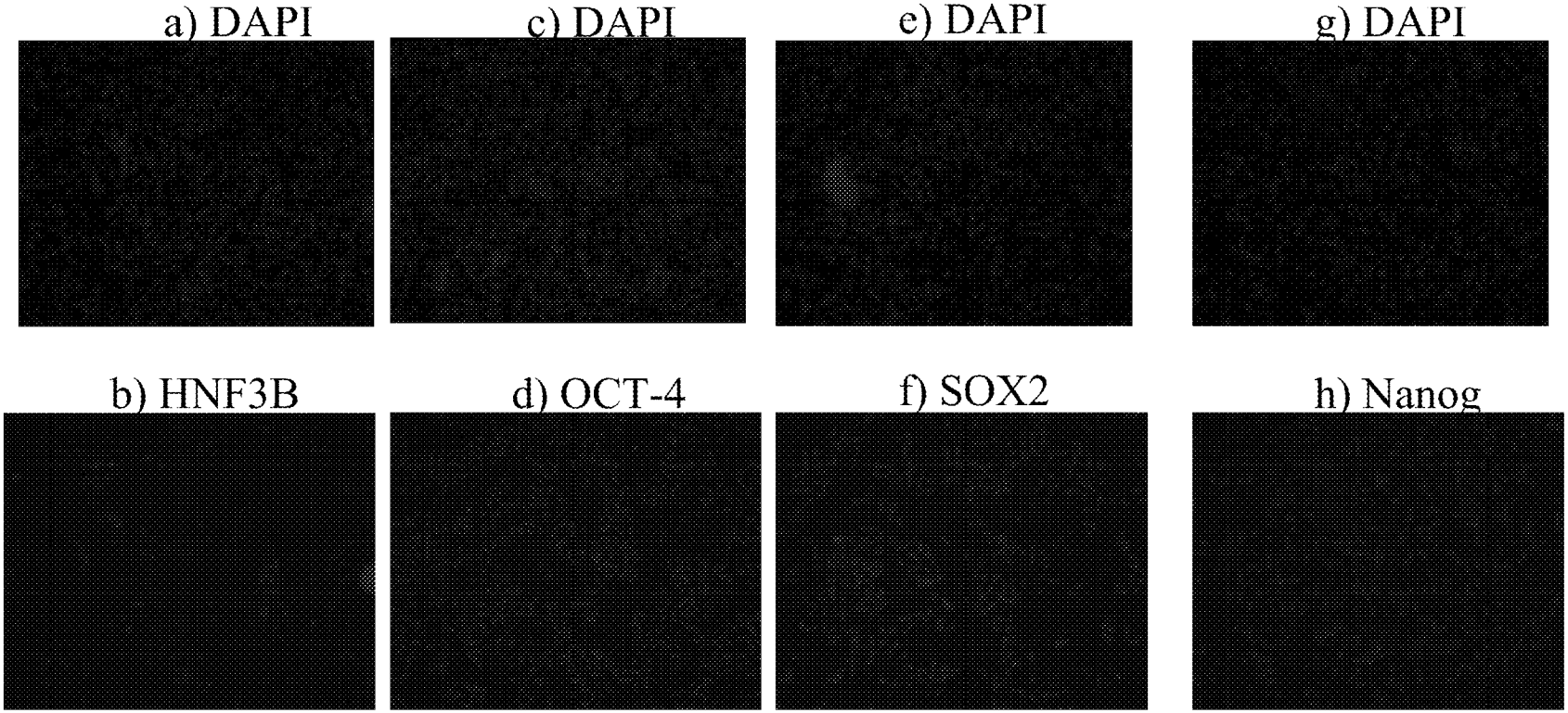

FIG. 14 shows immuno fluorescent images of EXPRES 02 at passage 9 cultured in 2% FBS+DMEM-F12+100 ng/ml of AA+20 ng/ml of WNT-3A. Panel a) DAPI image for panel b, panel b) HNf3B, panel c) DAPI image for panel d, panel d) OCT-4, panel e) DAPI image for panel f, panel f) SOX-2, panel g) DAPI image for panel h, panel h) NANOG.

Figure 15:
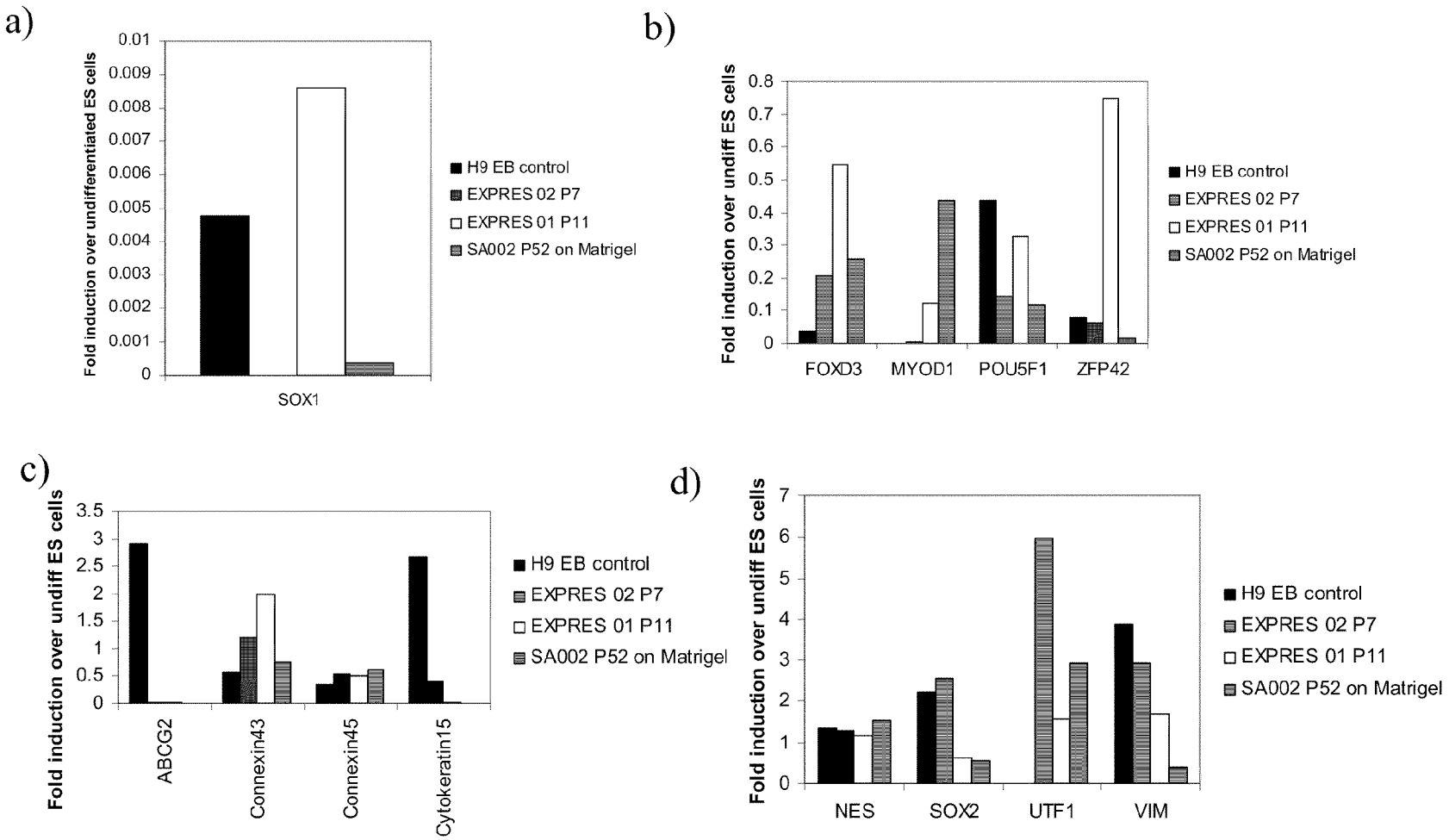
Figure 15:
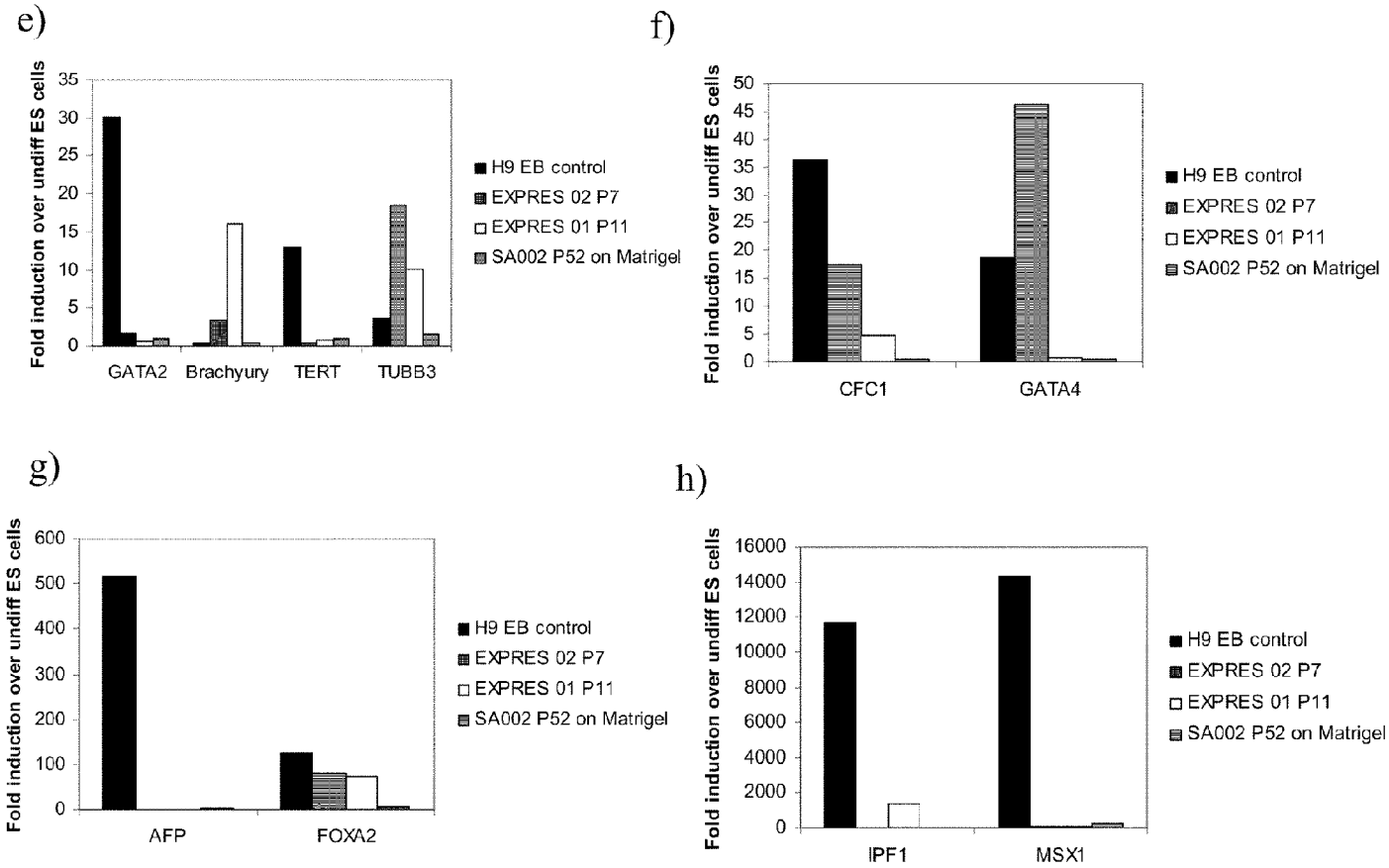

FIG. 15 shows gene expression as determined by real-time PCR for EXPRES 01 cells, EXPRES 02 cells, EB derived from H9 cells, SA002 cultured on MATRIGEL in MEF-CM, and undifferentiated H9 cells cultured on MATRIGEL in MEFCM. All the expression levels are normalized to undifferentiated H9 cells. Panel a) shows SOX-1 expression, panel b) shows FOXD3, MYOD1, POU5F1, and ZFP42 expression, panel c) shows ABCG2, Connexin 43, Connexin 45, and cytokeratin 15 expression, panel d) shows nestin, SOX-2, UTF1, and vimentin, panel e) shows GATA-2, Brachyury, TERT, and tubulin-beta III expression, panel f) shows CFC1, and GATA-4 expression, Panel g) shows AFP and FOXA2 expression, and Panel h) shows IPF1A and MSX1 expression.

Figure 16:
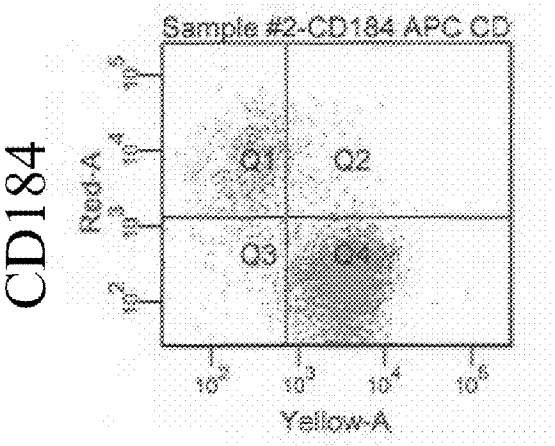
Figure 16:
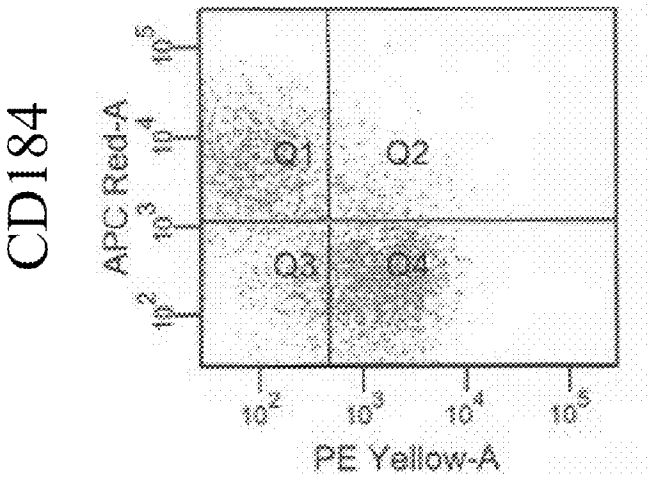

FIG. 16 shows the expression, as determined by FACS of CXCR4 (Y-axis) and CD9 (x-axis) in a) EXPRES 01 cells passage 5 cells cultured on tissue culture polystyrene in growth media and then switched to DMEM-F12+0.5% FBS+100 ng/ml of activin-A and 20 ng/ml of WNT3A for 2 days followed by additional 2 days in DMEM-F12+2% FBS+100 ng/ml of activin-A, b) EXPRES 02 cells passage 4 cells cultured on tissue culture polystyrene in growth media and then switched to DMEM-F12+0.5% FBS+100 ng/ml of activin-A and 20 ng/ml of WNT3A for 2 days followed by additional 2 days in DMEM-F12+2% FBS+100 ng/ml of activin-A.

Figure 17:
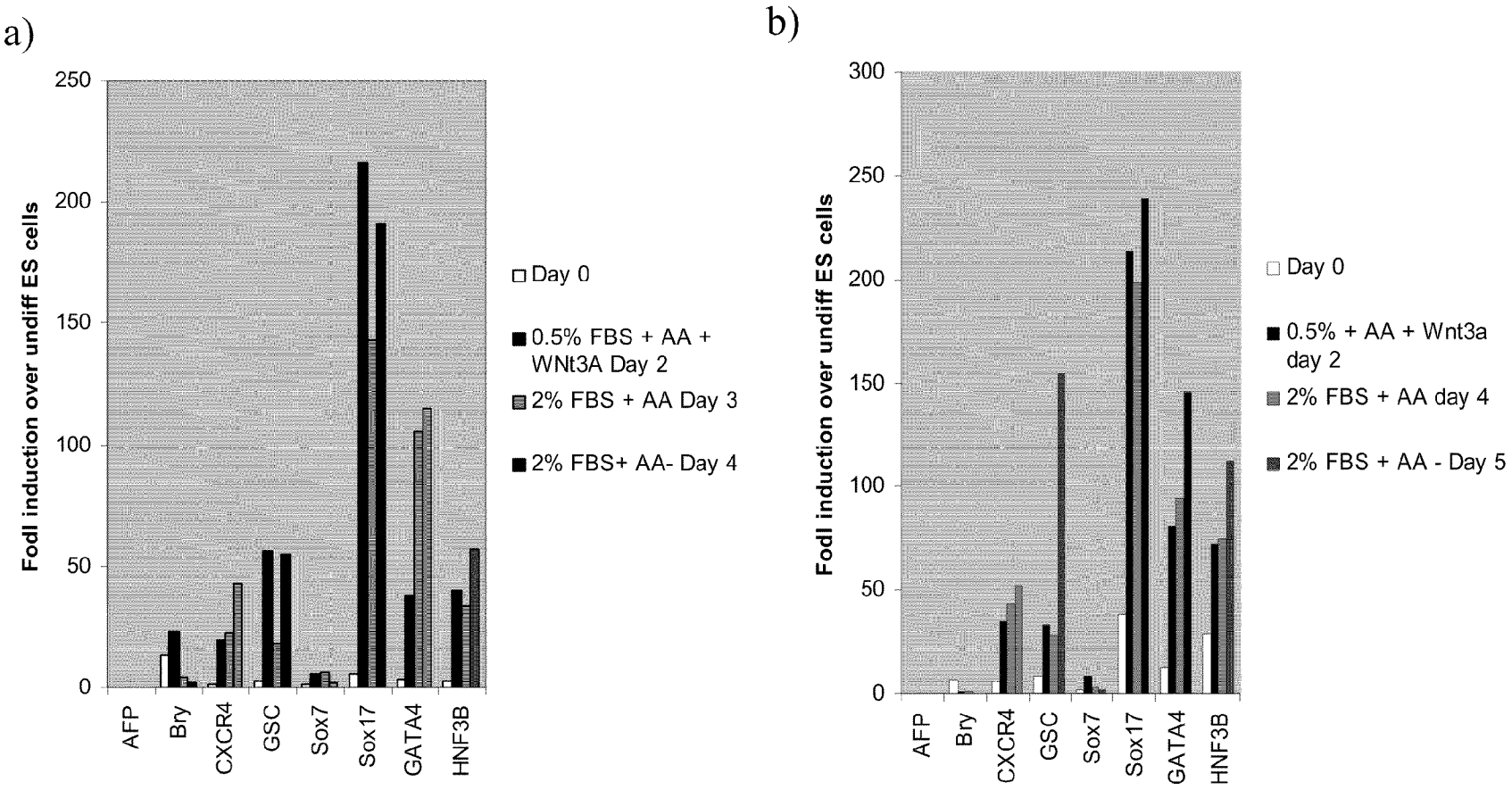

FIG. 17 shows gene expression as determined by real-time PCR in a) EXPRES 01 cells and b) EXPRES 02 cells treated with low serum plus AA+WNT3a.

Figure 18:
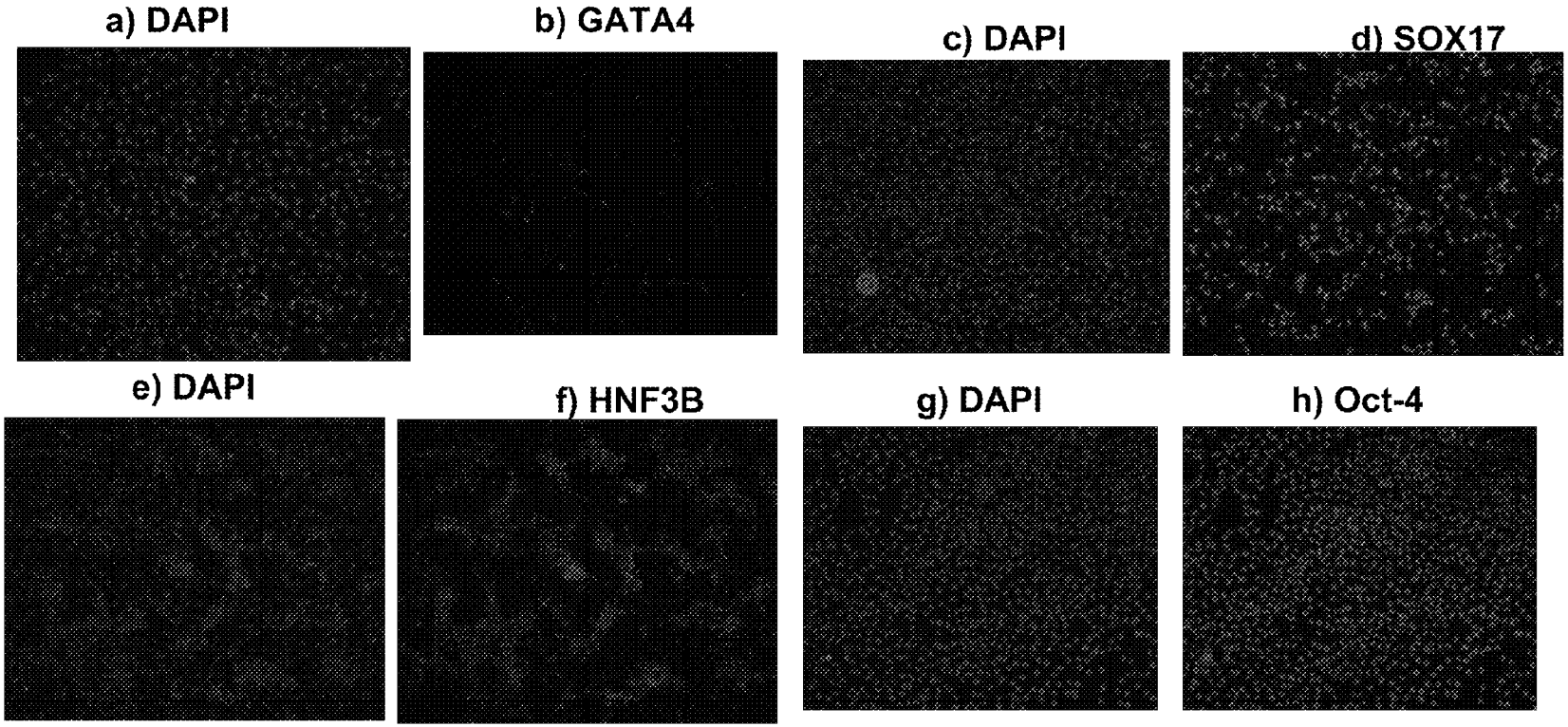

FIG. 18 shows immuno fluorescent images of EXPRES 01 cells at passage 5 cultured in 2% FBS+DMEM-F12+100 ng/ml of AA+20 ng/ml of WNT-3A+50 ng/ml of IGF-I and then switched to DMEM-F12+0.5% FBS+100 ng/ml of activin-A and 20 ng/ml of WNT3A for 2 days, followed by additional 2 days in DMEM-F12+2% FBS+100 ng/ml of activin-A. Panel a) DAPI image for panel b, panel b) GATA-4, panel c) DAPI image for panel d, panel d) SOX-17, panel e) DAPI image for panel f, panel f) HNF-3 beta, panel g) DAPI image for panel h, and panel h) OCT-4.

Figure 19:
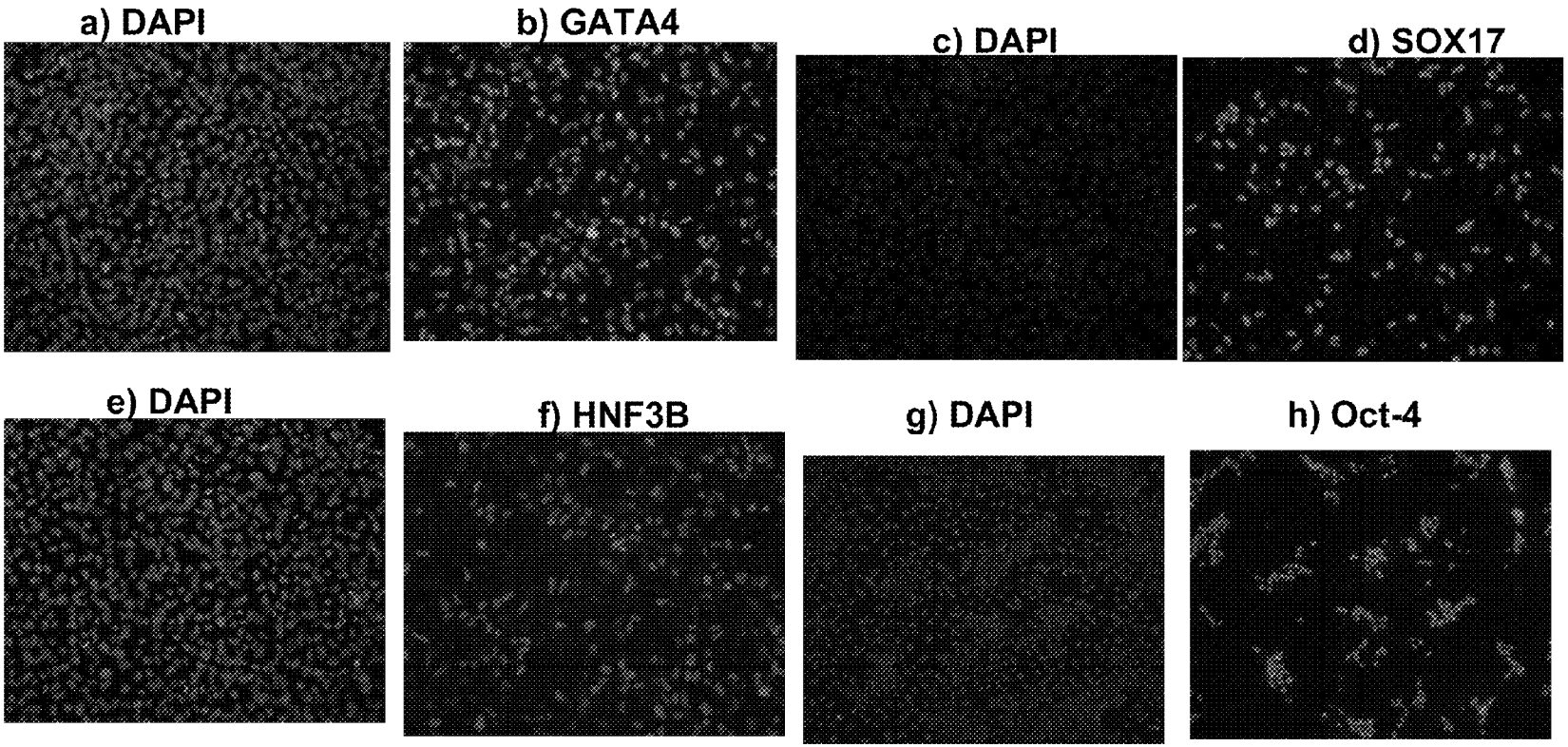

FIG. 19 shows immuno fluorescent images of EXPRES 02 cells at passage 4 cultured in 2% FBS+DMEM-F12+100 ng/ml of AA+20 ng/ml of WNT-3A and then switched to DMEM-F12+0.5% FBS+100 ng/ml of activin-A and 20 ng/ml of WNT3A for 2 days followed by additional 2 days in DMEM-F12+2% FBS+100 ng/ml of activin-A. Panel a) DAPI image for panel b, panel b) GATA-4, panel c) DAPI image for panel d, panel d) SOX-17, panel e) DAPI image for panel f, panel f) HNF-3 beta, panel g) DAPI image for panel h, and panel h) OCT-4.

Figure 20:
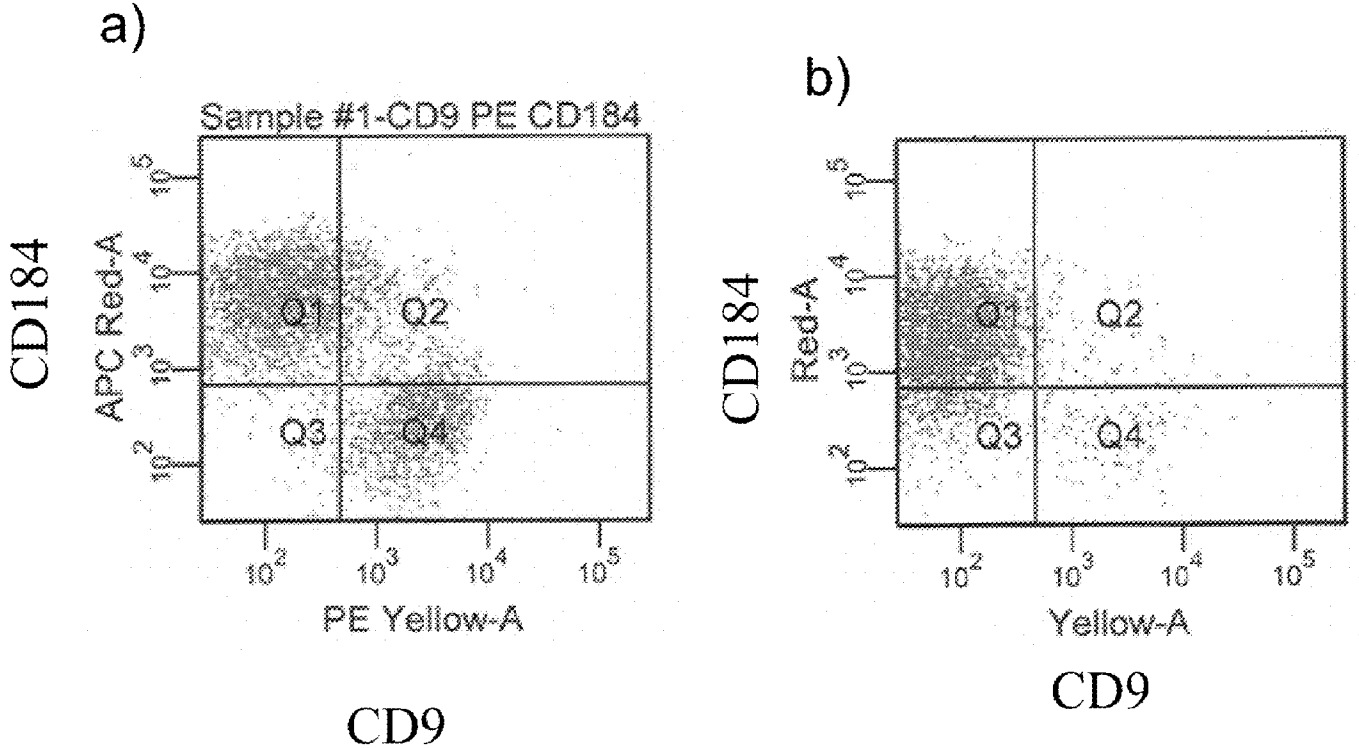

FIG. 20 shows protein expression as determined by FACS of CXCR4 (Y-axis) and CD9 (x-axis) for a) EXPRES 01 cells at passage 19 cells and b) EXPRES 02 cells at passage 14 cells cultured on tissue culture polystyrene in growth media and then switched to DMEM-F12+0.5% FBS+100 ng/ml of activin-A+100 nM GSK-3B inhibitor IX, and 20 ng/ml of WNT3A for 4 days.

Figure 21:
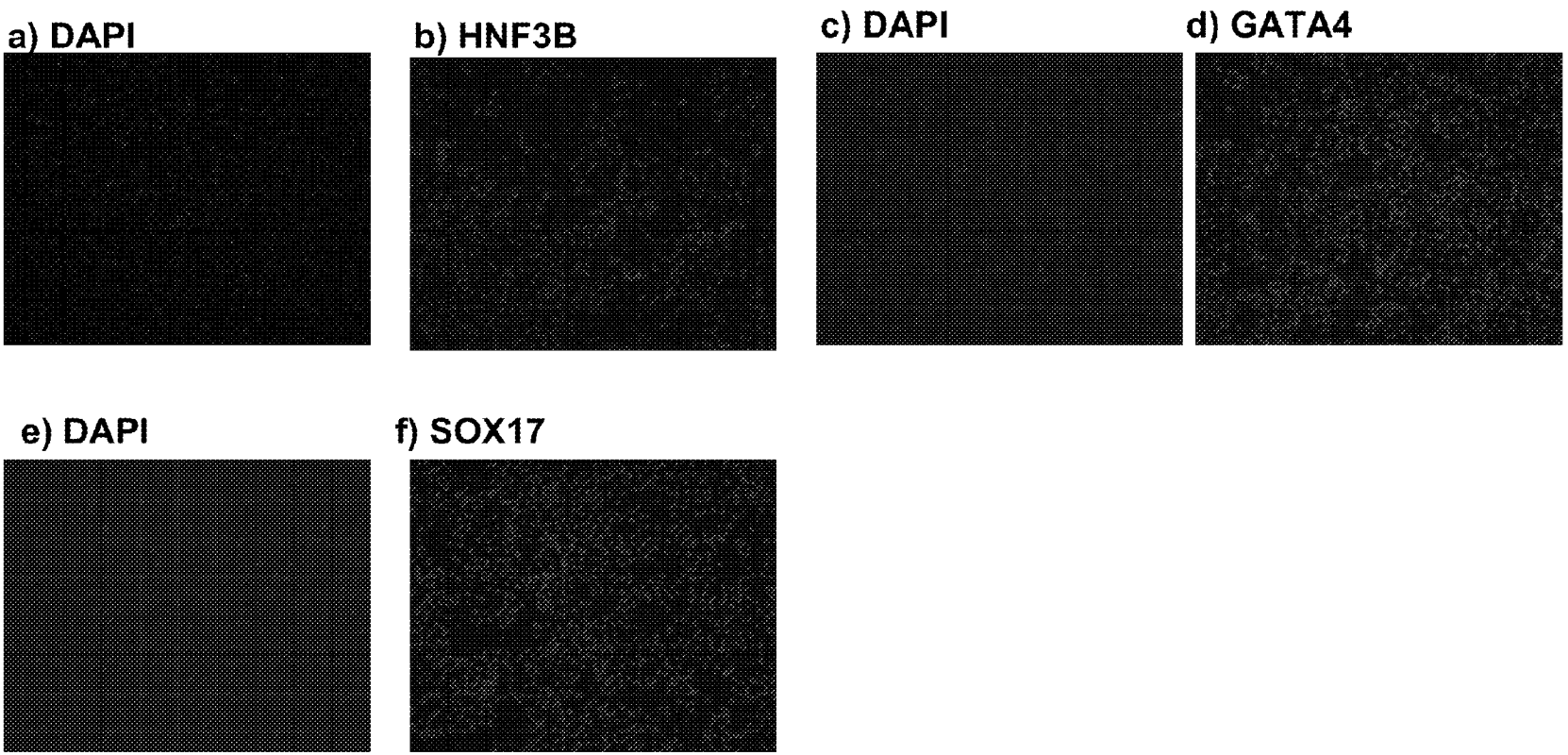
Figure 21:
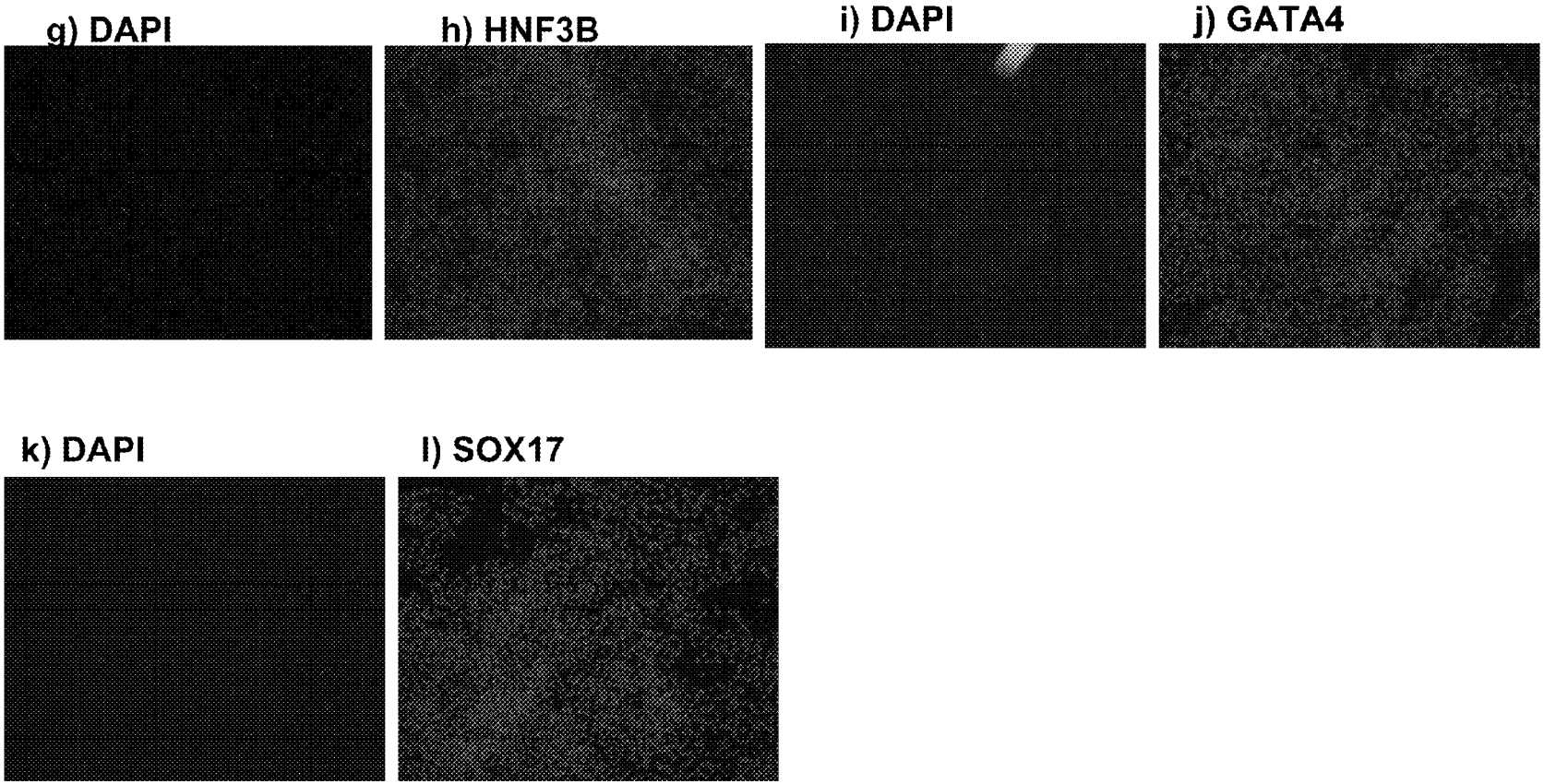

FIG. 21 shows immuno fluorescent images of EXPRES 01 cells at passage 19 cultured in 2% FBS+DMEM-F12+100 ng/ml of AA+20 ng/ml of WNT-3A+50 ng/ml of IGF-I and EXPRES 02 cells at passage 14 cultured in 2% FBS+DMEM-F12+100 ng/ml of AA+20 ng/ml of WNT-3A and then switched to DMEM-F12+0.5% FBS+100 ng/ml of activin-A+100 nM GSK-3B inhibitor IX, and 20 ng/ml of WNT3A for 5 days. Panel a) DAPI image for panel b, panel b) HNF-3 beta, panel c) DAPI image for panel d, panel d) GATA-4, panel e) DAPI image for panel f, panel f) SOX-17, panel g) DAPI image for panel h, panel h) HNF-3 beta, Panel i) DAPI image for panel j, panel j) GATA-4, panel k) DAPI image for panel l, panel l) SOX-17.

Figure 22:
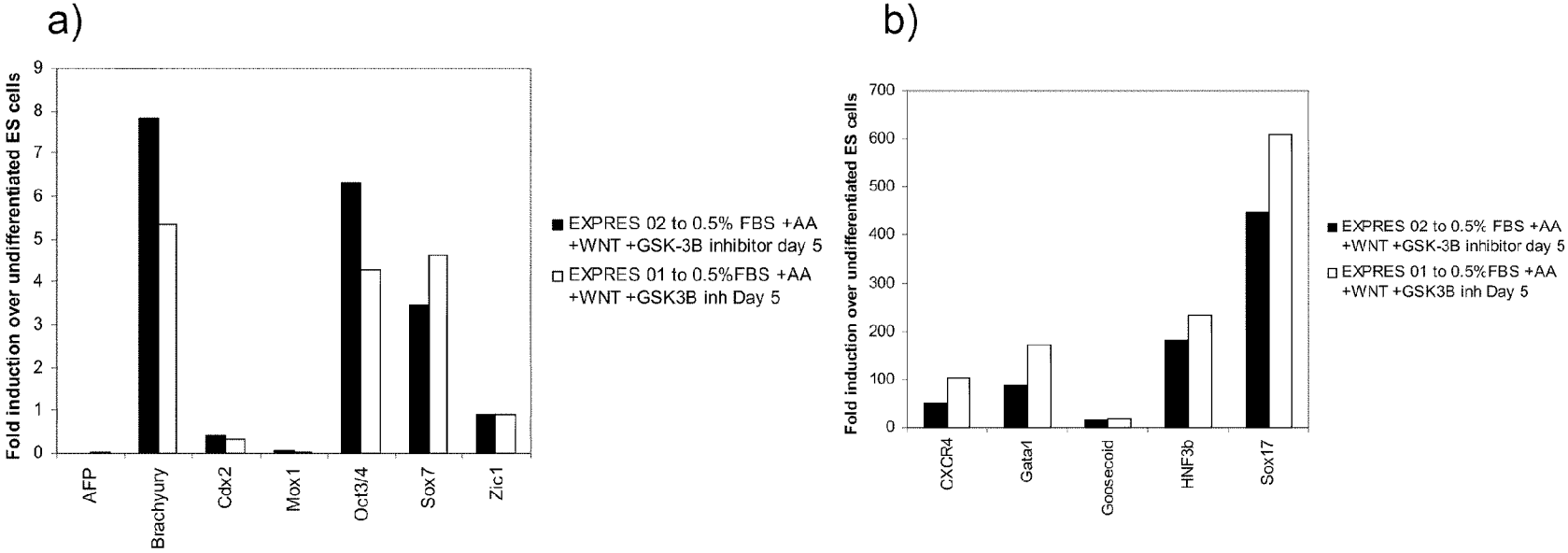

FIG. 22 shows gene expression as determined by real-time PCR data for a) EXPRES 01 and EXPRES 02 cells treated with low serum plus AA+WNT3a+GSK-3B IX inhibitor for 5 days. Panel a depicts expression of AFP, Brachyury, CDX2, Mox1, OCT3/4, SOX-7, and ZIC1 and panel b shows expression levels of CXCR4, GATA-4, Goosecoid, HNf3B, and SOX-17.

Figure 23:
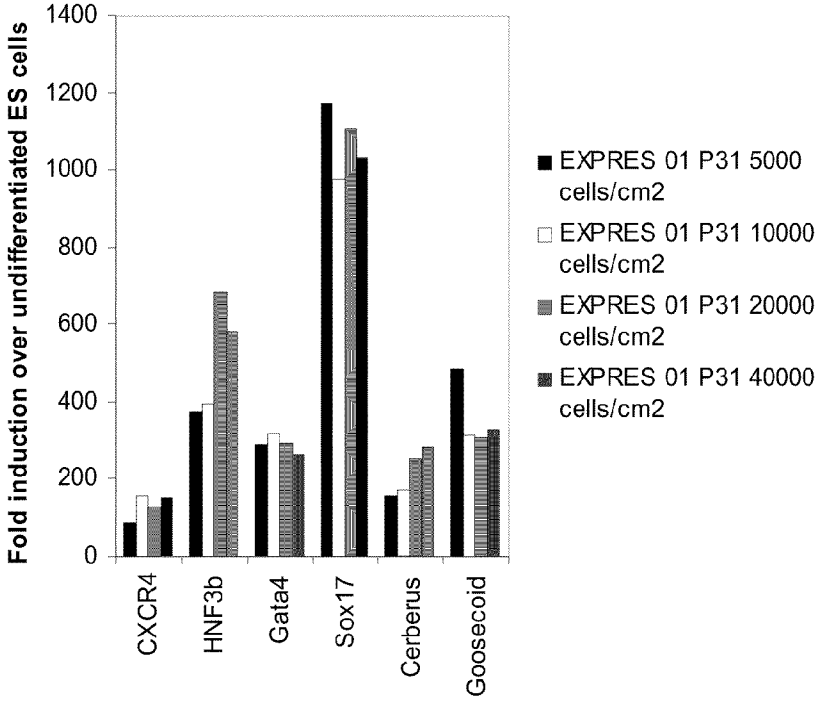
Figure 23:
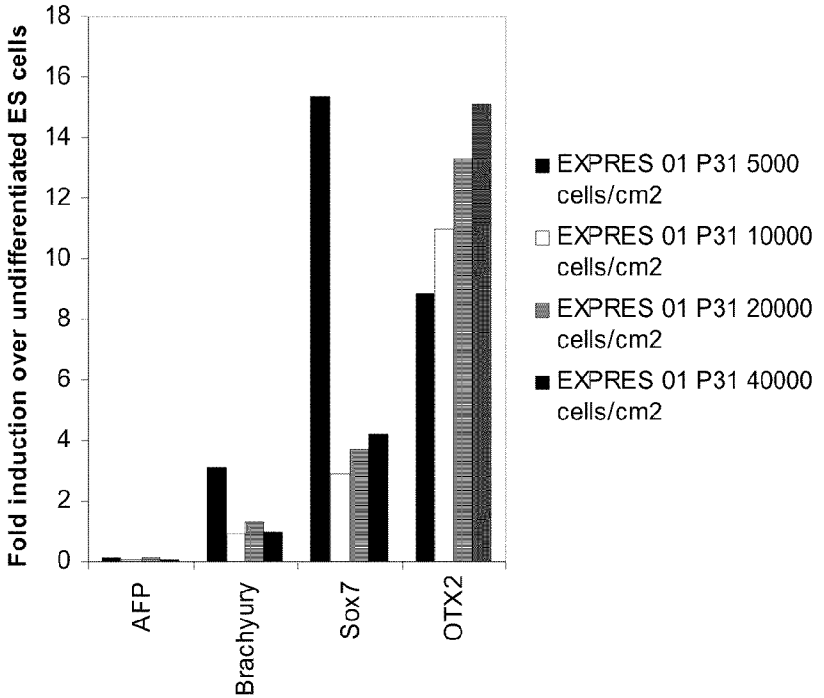

FIG. 23 shows gene expression as determined by real-time PCR for EXPRES 01 cells seeded at 5000-40000 cell s/cm$^2$ on tissue culture polystyrene in growth media and then switched to DMEM-F12+0.5% FBS+100 ng/ml AA+20 ng/ml WNT3A+100 nM GSK-3B inhibitor IX for four days under hypoxic conditions. Panel a depicts expression levels of AFP, Brachyury, SOX-7, and OTX2. Panel b depicts expression levels of CXCR4, HNF-3 beta, GATA-4, SOX-17, Cerb, and GSC.

Figure 24:
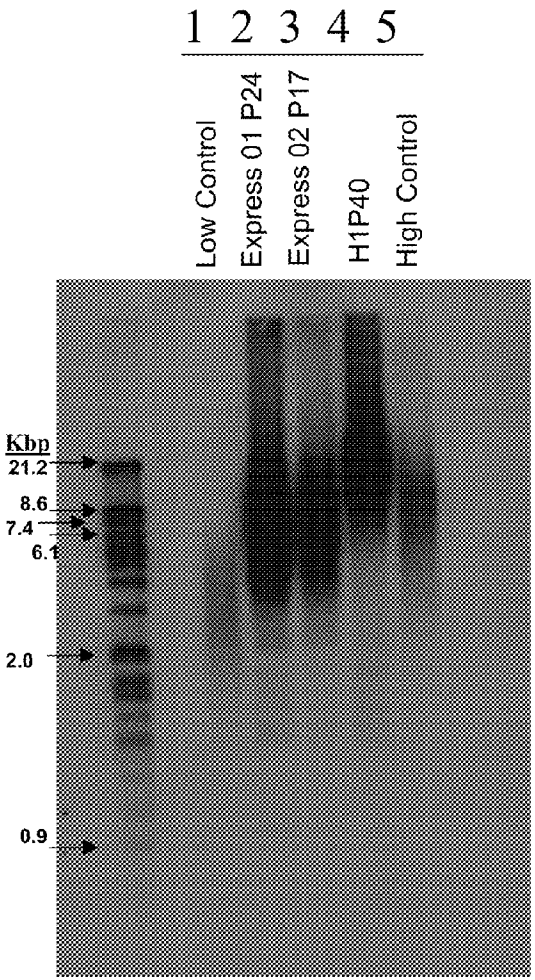

FIG. 24 shows the results of a telomere length assay in low telomere control cells (lane 1), EXPRES 01 cells at passage 24 (lane 2), EXPRES 02 cells at passage 17 (lane 3), undifferentiated cells from the human embryonic stem cell line H1 at passage 40 (lane 4), and high telomere length control cells (lane 5).

Figure 25:
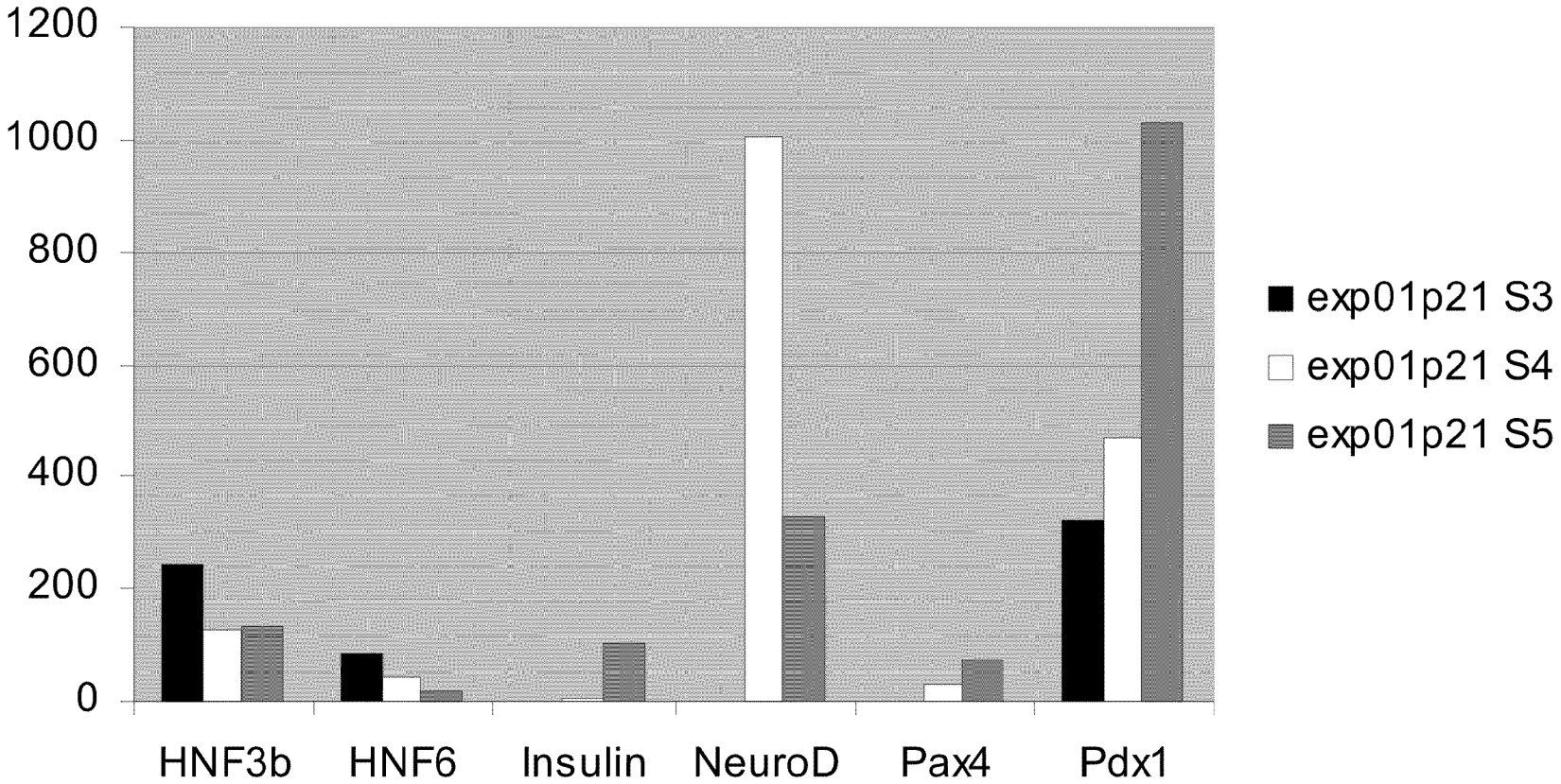

FIG. 25 shows gene expression as determined by real-time PCR data for EXPRES 01 cells at passage 21 that have been differentiated to foregut endoderm cells (S3), pancreatic endoderm cells (S4), and pancreatic endocrine cells (S5).

Figure 26:
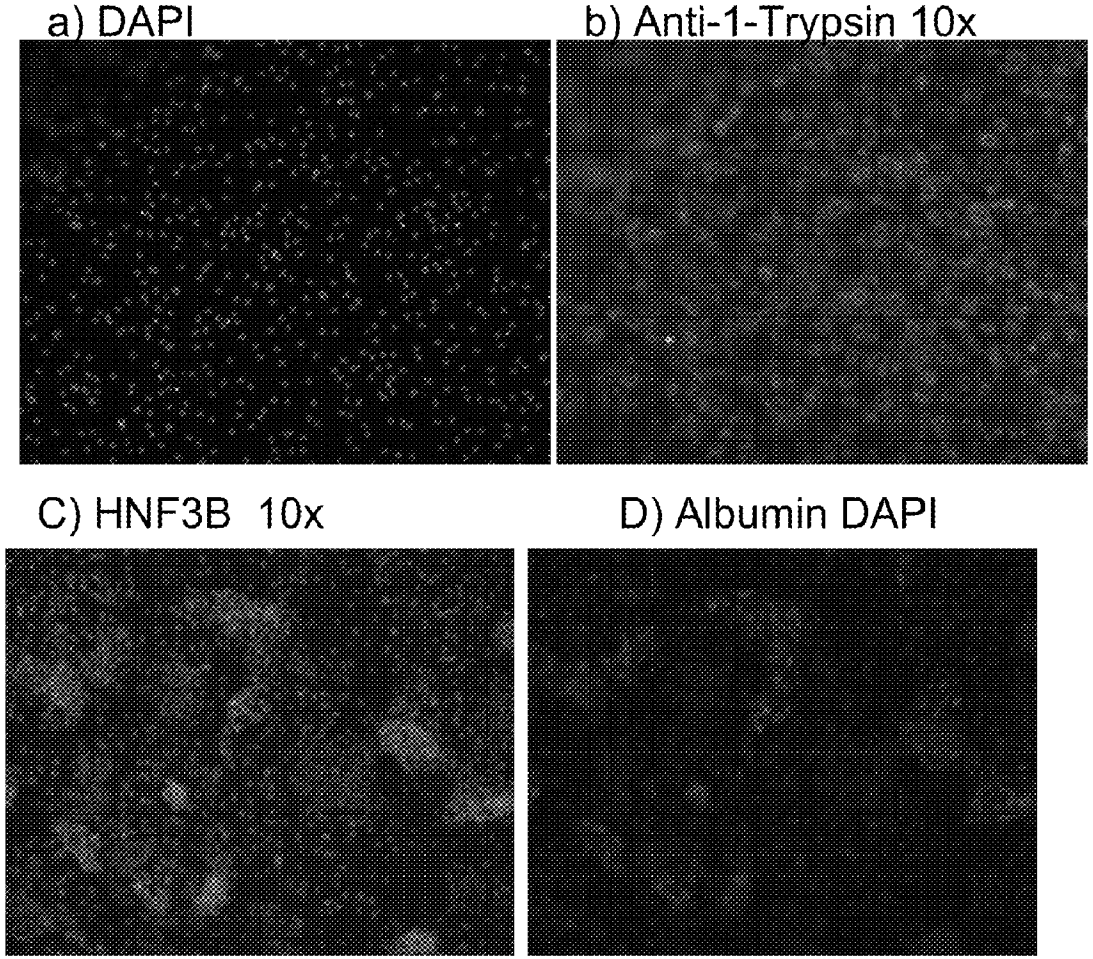
Figure 26:
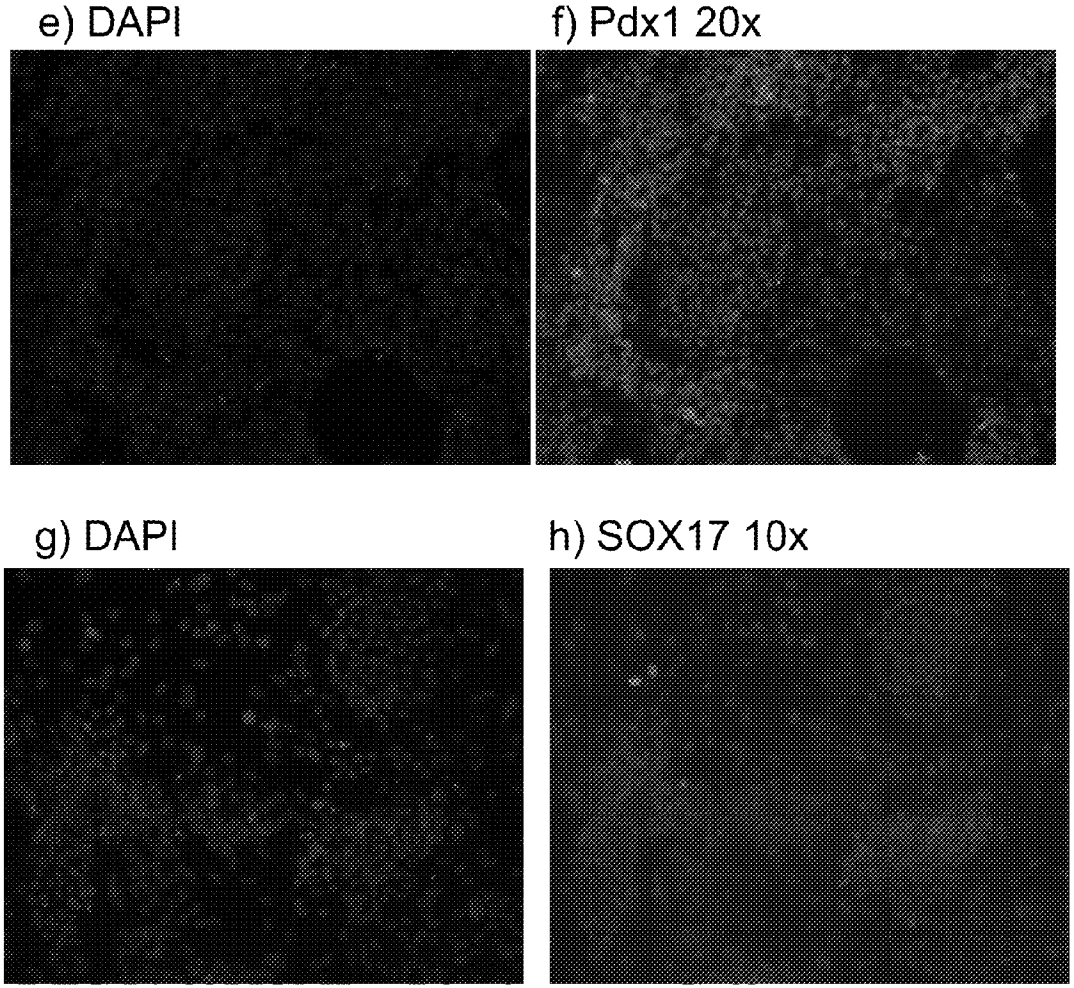
Figure 26:
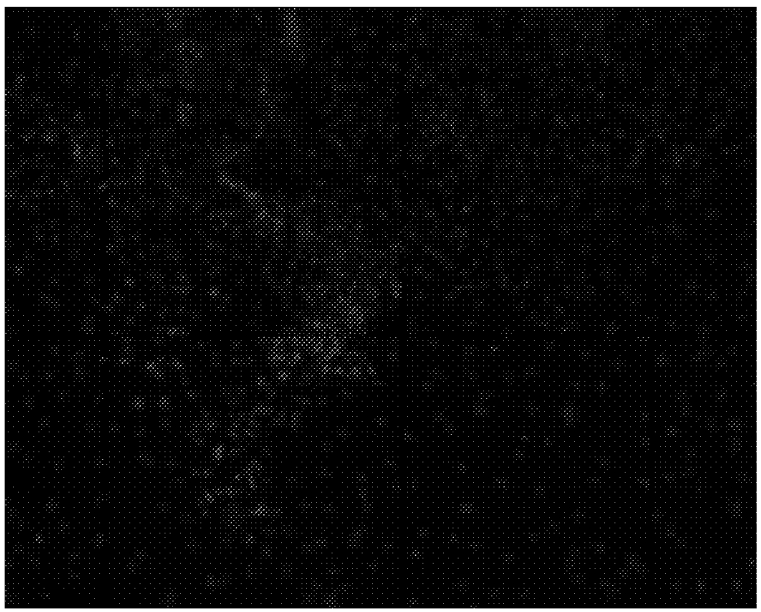
Figure 26:
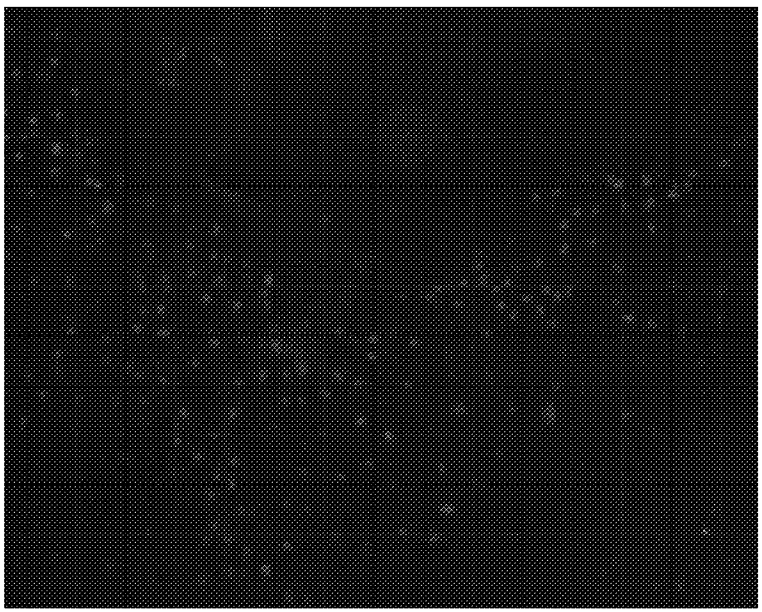

FIG. 26 shows immuno fluorescent images of EXPRES 01 at passage 35 cultured according to Example 18. Panel a) DAPI image for panel b, panel b) Anti-1 trypsin, panel c) HNF-3 beta in green Albumin in Red, panel d)Albumin in red and DAPI (blue), panel e) DAPI image for panel f, panel f) PDX-1, panel g) DAPI image for panel h, panel h) SOX-17, panel i) DAPI image for panel j, panel j) CDX-2.

Figure 27:
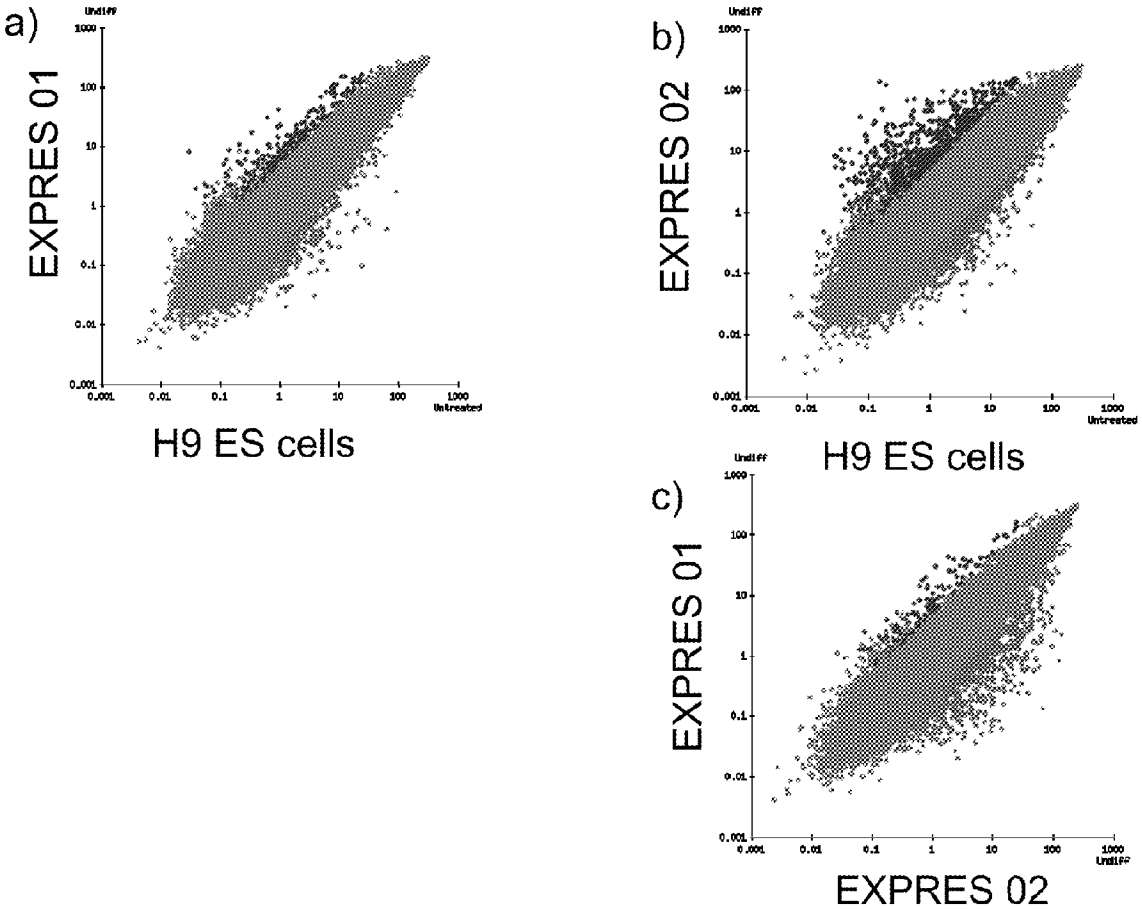
Figure 27:
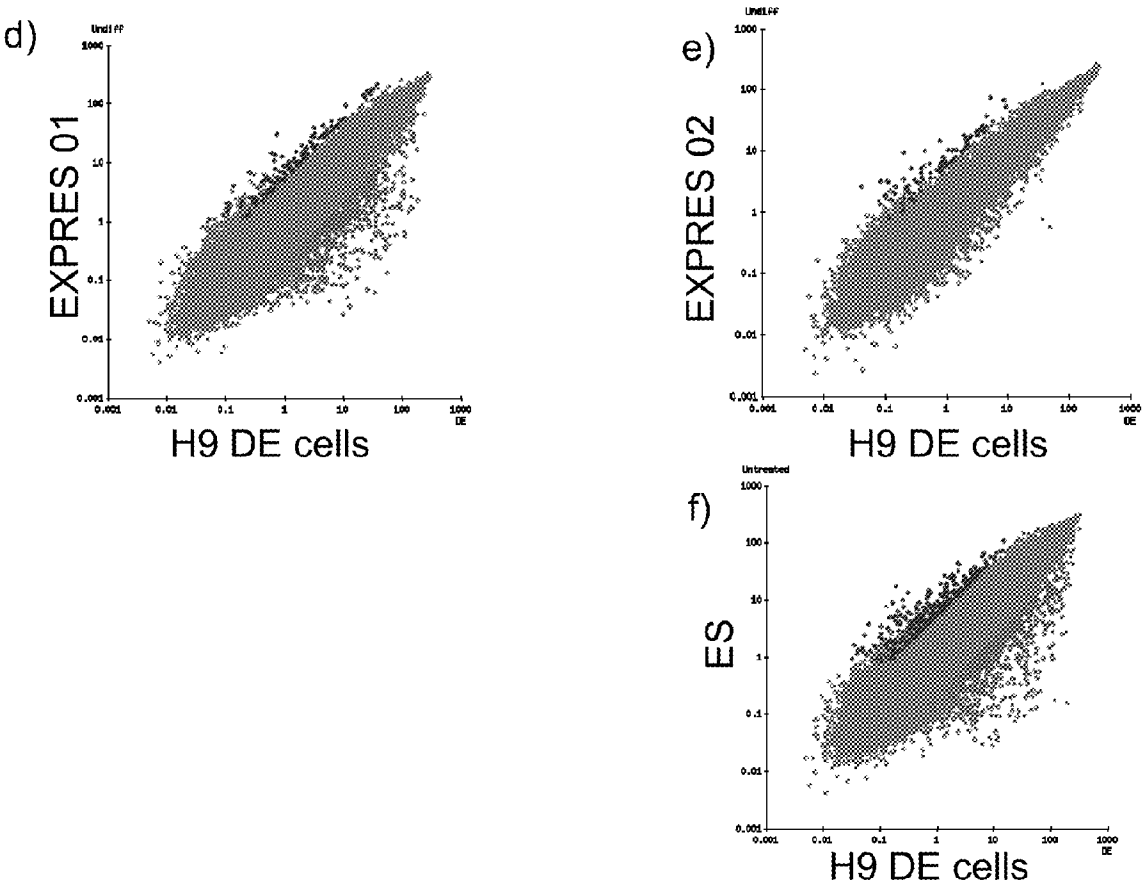

FIG. 27 shows scatter plots of microarray data comparing, panel a) EXPRES 01 cells (y-axis) to undifferentiated cells from the human embryonic stem cell line H9 (x-axis), panel b) EXPRES 02 cells (y-axis) to undifferentiated cells from the human embryonic stem cell line H9 (x-axis), panel c) EXPRES 01 cells (y-axis) to EXPRES 02 cells (x-axis), panel d) EXPRES 01 cells (y-axis) to cells from the human embryonic stem cell line H9 that have been differentiated into definitive endoderm (x-axis), panel e) EXPRES 02 cells (y-axis) to cells from the human embryonic stem cell line H9 that have been differentiated into definitive endoderm (x-axis), panel f) undifferentiated cells from the human embryonic stem cell line H9 (y-axis) to cells from the human embryonic stem cell line H9 that have been differentiated into definitive endoderm (x-axis).

Figure 28:
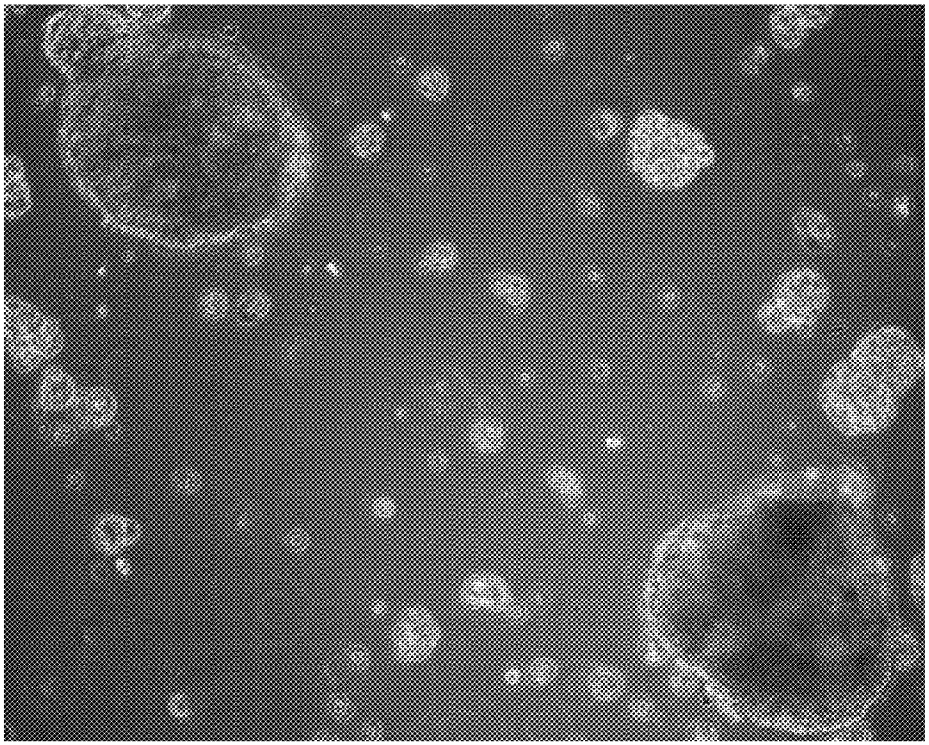

FIG. 28 shows the morphology of EB bodies formed by EXPRES 01 cells.

Figure 29:
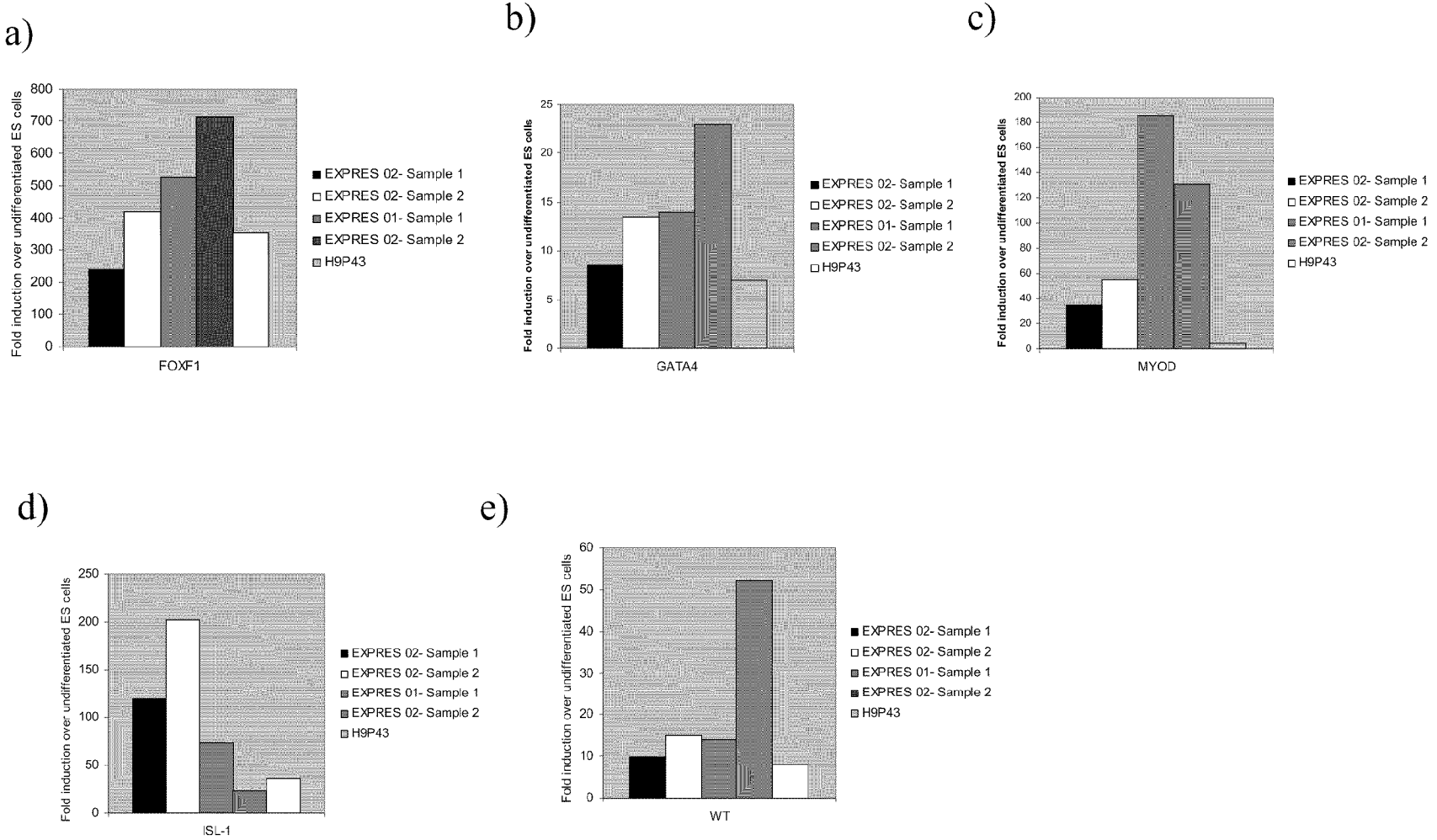
Figure 29:
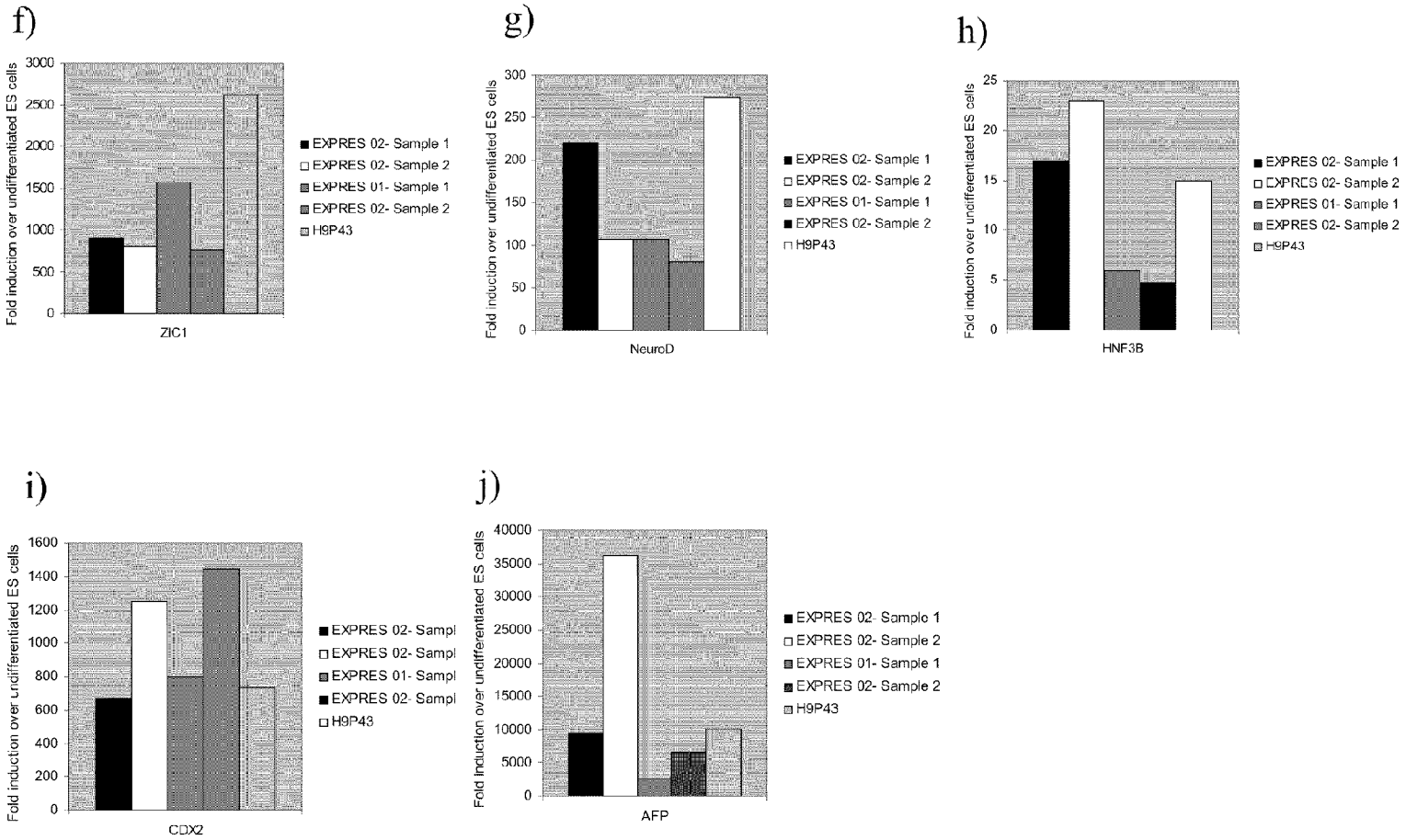
Figure 29:
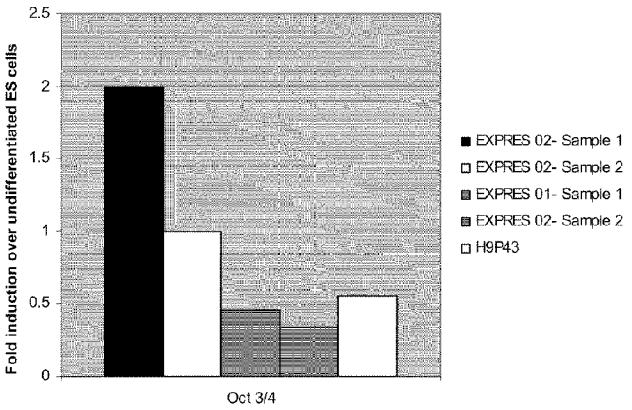
Figure 29:
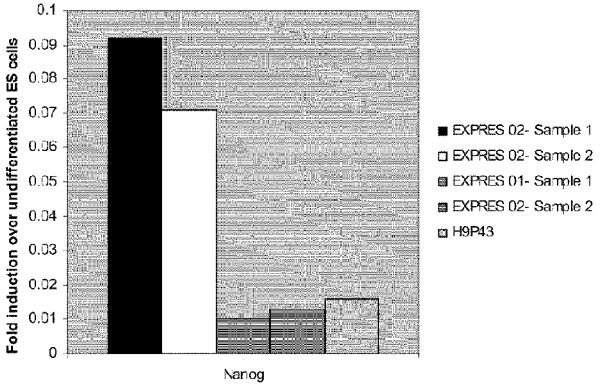
Figure 29:
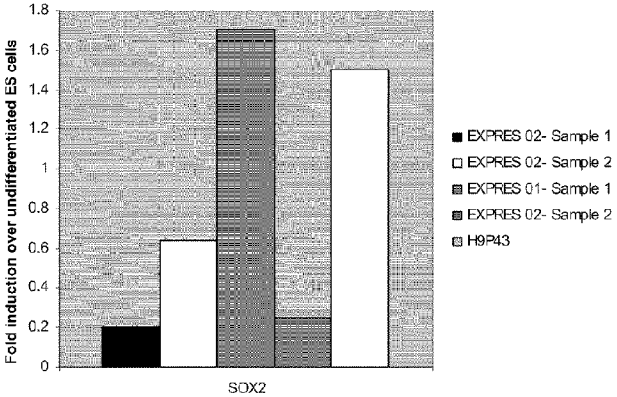

FIG. 29 shows gene expression as determined by real-time PCR for cells of the EXPRES 01 cell line, cells of the EXPRES 02 cell line, and cells from the human embryonic stem cell line H9 at passage 43, following five weeks of transplantation beneath the kidney capsule of NOD-SCID mice. Panels a-e, show mesoderm markers. Panels f & g show ectoderm markers. Panels h & i show endoderm markers. Panel j shows extra embryonic endoderm markers. Panels k-m show pluripotency markers.

Figure 30:
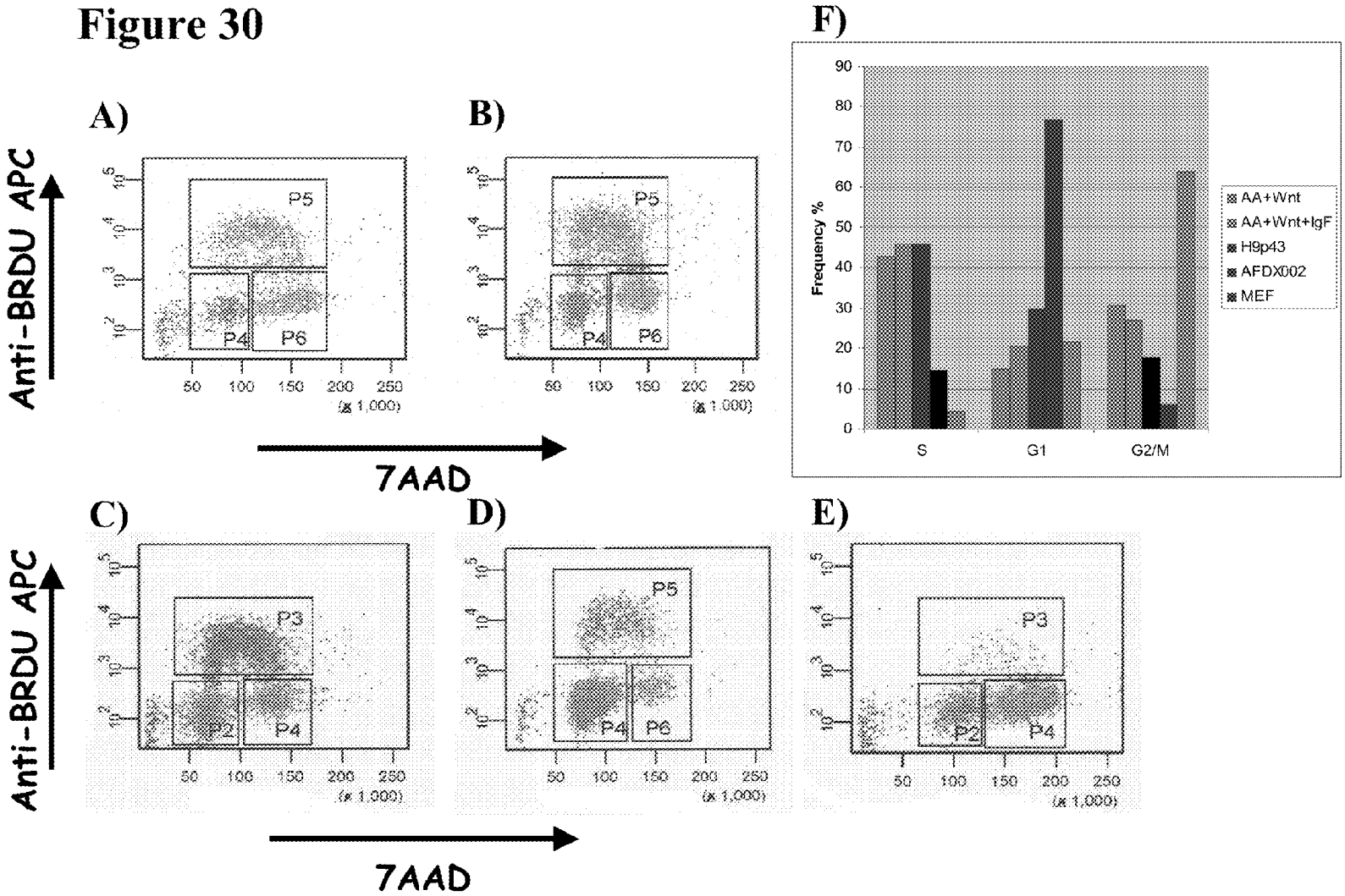

FIG. 30 shows the proliferation and cell cycle status of EXPRES 03 cells, as determined by BRDU incorporation. EXPRES 03 cells were cultured in 2% FBS/DMEM/F12, supplemented with, panel a) activin-A (100 ng/ml) and wnt3a (20 ng/ml), panel b) Activin-A (100 ng/ml) and wnt3a (20 ng/ml) and IGF (50 nh/ml). Other cells shown include, panel c) hES cells (H9p43), panel d) Amniotic Fluid Cells (AFDX002) and panel e) mitomycin treated MEF cells. Panel f) shows the frequency of cells in S-phase, G1 and G2/M-phases of cell cycle for different cell populations studied.

Figure 31:
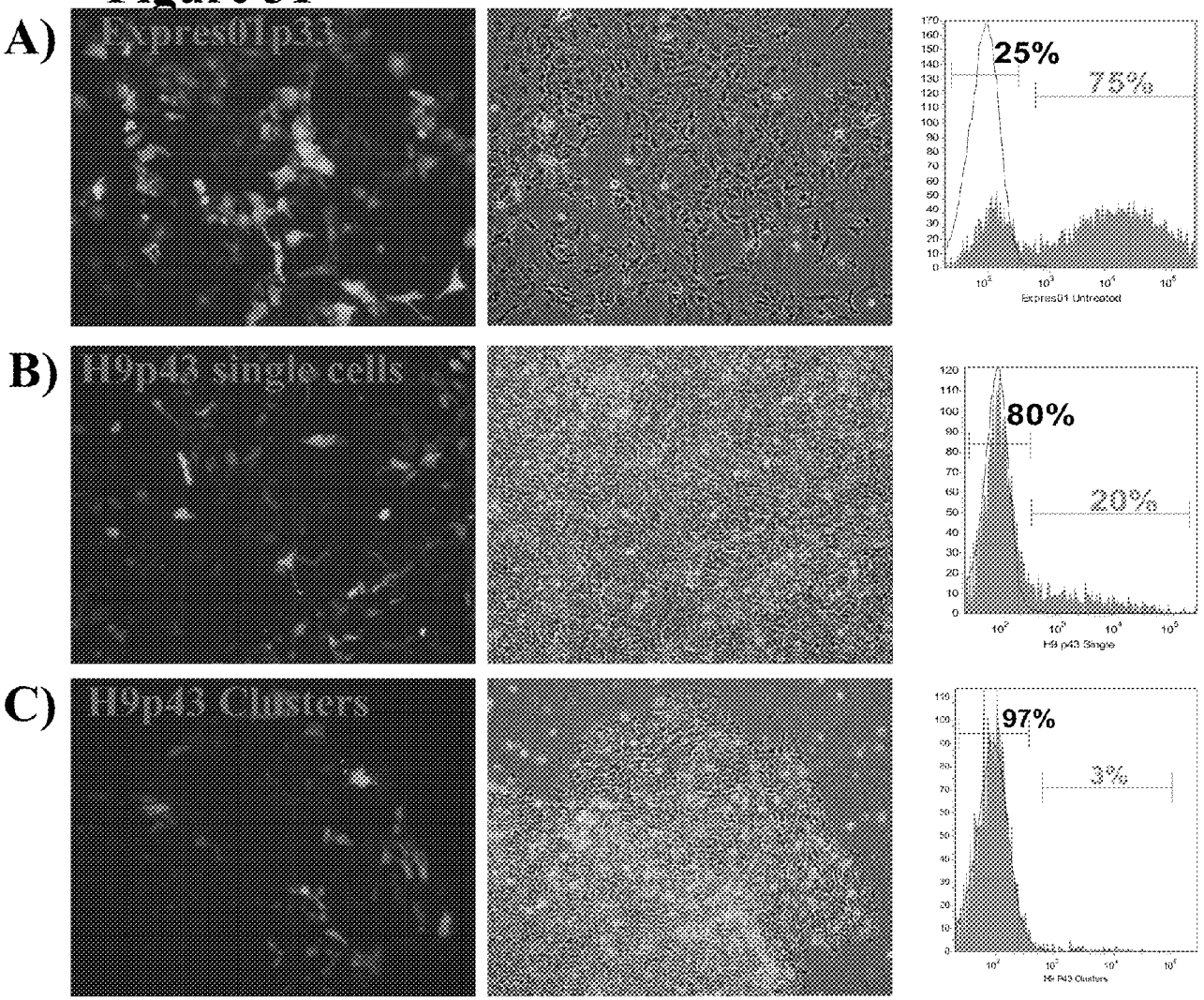

FIG. 31 shows the transfection efficiency and expression of EGFP in EXPRES 01 cells and human embryonic stem cells plated either as single cell dispersions or cell clusters. Cells were analyzed 24 hrs later by fluorescence microscopy and flow cytometry. Panel A) shows data obtained from EXPRES 01 cells. Panel B) shows data obtained from single cell dispersions of human embryonic stem cells and Panel C) shows data obtained from cell clusters of human embryonic stem cells.

Figure 32:
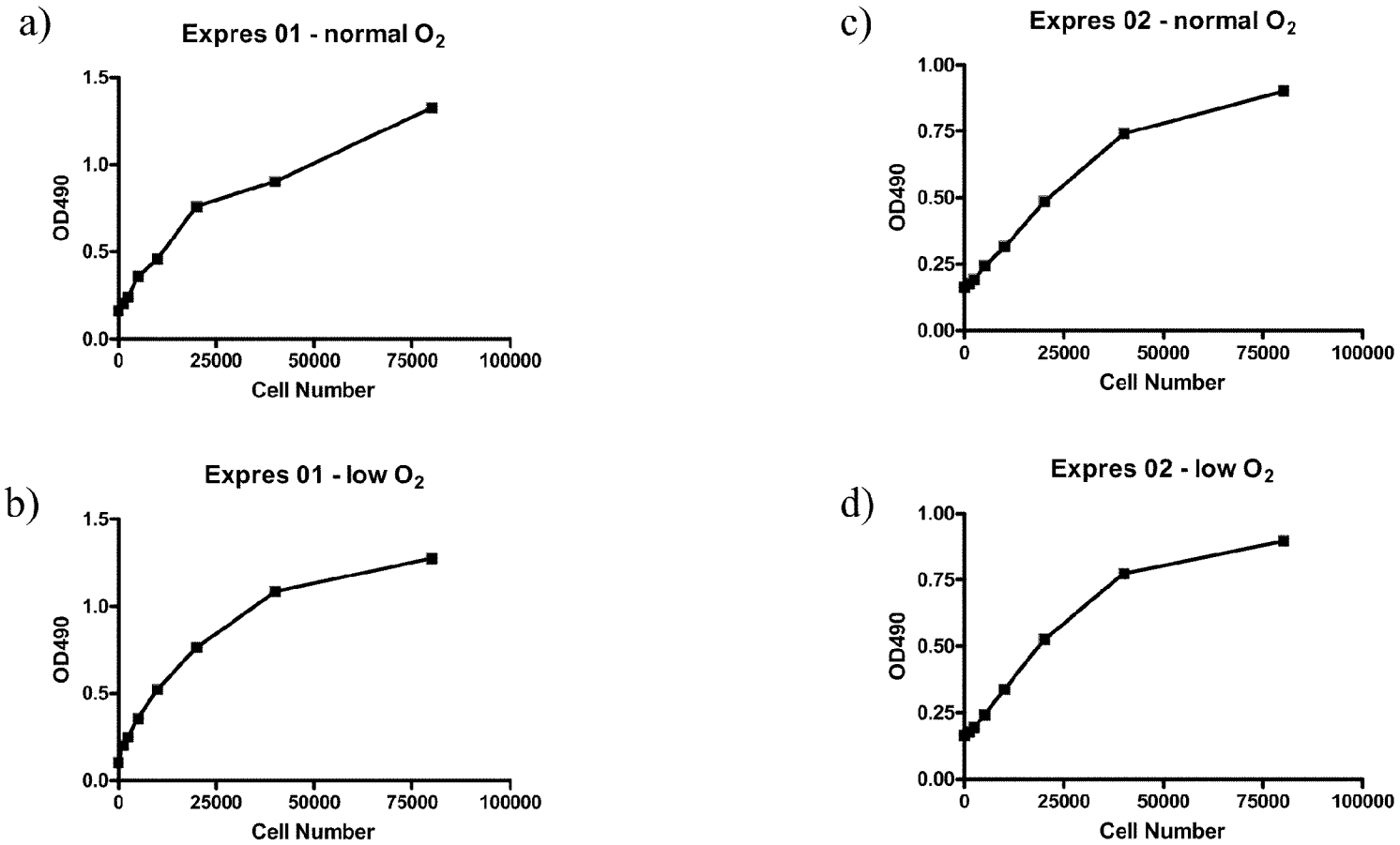

FIG. 32 shows average OD readings representing dehydrogenase enzyme activity versus cell number as measured by MTS assay for a) EXPRES 01 cells cultured in atmospheric oxygen (approximately 21%), b) EXPRES 01 cells cultured in 3% O2, c) EXPRES 02 cells cultured in atmospheric oxygen (approximately 21%), d) EXPRES 02 cells cultured in 3% O2 conditions.

Figure 33:
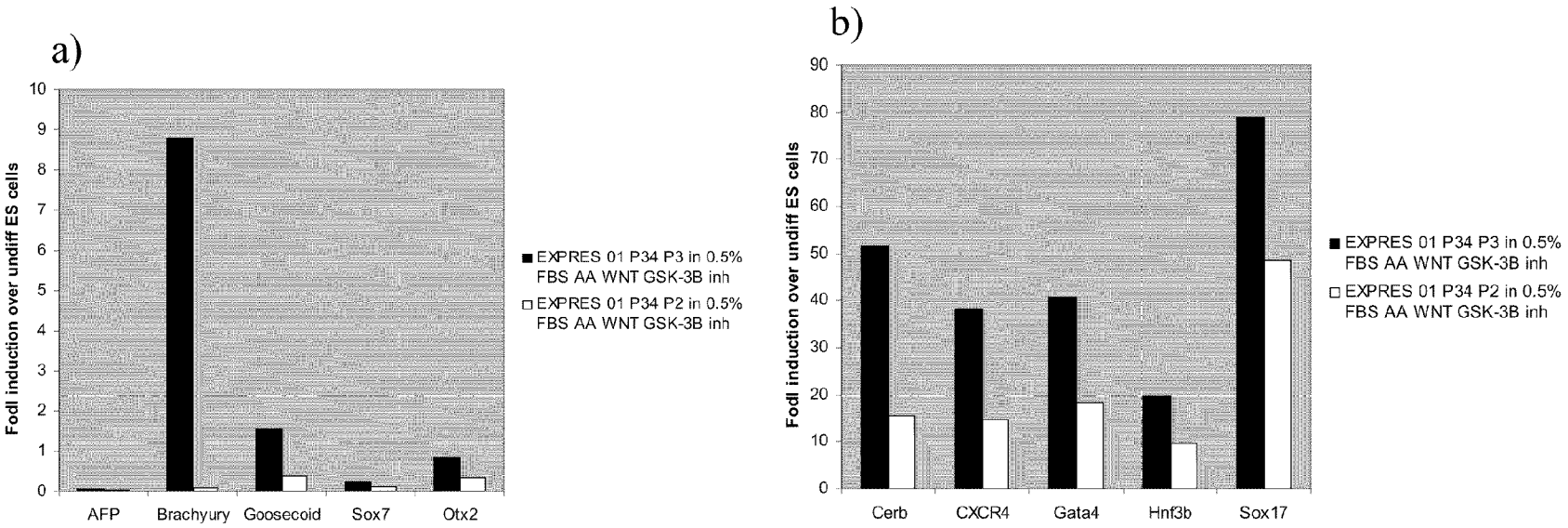

FIG. 33 shows gene expression as determined by real-time PCR for EXPRES 01 P27 cells seeded at 10000 cells/cm$^2$ on tissue culture polystyrene in DMEMF12+0.5% FBS+100 ng/ml AA+20 ng/ml WNT3A+100 nM GSK-3B inhibitor IX. Panel a depicts expression levels of AFP, Brachyury, SOX-7, and OTX2. Panel b depicts expression levels of CXCR4, HNF-3 beta, GATA-4, SOX-17, Cer1, and GSC.

Figure 34:
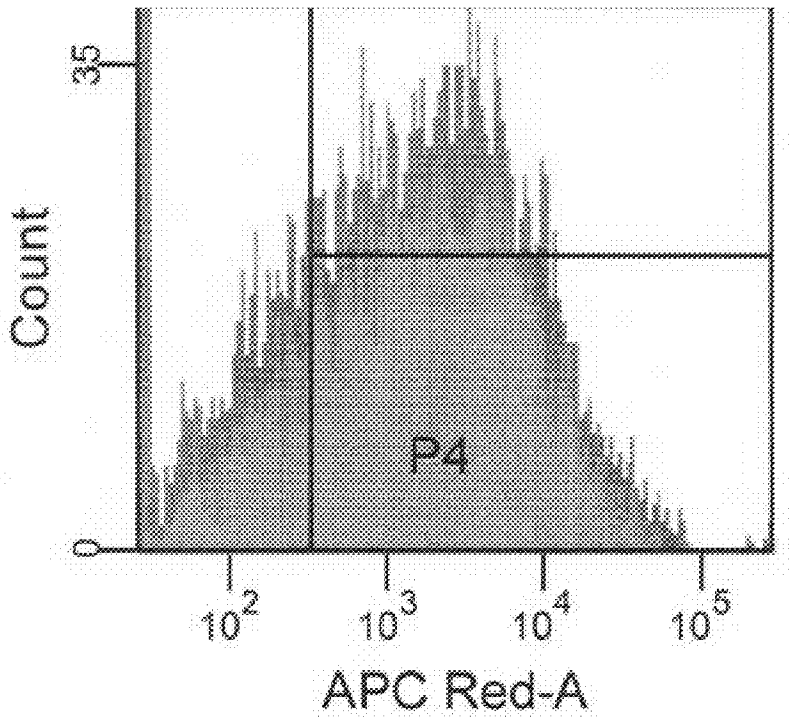

FIG. 34 shows protein expression of CXCR4 (Y-axis) and CD9 (x-axis), as determined by FACS for EXPRES 01 P27 cells cultured on tissue culture polystyrene in DMEM-F12+0.5% FBS+100 ng/ml AA+20 ng/ml WNT3A+100 nM GSK-3B inhibitor IX for three passages.

Figure 35:
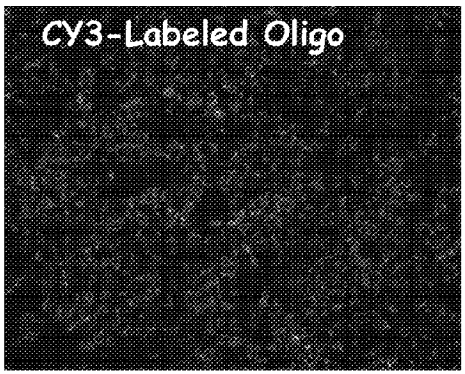
Figure 35:
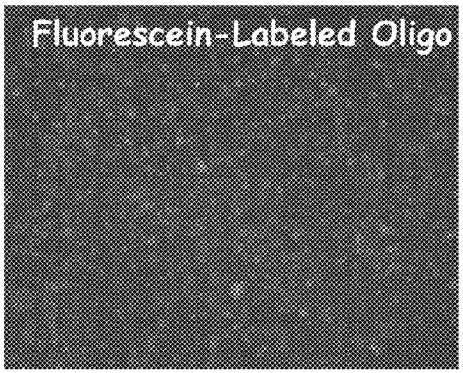
Figure 35:
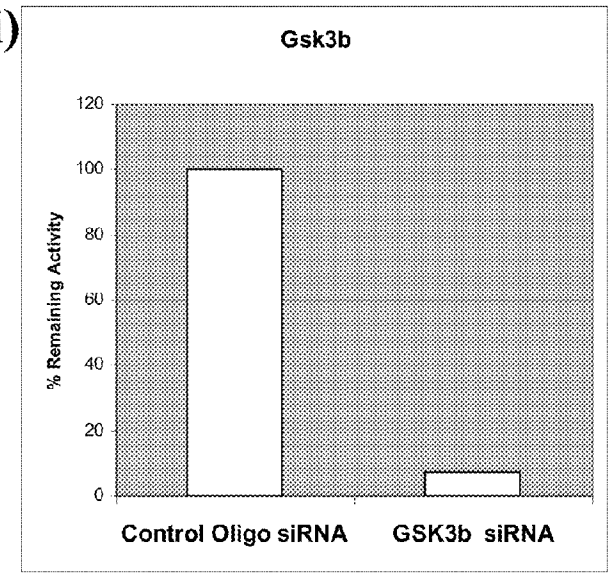
Figure 35:
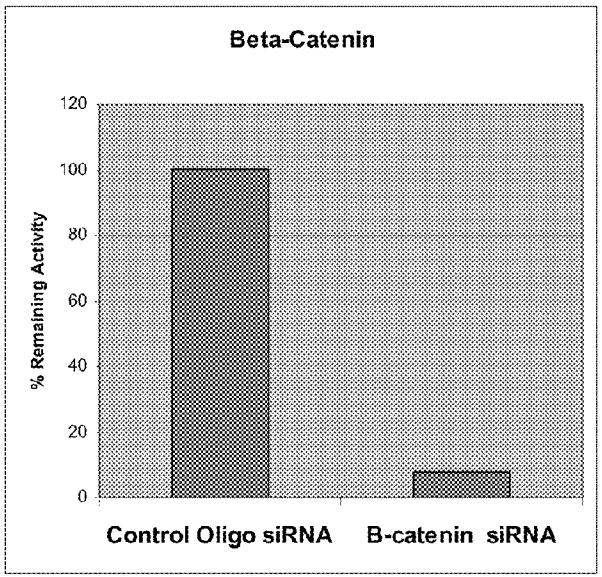

FIG. 35 shows the effects of siRNA transfection on the expression of GSK-3B and beta-catenin. EXPRES cells were analyzed by fluorescence microscopy and quantitative RT-PCR methods. A) Fluorescence microscopy of cells transfected with i) CY3 labeled siRNA and ii) Fluorescein labeled siRNA. B) Target gene knockdown expressed as % remaining activity in cells transfected with i) GSK3b and ii) Beta-catenin siRNA oligo sequences.

Figure 36:
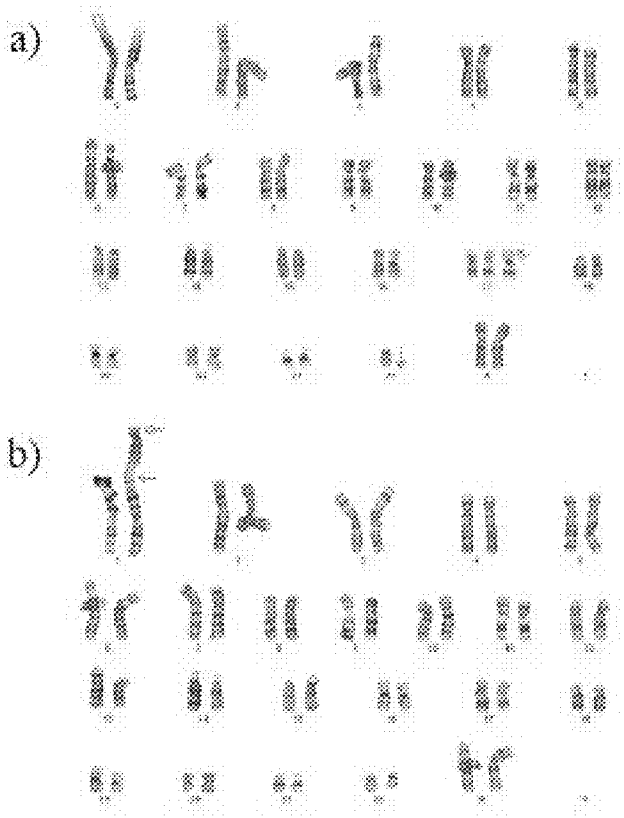

FIG. 36 shows the karyotype of two cell lines derived by methods of the present invention. Panel a: EXPRES 01 cell line. Panel b: EXPRES 02 cell line.

Figure 37:
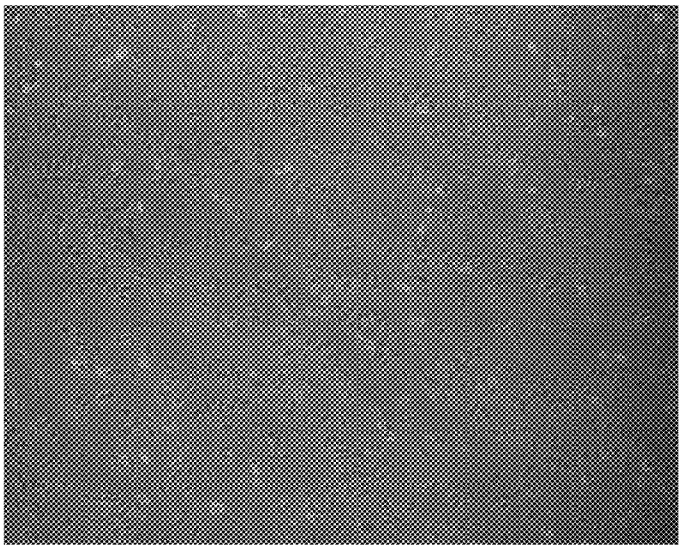
Figure 37:
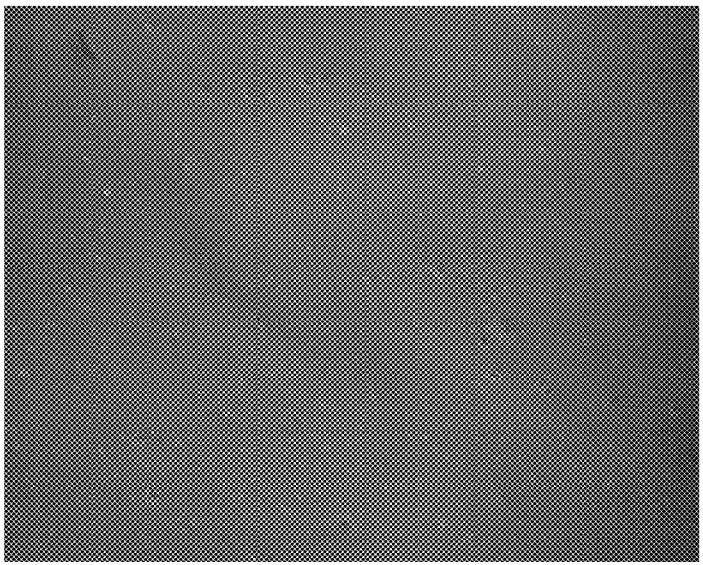

FIG. 37 shows the morphology of EXPRES 15 cells at passage 0 after 24 h culture in a) 2% FBS+DM-F12+100 ng/ml of activin-A+20 ng/ml of WNT-3A+50 ng/ml IGF or b) 2% FBS+DM-F12+100 ng/ml of Activin-A+20 ng/ml of WNT-3A+50 ng/ml IGF+10 μM of the Rho kinase inhibitor Y-27632.

Figure 38:
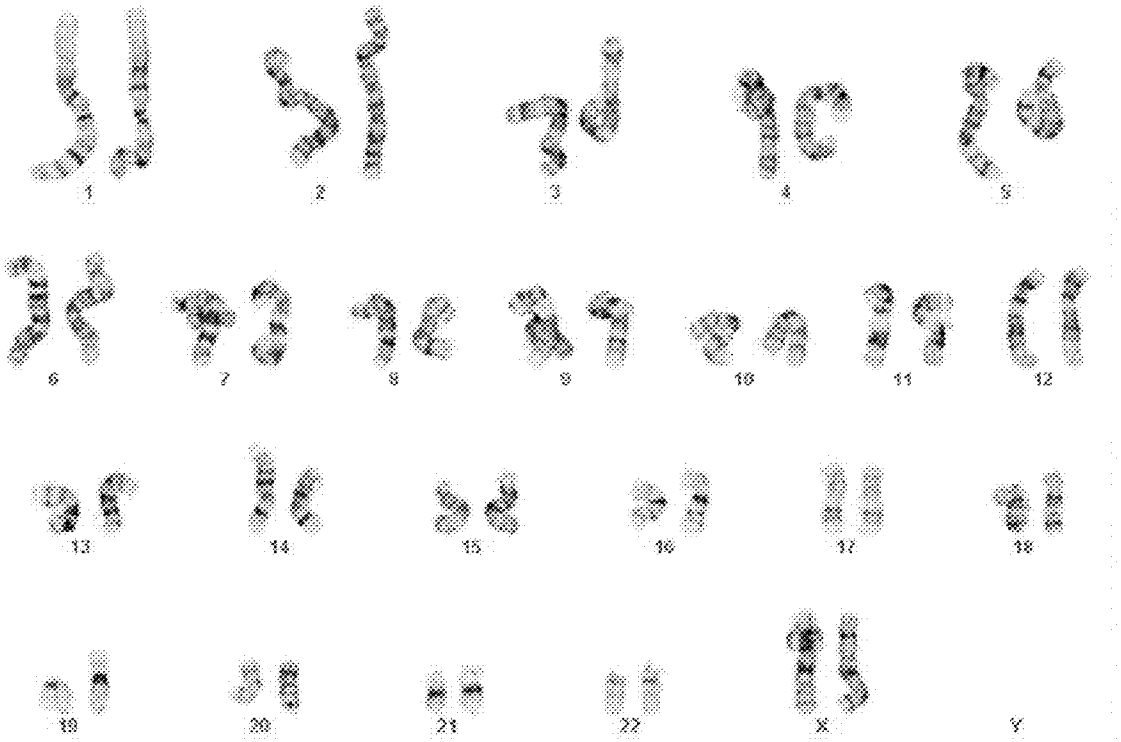

FIG. 38 shows the karyotype of EXPRES 15 cells cultured in 2% FBS+DM-F12+100 ng/ml of Activin-A+20 ng/ml of WNT-3A+50 ng/ml IGF+10 μM of the Rho kinase inhibitor Y-27632 for 12 passages.

Figure 39:
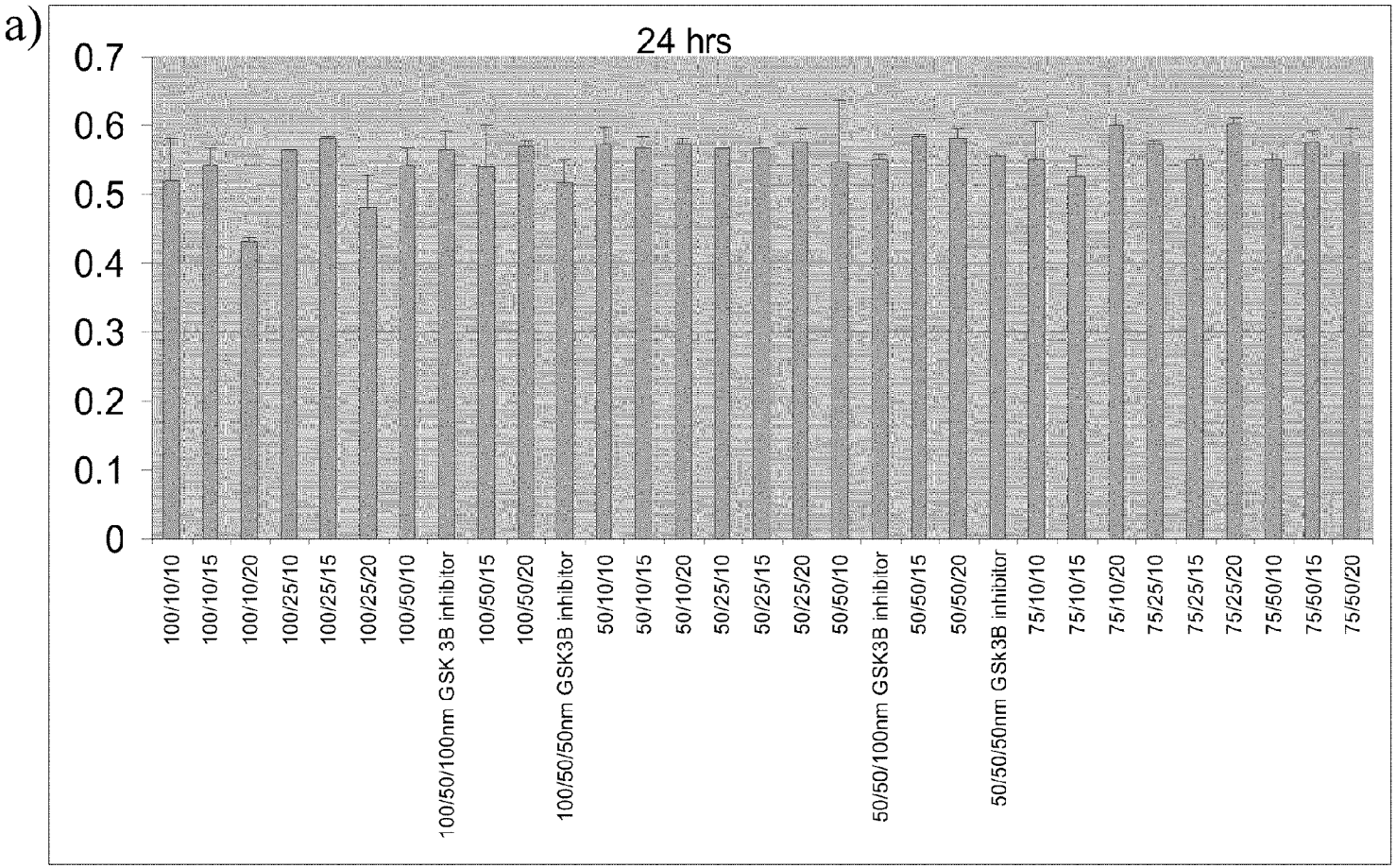
Figure 39:
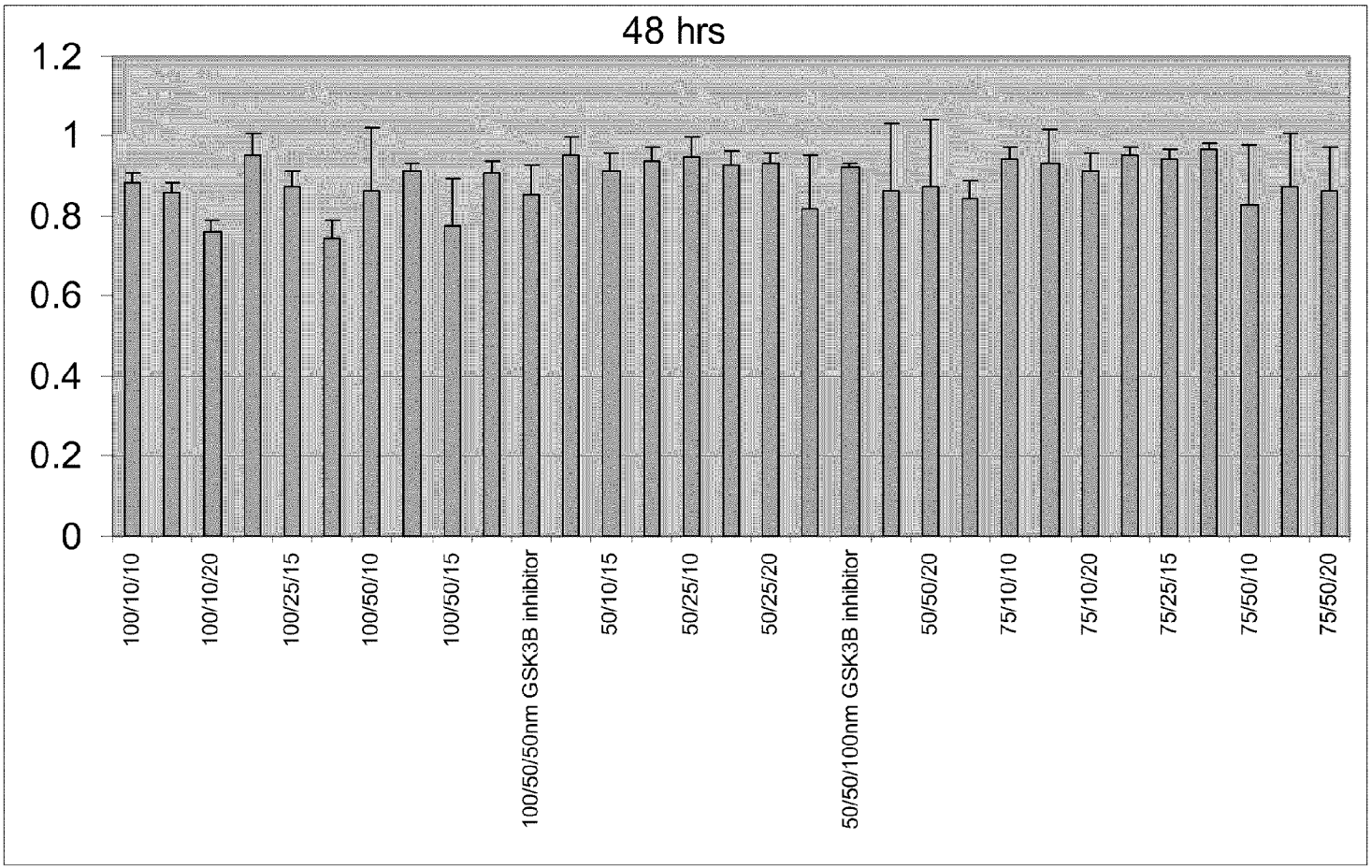
Figure 39:
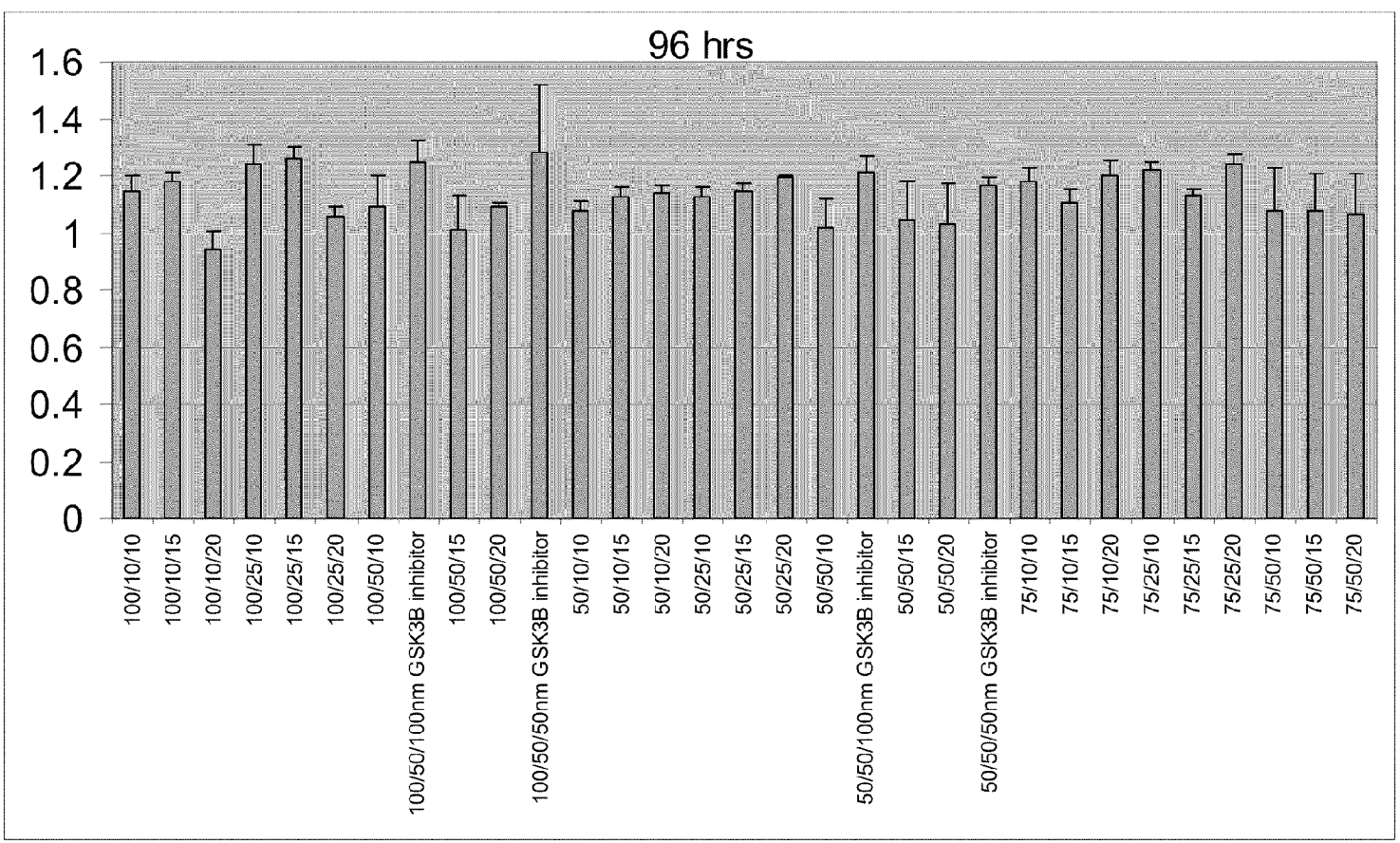

FIG. 39 shows the proliferation as determined by $A_{490}$ of EXPRES 11 cells cultured in basal media supplemented with IGF, activin-A, Wnt3A, and GSK inhibitor IX at the concentrations indicated at 24 h (panel a), 48 h (panel b), and 96 h (panel c).

DETAILED DESCRIPTION

For clarity of disclosure, and not by way of limitation, the detailed description of the invention is divided into the following subsections that describe or illustrate certain features, embodiments, or applications of the present invention.

DEFINITIONS

Stem cells are undifferentiated cells defined by their ability at the single cell level to both self-renew and differentiate to produce progeny cells, including self renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"AFP" or "alpha-fetoprotein protein" as used herein, refers to an antigen produced at the onset of liver development. AFP may also be expressed in extraembryonic cells.

"Albumin" is a soluble monomeric protein that makes up about half of all serum proteins in adults.

"β-cell lineage" refer to cells with positive gene expression for the transcription factor PDX-1 and at least one of the following transcription factors: NGN-3, NRx2.2, NRx6.1, NeuroD, Isl-1, HNF-3 beta, MAFA, Pax4, and Pax6. Cells expressing markers characteristic of the β cell lineage include β cells.

"Brachyury", as used herein, is a T-box gene family member. It is the marker for primitive streak and mesoderm cells.

"Cells expressing markers characteristic of the definitive endoderm lineage" as used herein refer to cells expressing at least one of the following markers: SOX-17, GATA-4, HNF-3 beta, GSC, Cer1, Nodal, FGF8, Brachyury, Mix-like homeobox protein, FGF4 CD48, eomesodermin (EOMES), DKK4, FGF17, GATA-6, CXCR4, C-Kit, CD99, or OTX2. Cells expressing markers characteristic of the definitive endoderm lineage include primitive streak precursor cells, primitive streak cells, mesendoderm cells and definitive endoderm cells.

"c-Kit" and "CD117" both refer to a cell surface receptor tyrosine kinase having a sequence disclosed in Genbank Accession No. X06182, or a naturally occurring variant sequence thereof (e.g., allelic variant).

"CD99" as used herein refers to the protein encoded by the gene with the accession number NM_002414.

"Cells expressing markers characteristic of the pancreatic endoderm lineage" as used herein refer to cells expressing at least one of the following markers: PDX-1, HNF-1beta, PTF-1 alpha, HNF-6, or HB9. Cells expressing markers characteristic of the pancreatic endoderm lineage include pancreatic endoderm cells.

"Cells expressing markers characteristic of the pancreatic endocrine lineage" as used herein refer to cells expressing at least one of the following markers: NGN-3, NeuroD, Islet-1, PDX-1, NKX6.1, Pax-4, Ngn-3, or PTF-1 alpha. Cells expressing markers characteristic of the pancreatic endocrine lineage include pancreatic endocrine cells, pancreatic hormone expressing cells, and pancreatic hormone secreting cells, and cells of the β-cell lineage.

"Cer1" or "Cerebrus" as used herein is a member of the cysteine knot superfamily of proteins.

"CXCR4" as used herein refers to the stromal cell-derived factor 1 (SDF-1) receptor, also known as "LESTR" or "fusin". In the gastrulating mouse embryo, CXCR4 is expressed in the definitive endoderm and mesoderm but not in extraembryonic endoderm.

"Definitive endoderm" as used herein refers to cells which bear the characteristics of cells arising from the epiblast during gastrulation and which form the gastrointestinal tract and its derivatives. Definitive endoderm cells express the following markers: HNF-3 beta, GATA-4, SOX-17, Cerberus, OTX2, goosecoid, C-Kit, CD99, and Mixl1.

"Extraembryonic endoderm" as used herein refers to a population of cells expressing at least one of the following markers: SOX-7, AFP, and SPARC.

"FGF-2", "FGF-4" "FGF-8" "FGF-10", and "FGF-17" as used herein, are members of the fibroblast growth factor family.

"GATA-4" and "GATA-6" are members of the GATA transcription factor family. This family of transcription factors is induced by TGF-β signaling, and contribute to the maintenance of early endoderm markers.

"GLUT-2", as used herein, refers to the glucose transporter molecule that is expressed in numerous fetal and adult tissues, including pancreas, liver, intestine, brain, and kidney.

"Goosecoid" or "GSC" as used herein, refers to a homeodomain transcription factor expressed in the dorsal lip of the blastopore.

"HB9" as used herein, refers to the homeobox gene 9.

"HNF-1 alpha", "HNF-1 beta", "HNF-3 beta", and "HNF-6" belong to the hepatic nuclear factor family of transcription factors, which is characterized by a highly conserved DNA binding domain and two short carboxy-terminal domains.

"Islet-1" or "Isl-1" as used herein is a member of the LIM/homeodomain family of transcription factors, and is expressed in the developing pancreas.

"MafA" as used herein is a transcription factor expressed in the pancreas, and controls the expression of genes involved in insulin biosynthesis and secretion.

"Markers" as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Mesendoderm cell" as used herein refers to a cell expressing at least one of the following markers: CD48, eomesodermin (EOMES), SOX-17, DKK4, HNF-3 beta, GSC, FGF17, GATA-6.

"Mixl1" as used herein refers to a homeobox gene, which is marker for the cells in the primitive streak, mesoderm, and endoderm.

"NeuroD" as used herein is basic helix-loop-helix (bHLH) transcription factor implicated in neurogenesis.

"NGN-3" as used herein, is a member of the neurogenin family of basic loophelix-loop transcription factors.

"Nkx-2.2" and "Nkx-6.1" as used herein are members of the Nkx transcription factor family.

"Nodal" as used herein, is a member of the TGF beta superfamily of proteins.

"Oct-4" is a member of the POU-domain transcription factor and is widely regarded as a hallmark of pluripotent stem cells. The relationship of Oct-4 to pluripotent stem cells is indicated by its tightly restricted expression to undifferentiated pluripotent stem cells. Upon differentiation to somatic lineages, the expression of Oct-4 disappears rapidly.

"Pancreatic endocrine cell", or "pancreatic hormone expressing cell" as used herein refers to a cell capable of expressing at least one of the following hormones: insulin, glucagon, somatostatin, and pancreatic polypeptide.

"Pancreatic hormone secreting cell" as used herein refers to a cell capable of secreting at least one of the following hormones: insulin, glucagon, somatostatin, and pancreatic polypeptide.

"Pax-4" and "Pax-6" as used herein are pancreatic P cell specific transcription factors that are implicated in islet development.

"PDX-1" as used herein refers to a homeodomain transcription factor implicated in pancreas development.

"Pre-primitive streak cell" as used herein refers to a cell expressing at least one of the following markers: Nodal, or FGF8

"Primitive streak cell" as used herein refers to a cell expressing at least one of the following markers: Brachyury, Mix-like homeobox protein, or FGF4.

"PTF-1 alpha" as used herein refers to a basic helix-loop-helix protein of 48 kD that is a sequence-specific DNA-binding subunit of the trimeric pancreas transcription factor-1 (PTF1).

"SOX-1", "SOX-2", "SOX-7", and "SOX-17" as used herein, are a members of the SOX transcription factor family, and are implicated in embryogenesis.

"SPARC" as used herein is also known as "secreted protein acidic and rich in cysteine".

"SSEA-1" (Stage Specific Embryonic Antigen-1) is a glycolipid surface antigen present on the surface of murine teratocarcinoma stem cells (EC), murine and human embryonic germ cells (EG), and murine embryonic stem cells (ES).

"SSEA-3" (Stage Specific Embryonic Antigen-3) is a glycolipid surface antigen present on the surface of human teratocarcinoma stem cells (EC), human embryonic germ cells (EG), and human embryonic stem cells (ES).

"SSEA-4" (Stage Specific Embryonic Antigen-4) is a glycolipid surface antigen present on the surface of human teratocarcinoma stem cells (EC), human embryonic germ cells (EG), and human embryonic stem cells (ES).

"TRA1-60" is a keratin sulfate related antigen that is expressed on the surface of human teratocarcinoma stem cells (EC), human embryonic germ cells (EG), and human embryonic stem cells (ES).

"TRA1-81" is a keratin sulfate related antigen that is expressed on the surface of human teratocarcinoma stem cells (EC), human embryonic germ cells (EG), and human embryonic stem cells (ES).

"TRA2-49" is an alkaline phosphatase isozyme expressed on the surface of human teratocarcinoma stem cells (EC) and human embryonic stem cells (ES).

"UTF-1" as used herein, refers a transcriptional co-activator expressed in pluripotent embryonic stem cells and extra-embryonic cells.

"Zic1" as used herein is a member of the Zic transcription factor family. Zic1 regulates the expression of neural and neural crest-specific genes and is expressed in the cells of the dorsal neural tube and the premigratory neural crest.

Method to Derive Cells Expressing Pluripotency Markers

The present invention provides a cell population with characteristics of human embryonic stem cells, that can be readily expanded in culture, in low serum, that requires no feeder cell line or a coating of complex matrix proteins, can be passaged in single cell suspension, can be transfected with a very high efficiency, and cultured under hypoxic conditions. This combination of unique attributes separates the cells described in the present invention from the prior art.

In one embodiment, the present invention provides a method for deriving a population of cells comprising cells expressing pluripotency markers, comprising the steps of:

a. Obtaining cells, and
b. Culturing the cells under hypoxic conditions, on a tissue culture substrate that is not pre-treated with a protein or an extracellular matrix prior to culturing the cells.

The cells may be human embryonic stem cells, or they may be cells expressing markers characteristic of the definitive endoderm lineage. The human embryonic stem cells may be cultured in normoxic conditions prior to culturing the cells on a tissue culture substrate that is not pre-treated with a protein or an extracellular matrix. Alternatively, the human embryonic stem cells may be cultured in hypoxic conditions.

The cells expressing markers characteristic of the definitive endoderm lineage may be cultured in normoxic conditions prior to culturing the cells on a tissue culture substrate that is not pre-treated with a protein or an extracellular matrix. Alternatively, the cells expressing markers characteristic of the definitive endoderm lineage may be cultured in hypoxic conditions.

In one embodiment, the present invention provides a method for deriving a population of cells comprising cells expressing pluripotency markers, comprising the steps of:

a. Culturing human embryonic stem cells,
b. Differentiating the human embryonic stem cells into cells expressing markers characteristic of definitive endoderm cells, and
c. Removing the cells, and subsequently culturing them under hypoxic conditions, on a tissue culture substrate that is not pre-treated with a protein or an extracellular matrix prior to culturing the cells.

In one embodiment, the present invention provides a method for deriving a population of cells comprising cells expressing pluripotency markers, comprising the steps of:

a. Culturing human embryonic stem cells, and
b. Removing the cells, and subsequently culturing them under hypoxic conditions, on a tissue culture substrate that is not pre-treated with a protein or an extracellular matrix.

Cell Culture Under Hypoxic Conditions on a Tissue Culture Substrate that is not Pre-Treated with a Protein or an Extracellular Matrix In one embodiment, the cells are cultured under hypoxic conditions, on a tissue culture substrate that is not coated with an extracellular matrix for about 1 to about 20 days. In an alternate embodiment, the cells are cultured under hypoxic conditions, on a tissue culture substrate that is not coated with an extracellular matrix for about 5 to about 20 days. In an alternate embodiment, the cells are cultured under hypoxic conditions, on a tissue culture substrate that is not coated with an extracellular matrix for about 15 days.

In one embodiment, the hypoxic condition is about 1% $O_2$ to about 20% $O_2$. In an alternate embodiment, the hypoxic condition is about 2% $O_2$ to about 10% $O_2$. In an alternate embodiment, the hypoxic condition is about 3% $O_2$.

The cells may be cultured, under hypoxic conditions on a tissue culture substrate that is not pre-treated with a protein or an extracellular matrix, in medium containing serum, activin-A, and a Wnt ligand. Alternatively, the medium may also contain IGF-1.

The culture medium may have a serum concentration in the range of about 2% to about 5%. In an alternate embodiment, the serum concentration may be about 2%.

Activin-A may be used at a concentration from about 1 pg/ml to about 100 μg/ml. In an alternate embodiment, the concentration may be about 1 pg/ml to about 1 μg/ml. In another alternate embodiment, the concentration may be about 1 pg/ml to about 100 ng/ml. In another alternate embodiment, the concentration may be about 50 ng/ml to about 100 ng/ml. In another alternate embodiment, the concentration may be about 100 ng/ml.

The Wnt ligand may be selected from the group consisting of Wnt-1, Wnt-3a, Wnt-5a and Wnt-7a. In one embodiment, the Wnt ligand is Wnt-1. In an alternate embodiment, the Wnt ligand is Wnt-3a.

The Wnt ligand may be used at a concentration of about 1 ng/ml to about 1000 ng/ml. In an alternate embodiment, the Wnt ligand may be used at a concentration of about 10 ng/ml to about 100 ng/ml. In one embodiment, the concentration of the Wnt ligand is about 20 ng/ml.

IGF-1 may be used at a concentration of about 1 ng/ml to about 100 ng/ml. In an alternate embodiment, the IGF-1 may be used at a concentration of about 10 ng/ml to about 100 ng/ml. In one embodiment, the concentration of IGF-1 is about 50 ng/ml.

The cells expressing pluripotency markers derived by the methods of the present invention are capable of expansion in culture under hypoxic conditions, on tissue culture substrate that is not pre-treated with a protein or an extracellular matrix.

The cells expressing pluripotency markers derived by the methods of the present invention express at least one of the following pluripotency markers selected from the group consisting of: ABCG2, cripto, FoxD3, Connexin43, Connexin45, Oct4, SOX-2, Nanog, hTERT, UTF-1, ZFP42, SSEA-3, SSEA-4, Tra1-60, and Tra1-81.

In one embodiment, the cells expressing pluripotency markers derived by the methods of the present invention are capable of expressing markers characteristic of pre-primitive streak cells.

In one embodiment, the cells expressing pluripotency markers derived by the methods of the present invention are capable of expressing markers characteristic of primitive streak cells.

In one embodiment, the cells expressing pluripotency markers derived by the methods of the present invention are capable of expressing markers characteristic of mesendoderm cells.

In one embodiment, the cells expressing pluripotency markers derived by the methods of the present invention are capable of expressing markers characteristic of definitive endoderm cells.

Further Differentiation of Cells Expressing Pluripotency Markers Derived by the Methods of the Present Invention Cells expressing pluripotency markers derived by the methods of the present invention may be differentiated into cells expressing markers characteristic of the definitive endoderm lineage by any method in the art.

For example, cells expressing pluripotency markers derived by the methods of the present invention may be differentiated into cells expressing markers characteristic of the definitive endoderm lineage according to the methods disclosed in D'Amour et al, Nature Biotechnology 23, 1534-1541 (2005).

For example, cells expressing pluripotency markers derived by the methods of the present invention may be differentiated into cells expressing markers characteristic of the definitive endoderm lineage according to the methods disclosed in Shinozaki et al, Development 131, 1651-1662 (2004).

For example, cells expressing pluripotency markers derived by the methods of the present invention may be differentiated into cells expressing markers characteristic of the definitive endoderm lineage according to the methods disclosed in McLean et al., Stem Cells 25, 29-38 (2007).

For example, cells expressing pluripotency markers derived by the methods of the present invention may be differentiated into cells expressing markers characteristic of the definitive endoderm lineage according to the methods disclosed in D'Amour et al., Nature Biotechnology 24, 1392-1401 (2006).

For example, cells expressing pluripotency markers derived by the methods of the present invention may be differentiated into cells expressing markers characteristic of the definitive endoderm lineage by culturing the pluripotent stem cells in medium containing activin-A in the absence of serum, then culturing the cells with activin-A and serum, and then culturing the cells with activin-A and serum of a different concentration. An example of this method is disclosed in D'Amour et al., Nature Biotechnology, 23, 1534-1541, 2005.

Further Differentiation of Cells Expressing Markers Characteristic of the Definitive Endoderm Lineage Cells expressing markers characteristic of the definitive endoderm lineage may be differentiated into cells expressing markers characteristic of the pancreatic endoderm lineage by any method in the art.

For example, cells expressing markers characteristic of the definitive endoderm lineage may be differentiated into cells expressing markers characteristic of the pancreatic endoderm lineage according to the methods disclosed in D'Amour et al, Nature Biotechnology 24, 1392-1401 (2006).

For example, cells expressing markers characteristic of the definitive endoderm lineage are further differentiated into cells expressing markers characteristic of the pancreatic endoderm lineage, by treating the cells expressing markers characteristic of the definitive endoderm lineage with a fibroblast growth factor and KAAD-cyclopamine, then removing the medium containing the fibroblast growth factor and KAAD-cyclopamine and subsequently culturing the cells in medium containing retinoic acid, a fibroblast growth factor and KAAD-cyclopamine. An example of this method is disclosed in D'Amour et al, Nature Biotechnology, 24: 1392-1401, (2006).

Further Differentiation of Cells Expressing Markers Characteristic of the Pancreatic Endoderm Lineage Cells expressing markers characteristic of the pancreatic endoderm lineage may be differentiated into cells expressing markers characteristic of the pancreatic endocrine lineage by any method in the art.

For example, cells expressing markers characteristic of the pancreatic endoderm lineage may be differentiated into cells expressing markers characteristic of the pancreatic endocrine lineage according to the methods disclosed in D'Amour et al, Nature Biotechnology 24, 1392-1401 (2006).

Without being subject to limitation, the following sections contain examples of methods to obtain cells that are suitable starting materials for forming cells expressing pluripotency markers and markers characteristic of the definitive endoderm lineage according to the methods of the present invention.

Isolation, Expansion and Culture of Human Embryonic Stem Cells

Characterization of human embryonic stem cells: Human embryonic stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of human embryonic stem cells in vitro results in the loss of SSEA-4, Tra-1-60, and Tra-1-81 expression (if present) and increased expression of SSEA-1. Undifferentiated human embryonic stem cells typically have alkaline phosphatase activity, which can be detected by fixing the cells with 4% paraformaldehyde, and then developing with Vector Red as a substrate, as described by the manufacturer (Vector Laboratories, Burlingame Calif.). Undifferentiated pluripotent stem cells also typically express Oct-4 and TERT, as detected by RT-PCR.

Another desirable phenotype of propagated human embryonic stem cells is a potential to differentiate into cells of all three germinal layers: endoderm, mesoderm, and ectoderm tissues. Pluripotency of human embryonic stem cells can be confirmed, for example, by injecting cells into SCID mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated human embryonic stem cell lines may be karyotyped using a standard G-banding technique and compared to published karyotypes of the corresponding primate species. It is desirable to obtain cells that have a "normal karyotype", which means that the cells are euploid, wherein all human chromosomes are present and not noticeably altered.

Sources of human embryonic stem cells: Types of human embryonic stem cells that may be used include established lines of human embryonic cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.).

In one embodiment, Human embryonic stem cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

Culture of human embryonic stem cells: In one embodiment, human embryonic stem cells are cultured in a culture system that is essentially free of feeder cells, but nonetheless supports proliferation of human embryonic stem cells without undergoing substantial differentiation. The growth of human embryonic stem cells in feeder-free culture without differentiation is supported using a medium conditioned by culturing previously with another cell type. Alternatively, the growth of human embryonic stem cells in feeder-free culture without differentiation is supported using a chemically defined medium.

In an alternate embodiment, human embryonic stem cells are initially cultured layer of feeder cells that support the human embryonic stem cells in various ways. The human embryonic are then transferred to a culture system that is essentially free of feeder cells, but nonetheless supports proliferation of human embryonic stem cells without undergoing substantial differentiation.

Examples of conditioned media suitable for use in the present invention are disclosed in US20020072117, U.S. Pat. No. 6,642,048, WO2005014799, and Xu et al (Stem Cells 22: 972-980, 2004).

An example of a chemically defined medium suitable for use in the present invention may be found in US20070010011.

Suitable culture media may be made from the following components, such as, for example, Dulbecco's modified Eagle's medium (DMEM), Gibco # 11965-092; Knockout Dulbecco's modified Eagle's medium (KO DMEM), Gibco # 10829-018; Ham's F12/50% DMEM basal medium; 200 mM L-glutamine, Gibco #15039-027; non-essential amino acid solution, Gibco 11140-050; β-mercaptoethanol, Sigma # M7522; human recombinant basic fibroblast growth factor (bFGF), Gibco # 13256-029.

In one embodiment, the human embryonic stem cells are plated onto a suitable culture substrate that is treated prior to treatment according to the methods of the present invention. In one embodiment, the treatment is an extracellular matrix component, such as, for example, those derived from basement membrane or that may form part of adhesion molecule receptor-ligand couplings. In one embodiment, the suitable culture substrate is MATRIGEL (Becton Dickenson). MATRIGEL is a soluble preparation from Engelbreth-Holm-Swarm tumor cells that gels at room temperature to form a reconstituted basement membrane.

Other extracellular matrix components and component mixtures are suitable as an alternative. This may include laminin, fibronectin, proteoglycan, entactin, heparan sulfate, and the like, alone or in various combinations.

The human embryonic stem cells are plated onto the substrate in a suitable distribution and in the presence of a medium that promotes cell survival, propagation, and retention of the desirable characteristics. All these characteristics benefit from careful attention to the seeding distribution and can readily be determined by one of skill in the art.

The human embryonic stem cells are then removed from the treated tissue culture substrate and plated onto a non-treated tissue culture substrate, prior to treatment according to the methods of the present invention to form cells expressing pluripotency markers and markers characteristic of the definitive endoderm lineage.

Differentiation of Human Embryonic Stem Cells into Cells Expressing Markers Characteristic of the Definitive Endoderm Lineage Human embryonic stem cells may be differentiated into cells expressing markers characteristic of the definitive endoderm lineage by any method in the art. The cells expressing markers characteristic of the definitive endoderm lineage are suitable for treating according to the methods of the present invention.

For example, human embryonic stem cells may be differentiated into cells expressing markers characteristic of the definitive endoderm lineage according to the methods disclosed in D'Amour et al., Nature Biotechnology 23, 1534-1541 (2005).

For example, human embryonic stem cells may be differentiated into cells expressing markers characteristic of the definitive endoderm lineage according to the methods disclosed in Shinozaki et al, Development 131, 1651-1662 (2004).

For example, human embryonic stem cells may be differentiated into cells expressing markers characteristic of the definitive endoderm lineage according to the methods disclosed in McLean et al, Stem Cells 25, 29-38 (2007).

Differentiation of Human Embryonic Stem Cells Cultured on an Extracellular Matrix into Cells Expressing Markers Characteristic of the Definitive Endoderm Lineage In one embodiment, the present invention provides a method for differentiating human embryonic stem cells expressing markers characteristic of the definitive endoderm lineage, comprising the steps of:

a. Plating the human embryonic stem cells on a tissue culture substrate coated with an extracellular matrix, and
b. Culturing the human embryonic stem cells with activin-A and a Wnt ligand.

The cells expressing markers characteristic of the definitive endoderm lineage are then subsequently treated by the methods of the present invention to form cells expressing pluripotency markers and markers characteristic of the definitive endoderm lineage.

Culturing the human embryonic stem cells with activin-A and a Wnt ligand may be performed in a single culture medium. Alternatively, culturing the human embryonic stem cells with activin-A and a Wnt ligand may be performed in more than one culture media. In one embodiment, culturing the human embryonic stem cells with activin-A and a Wnt ligand is performed in two culture media.

Extracellular Matrix In one aspect of the present invention, the human embryonic stem cells are cultured and differentiated on a tissue culture substrate coated with an extracellular matrix. The extracellular matrix may be a solubilized basement membrane preparation extracted from mouse sarcoma cells (which is sold by BD Biosciences under the trade name MATRIGEL). Alternatively, the extracellular matrix may be growth factor-reduced MATRIGEL. Alternatively, the extracellular matrix may fibronectin. In an alternate embodiment, the human embryonic stem cells are cultured and differentiated on tissue culture substrate coated with human serum.

The extracellular matrix may be diluted prior to coating the tissue culture substrate. Examples of suitable methods for diluting the extracellular matrix and for coating the tissue culture substrate may be found in Kleinman, H. K., et al., Biochemistry 25:312 (1986), and Hadley, M.A., et al., J. Cell. Biol. 101:1511 (1985).

In one embodiment, the extracellular matrix is MATRIGEL. In one embodiment, the tissue culture substrate is coated with MATRIGEL at a 1:10 dilution. In an alternate embodiment, the tissue culture substrate is coated with MATRIGEL at a 1:15 dilution. In an alternate embodiment, the tissue culture substrate is coated with MATRIGEL at a 1:30 dilution. In an alternate embodiment, the tissue culture substrate is coated with MATRIGEL at a 1:60 dilution.

In one embodiment, the extracellular matrix is growth factor-reduced MATRIGEL. In one embodiment, the tissue culture substrate is coated with growth factor-reduced MATRIGEL at a 1:10 dilution. In an alternate embodiment, the tissue culture substrate is coated with growth factor-reduced MATRIGEL at a 1:15 dilution. In an alternate embodiment, the tissue culture substrate is coated with growth factor-reduced MATRIGEL at a 1:30 dilution. In an alternate embodiment, the tissue culture substrate is coated with growth factor reduced MATRIGEL at a 1:60 dilution.

Differentiation of human embryonic stem cells into cells expressing markers characteristic of the definitive endoderm lineage on an extracellular matrix, using a single culture medium: In one embodiment, the present invention provides a method for differentiating human embryonic stem cells expressing markers characteristic of the definitive endoderm lineage, comprising the steps of:

a. Plating the human embryonic stem cells on a tissue culture substrate coated with an extracellular matrix, and
b. Culturing the human embryonic stem cells with activin-A and a Wnt ligand.

The culture medium should contain sufficiently low concentrations of certain factors to allow the differentiation of human embryonic stem cells to definitive endoderm, such as, for example insulin and IGF (as disclosed in WO2006020919). This may be achieved by lowing the serum concentration, or alternatively, by using chemically defined media that lacks insulin and IGF. Examples of chemically defined media are disclosed in Wiles et al (Exp Cell Res. 1999 Feb. 25; 247(1): 241-8.).

The culture medium may have a serum concentration in the range of about 0% to about 10%. In an alternate embodiment, the concentration may be in the range of about 0% to about 5%. In an alternate embodiment, the concentration may be in the range of about 0% to about 2%. In an alternate embodiment, the concentration may be about 2%.

The time of culturing with activin-A and a Wnt ligand may range from about 1 day to about 7 days. In an alternate embodiment, the time of culturing may range from about 1 day to about 3 days. In an alternate embodiment, the time of culturing may be about 3 days.

Activin-A may be used at any concentration suitable to cause differentiation of the human embryonic stem cells. The concentration maybe from about 1 pg/ml to about 100 μg/ml. In an alternate embodiment, the concentration may be about 1 pg/ml to about 1 μg/ml. In another alternate embodiment, the concentration may be about 1 pg/ml to about 100 ng/ml. In another alternate embodiment, the concentration may be about 50 ng/ml to about 100 ng/ml. In another alternate embodiment, the concentration may be about 100 ng/ml.

The choice of the Wnt ligand may be optimized to improve the efficiency of the differentiation process. The Wnt ligand may be selected from the group consisting of Wnt-1, Wnt-3a, Wnt-5a and Wnt-7a. In one embodiment, the Wnt ligand is Wnt-1. In an alternate embodiment, the Wnt ligand is Wnt-3a.

The Wnt ligand may be at a concentration of about 1 ng/ml to about 1000 ng/ml. In an alternate embodiment, the concentration may be about 10 ng/ml to about 100 ng/ml.

The single culture medium may also contain a GSK-3B inhibitor. The GSK-3B inhibitor may be selected from the group consisting of GSK-3B inhibitor 1× and GSK-3B inhibitor XI. In one embodiment, the GSK-3B inhibitor is GSK-3B inhibitor IX.

When culturing human embryonic stem cells with a GSK-3B inhibitor, the concentration of the GSK-3B inhibitor may be from about 1 nM to about 1000 nM. In an alternate embodiment, the human embryonic stem cells are cultured with the GSK-3B inhibitor at a concentration of about 10 nM to about 100 nM.

The single culture medium may also contain at least one other additional factor that may enhance the formation of cells expressing markers characteristic of the definitive endoderm lineage from human embryonic stem cells. Alternatively, the at least one other additional factor may enhance the proliferation of the ells expressing markers characteristic of the definitive endoderm lineage formed by the methods of the present invention. Further, the at least one other additional factor may enhance the ability of the cells expressing markers characteristic of the definitive endoderm lineage formed by the methods of the present invention to form other cell types, or improve the efficiency of any other additional differentiation steps.

The at least one additional factor may be, for example, nicotinamide, members of TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valproic acid, trichostatin A, sodium butyrate, hepatocyte growth factor (HGF), sphingosine 1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

Differentiation of human embryonic stem cells into cells expressing markers characteristic of the definitive endoderm lineage on an extracellular matrix, using two culture media: Differentiation of human embryonic stem cells into cells of a definitive endoderm lineage may be accomplished by culturing the human embryonic stem cells with activin-A and a Wnt ligand using two culture media. Thus, the differentiation of the human embryonic stem cells may be accomplished as follows:

a. Plating the human embryonic stem cells on a tissue culture substrate coated with an extracellular matrix,
b. Culturing the human embryonic stem cells with activin-A and a Wnt ligand in a first culture medium, and
c. Culturing the human embryonic stem cells with activin-A in a second culture medium.

The first culture medium may contain serum at a low concentration, and the second culture medium may contain serum at a higher concentration than the first culture medium.

The second culture medium may contain a Wnt ligand.

First Culture Medium: The first culture medium should contain sufficiently low concentrations of certain factors to allow the differentiation of human embryonic stem cells into cells expressing markers characteristic of the definitive endoderm lineage, such as, for example insulin and IGF (as disclosed in WO2006020919). This may be achieved by lowing the serum concentration, or alternatively, by using chemically defined media that lacks insulin and IGF. Examples of chemically defined media are disclosed in Wiles et al (Exp Cell Res. 1999 Feb. 25; 247(1):241-8.).

In the first culture medium there may be a lower concentration of serum, relative to the second culture medium. Increasing the serum concentration in the second culture medium increases the survival of the cells, or, alternatively, may enhance the proliferation of the cells. The serum concentration of the first medium may be in the range of about 0% to about 10%. Alternatively, the serum concentration of the first medium may be in the range of about 0% to about 2%. Alternatively, the serum concentration of the first medium may be in the range of about 0% to about 1%. Alternatively, the serum concentration of the first medium may be about 0.5%.

When culturing the human embryonic stem cells with activin-A and a Wnt ligand using at least two culture media, the time of culturing in the first culture medium may range from about 1 day to about 3 days.

Activin-A may be used at any concentration suitable to cause differentiation of the human embryonic stem cells. The concentration maybe from about 1 pg/ml to about 100 μg/ml. In an alternate embodiment, the concentration may be about 1 pg/ml to about 1 μg/ml. In another alternate embodiment, the concentration may be about 1 pg/ml to about 100 ng/ml. In another alternate embodiment, the concentration may be about 50 ng/ml to about 100 ng/ml. In another alternate embodiment, the concentration may be about 100 ng/ml.

The choice of the Wnt ligand may be optimized to improve the efficiency of the differentiation process. The Wnt ligand may be selected from the group consisting of Wnt-1, Wnt-3a, Wnt-5a and Wnt-7a. In one embodiment, the Wnt ligand is Wnt-1. In an alternate embodiment, the Wnt ligand is Wnt-3a.

The Wnt ligand may be at a concentration of about 1 ng/ml to about 1000 ng/ml. In an alternate embodiment, the concentration may be about 10 ng/ml to about 100 ng/ml.

The first culture medium may also contain a GSK-3B inhibitor. The GSK-3B inhibitor may be added to the first culture medium, to the second culture medium, or to both the first and second culture media.

The GSK-3B inhibitor may be selected from the group consisting of GSK-3B inhibitor IX and GSK-3B inhibitor XI. In one embodiment, the GSK-3B inhibitor is GSK-3B inhibitor IX.

When culturing human embryonic stem cells with a GSK-3B inhibitor, the concentration of the GSK-3B inhibitor may be from about 1 nM to about 1000 nM. In an alternate embodiment, the human embryonic stem cells are cultured with the GSK-3B inhibitor at a concentration of about 10 nM to about 100 nM.

The first culture medium may also contain at least one other additional factor that may enhance the formation of cells expressing markers characteristic of the definitive endoderm lineage from human embryonic stem cells. Alternatively, the at least one other additional factor may enhance the proliferation of the cells expressing markers characteristic of the definitive endoderm lineage formed by the methods of the present invention. Further, the at least one other additional factor may enhance the ability of the cells expressing markers characteristic of the definitive endoderm lineage formed by the methods of the present invention to form other cell types, or improve the efficiency of any other additional differentiation steps.

The at least one additional factor may be, for example, nicotinamide, members of the TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valproic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

Second Culture Medium: The second culture medium should contain certain factors, such as, for example, insulin and IGF (as disclosed in WO2006020919), at a sufficient concentration to promote the survival of the cultured cells. This may be achieved by increasing the serum concentration, or, alternatively, by using chemically defined media where the concentrations of insulin and IGF are increased relative to the first culture medium. Examples of chemically defined media are disclosed in Wiles et al (Exp Cell Res. 1999 Feb. 25; 247(1): 241-8.).

In a second culture medium having higher concentrations of serum, the serum concentration of the second culture medium may be in the range about 0.5% to about 10%. Alternatively, the serum concentration of the second culture medium may be in the range of about 0.5% to about 5%. Alternatively, the serum concentration of the second culture medium may be in the range of about 0.5% to about 2%. Alternatively, the serum concentration of the second culture medium may be about 2%. When culturing human embryonic stem cells with the second culture medium, the time of culturing may range from about 1 day to about 4 days.

Similar to the first culture medium, Activin-A may be used at any concentration suitable to cause differentiation of the human embryonic stem cells. The concentration maybe from about 1 pg/ml to about 100 μg/ml. In an alternate embodiment, the concentration may be about 1 pg/ml to about 1 μg/ml. In another alternate embodiment, the concentration may be about 1 pg/ml to about 100 ng/ml. In another alternate embodiment, the concentration may be about 50 ng/ml to about 100 ng/ml. In another alternate embodiment, the concentration may be about 100 ng/ml.

The Wnt ligand may be at a concentration of about 1 ng/ml to about 1000 ng/ml. In an alternate embodiment, the concentration may be about 10 ng/ml to about 100 ng/ml.

The Wnt ligand may be selected from the group consisting of Wnt-1, Wnt-3a, Wnt-5a and Wnt-7a. In one embodiment, the Wnt ligand is Wnt-1. In an alternate embodiment, the Wnt ligand is Wnt-3a.

The second culture medium may also contain a GSK-3B inhibitor. The GSK-3B inhibitor may be added to the first culture medium, to the second culture medium, or to both the first and second culture media.

The GSK-3B inhibitor may be selected from the group consisting of GSK-3B inhibitor IX and GSK-3B inhibitor XI. In one embodiment, the GSK-3B inhibitor is GSK-3B inhibitor IX.

When culturing human embryonic stem cells with a GSK-3B inhibitor, the concentration of the GSK-3B inhibitor may be from about 1 nM to about 1000 nM. In an alternate embodiment, the human embryonic stem cells are cultured with the GSK-3B inhibitor at a concentration of about 10 nM to about 100 nM.

Similar to the first culture medium, the second culture medium may also contain at least one other additional factor that may enhance the formation of cells expressing markers characteristic of the definitive endoderm lineage from human embryonic stem cells. Alternatively, the at least one other additional factor may enhance the proliferation of the cells expressing markers characteristic of the definitive endoderm lineage formed by the methods of the present invention. Further, the at least one other additional factor may enhance the ability of the cells expressing markers characteristic of the definitive endoderm lineage formed by the methods of the present invention to form other cell types, or improve the efficiency of any other additional differentiation steps.

The at least one additional factor may be, for example, nicotinamide, members of the TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valproic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

The present invention is further illustrated, but not limited by, the following examples.

Example 1

Human Embryonic Stem Cell Culture

Stem cells are undifferentiated cells defined by their ability at the single cell level to both self-renew and differentiate to produce progeny cells, including self renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

The human embryonic stem cell lines H1, H7 and H9 were obtained from WiCell Research Institute, Inc., (Madison, Wis.) and cultured according to instructions provided by the source institute. Briefly, cells were cultured on mouse embryonic fibroblast (MEF) feeder cells in ES cell medium consisting of DMEM/F12 (Invitrogen/GIBCO) supplemented with 20% knockout serum replacement, 100 nM MEM nonessential amino acids, 0.5 mM beta-mercaptoethanol, 2 mM L-glutamine with 4 ng/ml human basic fibroblast growth factor (bFGF) (all from Invitrogen/GIBCO). MEF cells, derived from E13 to 13.5 mouse embryos, were purchased from Charles River. MEF cells were expanded in DMEM medium supplemented with 10% FBS (Hyclone), 2 mM glutamine, and 100 mM MEM nonessential amino acids. Sub-confluent MEF cell cultures were treated with 10 μg/ml mitomycin C (Sigma, St. Louis, Mo.) for 3 h to arrest cell division, then trypsinized and plated at 2×104/cm2 on 0.1% bovine gelatin-coated dishes. MEF cells from passage two through four were used as feeder layers. Human embryonic stem cells plated on MEF cell feeder layers were cultured at 37° C. in an atmosphere of 5% $CO_2$ within a humidified tissue culture incubator. When confluent (approximately 5-7 days after plating), human embryonic stem cells were treated with 1 mg/ml collagenase type IV (Invitrogen/GIBCO) for 5-10 min and then gently scraped off the surface using a 5-ml pipette. Cells were centrifuged at 900 rpm for 5 min, and the pellet was resuspended and re-plated at a 1:3 to 1:4 ratio of cells in fresh culture medium.

In parallel, H1, H7, and H9 human embryonic stem cells were also seeded on plates coated with a 1:30 dilution of growth factor reduced MATRIGEL (BD Biosciences) and cultured in MEF-conditioned media supplemented with 8 ng/ml bFGF. The cells cultured on MATRIGEL were routinely passaged with collagenase IV (Invitrogen/GIBCO), Dispase (BD Biosciences) or LIBERASE enzyme. Some of the human embryonic stem cell cultures were incubated under hypoxic conditions (approximately 3% $O_2$).

Example 2

Fluorescence-Activated Cell Sorting (FACS) Analysis

Adhered human embryonic stem cells were removed from culture plates by a five-minute incubation with TrypLE™ Express solution (Invitrogen, CA). Released cells were resuspended in human embryonic stem cell culture medium and recovered by centrifugation, followed by washing and resuspending the cells in a staining buffer consisting of 2% BSA, 0.05% sodium azide in PBS (Sigma, Mo.). As appropriate, the cells were Fc-receptor blocked for 15 minutes using a 0.1% γ-globulin (Sigma) solution. Aliquots (approximately $1\times10^5$ cells) were incubated with either phycoerythrin (PE) or allophycocyanin (APC) conjugated monoclonal antibodies (5 μl antibody per $1\times10^6$ cells), as indicated in Table IA, or with an unconjugated primary antibody. Controls included appropriate isotype matched antibodies, unstained cells, and cells stained only with secondary conjugated antibody. All incubations with antibodies were performed for 30 mins at 4° C., after which the cells were washed with the staining buffer. Samples that were stained with unconjugated primary antibodies were incubated for an additional 30 mins at 4° C. with secondary conjugated PE or -APC labeled antibodies. See Table IB for a list of secondary antibodies used. Washed cells were pelleted and resuspended in the staining buffer, and the cell surface molecules were identified using a FACS Array (BD Biosciences) instrument, collecting at least 10,000 events.

Example 3

Immunocytochemistry

Adhered cells were fixed with 4% paraformaldehyde for 20 min at room temperature. Fixed cells were blocked for 1 h at room temperature with PBS/0.1% BSA/10% normal chick serum/0.5% Triton X-100 and then incubated overnight with primary antibodies in PBS/0.1% BSA/10% normal chick serum at 4° C. The list of primary antibodies and their working dilutions are shown in Table IA. After three washes in PBS/0.1% BSA, fluorescent secondary antibodies (Table IB) at a 1:100 dilution in PBS were incubated with cells for 1 h at room temperature to allow binding. Control samples included reactions where the primary antibody was omitted or where the primary antibody was replaced with corresponding matched negative control immunoglobulins at the same concentration as the primary antibodies. Stained samples were rinsed; a drop of PROLONG® (Invitrogen, CA) containing diamidino-2-phenylindole, dihydrochloride (DAPI) was added to each sample to counter-stain the nucleus and to function as an anti-fade reagent. Images were acquired using a Nikon Confocal Eclipse C-1 inverted microscope (Nikon, Japan) and a 10-60× objective.

Example 4

PCR Analysis of ES Derived-Cells

RNA extraction, purification, and cDNA synthesis: RNA samples were purified by binding to a silica-gel membrane (Rneasy Mini Kit, Qiagen, CA) in the presence of an ethanol-containing, high-salt buffer followed by washing to remove contaminants. The RNA was further purified using a TURBO DNA-free kit (Ambion, INC), and high-quality RNA was then eluted in water. Yield and purity were assessed by A260 and A280 readings on a spectrophotometer. cDNA copies were made from purified RNA using an ABI (ABI, CA) high capacity cDNA archive kit.

Real-time PCR amplification and quantitative analysis: Unless otherwise stated, all reagents were purchased from Applied Biosystems. Real-time PCR reactions were performed using the ABI PRISM® 7900 Sequence Detection System. TAQMAN® UNIVERSAL PCR MASTER MIX® (ABI, CA) was used with 20 ng of reverse transcribed RNA in a total reaction volume of 20 μl. Each cDNA sample was run in duplicate to correct for pipetting errors. Primers and FAM-labeled TAQMAN® probes were used at concentrations of 200 nM. The level of expression for each target gene was normalized using a human glyceraldehyde-3-phosphate dehydrogenase (GAPDH) endogenous control previously developed by Applied Bio systems. Primer and probe sets are listed in Table II. SOX-17 primers were designed using the PRIMERS program (ABI, CA) and were the following sequences: SOX-17: TGGCGCAGCAGATACCA, AGCGCCTTCCACGACTTG, and CCAGCATCTTGCTCAACTCGGCG. After an initial incubation at 50° C. for 2 min followed by 95° C. for 10 min, samples were cycled 40 times in two stages—a denaturation step at 95° C. for 15 sec followed by an annealing/extension step at 60° C. for 1 min Data analysis was carried out using GENEAMP®7000 Sequence Detection System software. For each primer/probe set, a Ct value was determined as the cycle number at which the fluorescence intensity reached a specific value in the middle of the exponential region of amplification. Relative gene expression levels were calculated using the comparative Ct method. Briefly, for each cDNA sample, the endogenous control Ct value was subtracted from the gene of interest Ct to give the delta Ct value (ΔCt). The normalized amount of target was calculated as 2-ΔCt, assuming amplification to be 100% efficiency. Final data were expressed relative to a calibrator sample.

Example 5

Differentiation of Human Embryonic Stem Cells Cultured on Tissue Culture Substrate Coated with MATRIGEL to Definitive Endoderm (DE)

Figure 1:
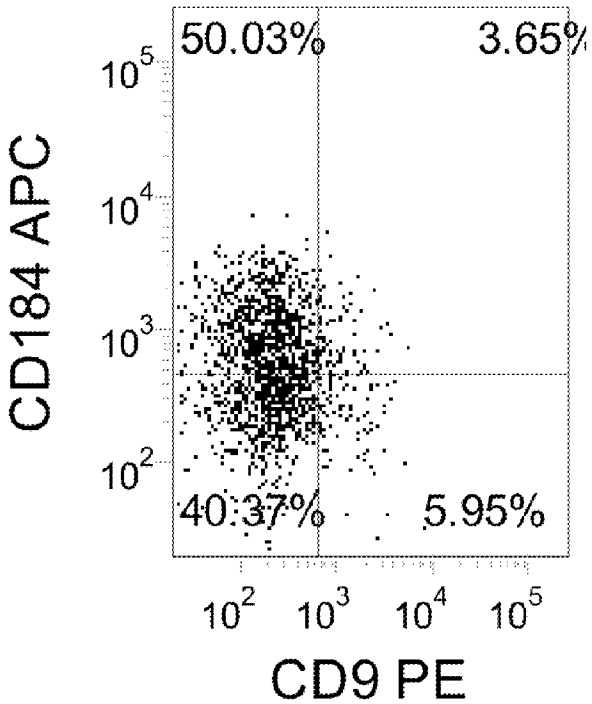
FIG. 1 shows the expression of CXCR4 (CD 184, Y-axis) and CD9 (X-axis) in cells from the human embryonic stem cell line H9 at passage 54 that have been differentiated into definitive endoderm following treatment with low serum+Activin-A+WNT-3A for 4 days.
Figure 2:
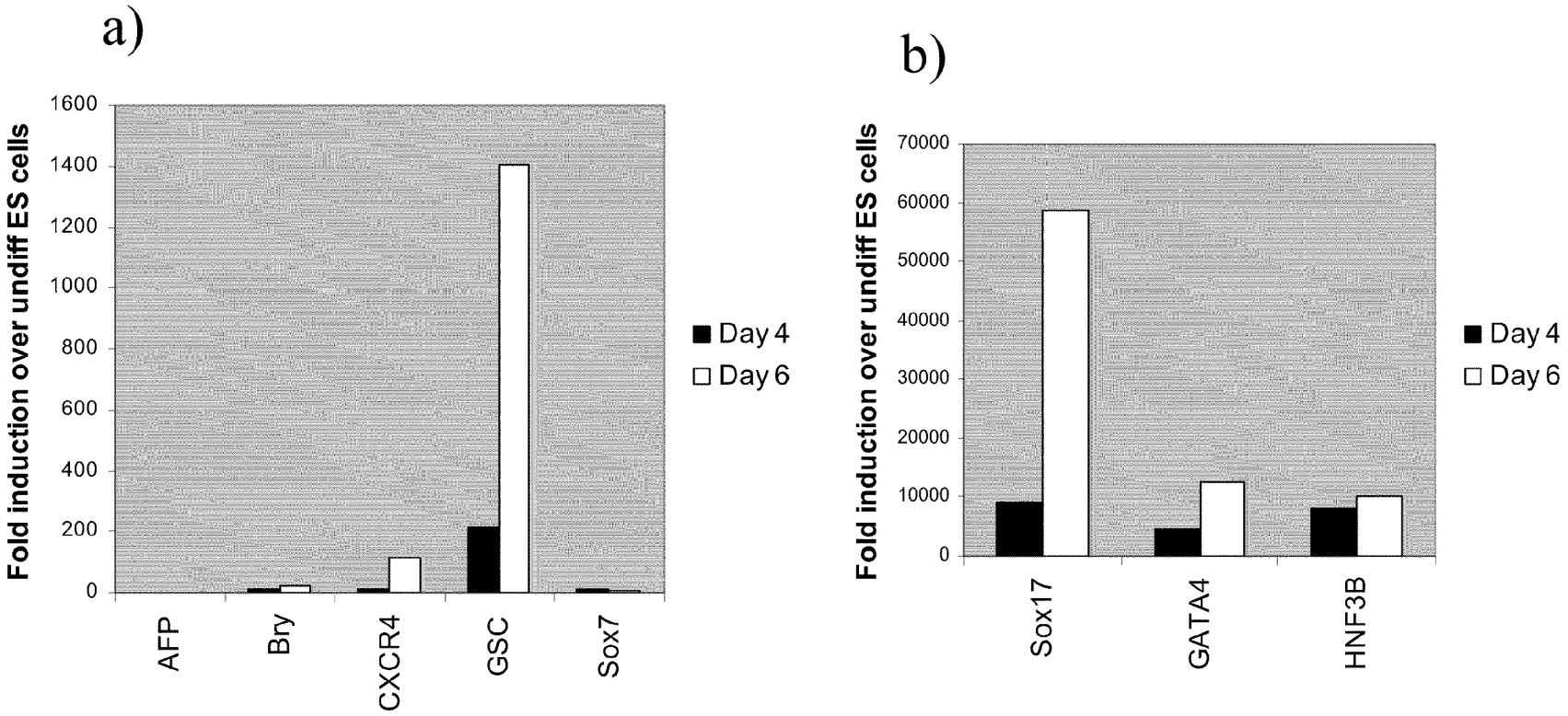
FIG. 2 shows the real-time PCR analysis of cells from the human embryonic stem cell line H9 at passage 54 at day 4 and 6 of the definitive endoderm differentiation protocol outlined in Example 5. Panel a) depicts expression of AFP, Bry, CXCR4, GSC, and SOX-7. Panel b) depicts the expression of SOX-17, GATA-4, and HNF-3 beta.

Cells from the human embryonic stem cell line H9 at passage 54 were cultured under hypoxic conditions (approximately 3% $O_2$) and plated on MATRIGEL (1:30 dilution) coated dishes were exposed to DMEM/F12 medium supplemented with 0.5% FBS, 20 ng/ml WNT-3a (Catalog# 1324-WN-002, R&D Systems, MN), and 100 ng/ml Activin-A (R&D Systems, MN) for two days followed by treatment with DMEM/F12 media supplemented with 2% FBS and 100 ng/ml Activin-A (AA) for an additional 3-4 days. FIG. 1 depicts the expression of CXCR4 by FACS at day 4. FIG. 2 displays the real-time PCR data for cultures of cells from the human embryonic stem cell line H9 treated with low serum+AA+WNT3A at days 4 and 6. This protocol resulted in significant upregulation of definitive endoderm markers. This procedure will be further referred to as the DE (Definite Endoderm) protocol.

Example 6

Figure 3:
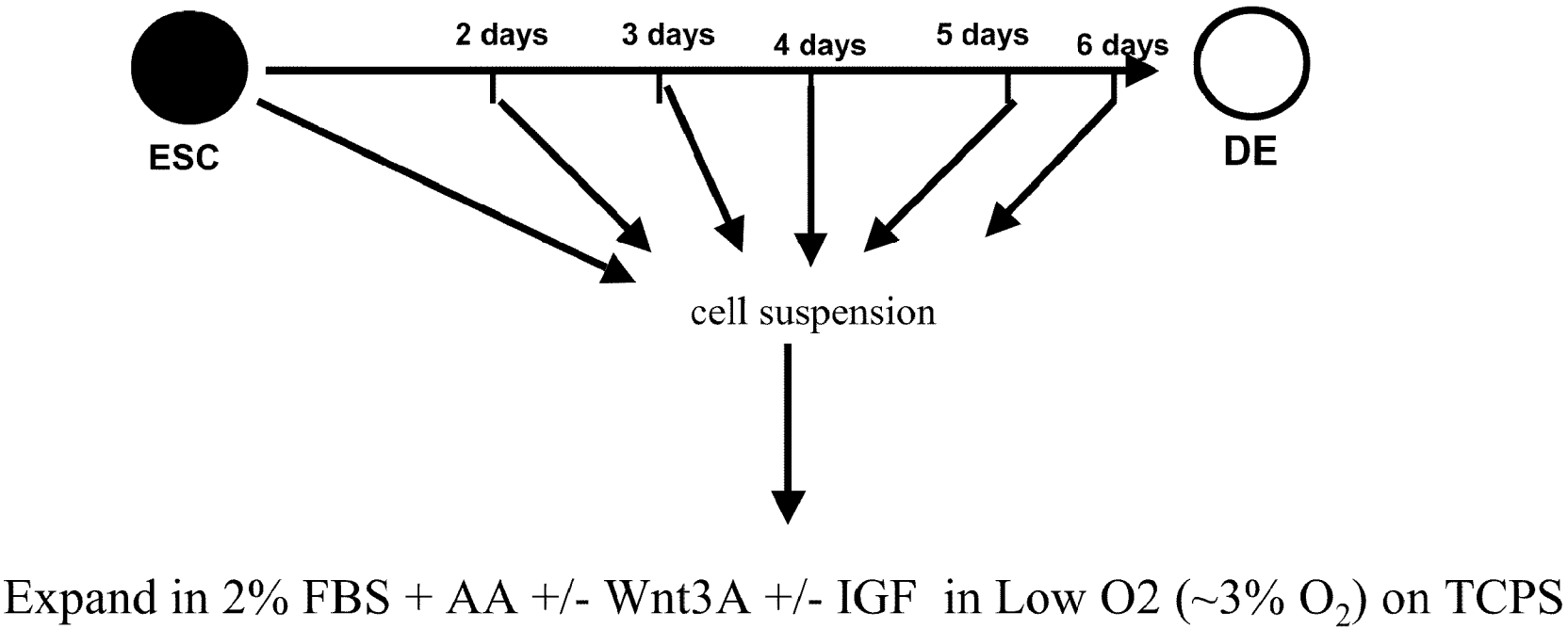
FIG. 3 shows the isolation protocol used to derive EXPRES cells from embryonic stem cells according to the methods of the present invention.

Isolation and Expansion of Human Embryonic Stem Cell Derived Cells Differentiated to the Definitive Endoderm Stage Cells from the human embryonic stem cell lines H1 and H9 various passages (Passage 30-54) were cultured under hypoxic conditions (approximately 3% 02) for at least three passages. The cells were cultured in MEF-CM supplemented with 8 ng/ml of bFGF and plated on MATRIGEL coated plates according to Example 1. The cells were exposed to the DE protocol outlined in Example 5. At days 3-6, the cultures were exposed to TrypLE™ Express solution (Invitrogen, CA) for 5 mins Released cells were resuspended in DMEM-F12+2% FBS medium, recovered by centrifugation, and counted using a hemocytometer. The released cells were seeded at 1000-10,000 cells/$cm^2$ on tissue culture polystyrene (TCPS) treated flasks and cultured in DMEM-F12+2% FBS+100 ng/ml activin-A+20 ng/ml WNT-3A under hypoxic conditions (approximately 3% $O_2$) at 37° C. in standard tissue culture incubator. The TCPS flaks were not coated with MATRIGEL or other extracellular matrix proteins. The media was changed daily. In some cultures, the media was further supplemented with 10-50 ng/ml of IGF-I (insulin growth factor-I from R&D Systems, MN) or 1×ITS (Insulin, transferrin, and selenium from Invitrogen, Ca). In some of the culture conditions the basal media (DM-F12+2% FBS) was further supplemented with 0.1 mM mercaptoethanol (Invitrogen, CA) and non-essential amino acids (1×, NEAA from Invitrogen, CA). The first passage cells are referred to as P1. In parallel, similar cultures were established under normoxic conditions (approximately 21% $O_2$). The outline of this isolation procedure is depicted in FIG. 3.

Figure 4:
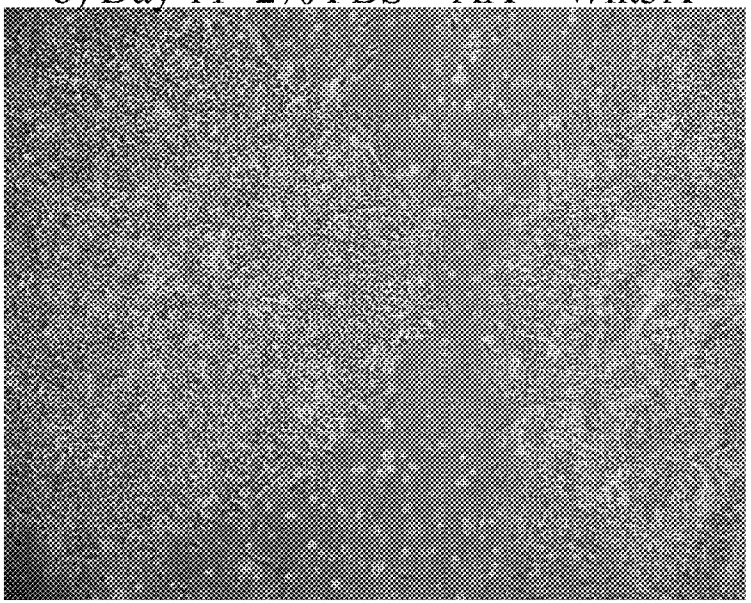
FIG. 4 shows the morphology of expanded EXPRES cells at P0, at day 11, that were cultured in 2% FBS+DMEM-F12+100 ng/ml of Activin-A (Panel a) or 2% FBS+DMEM-F12+100 ng/ml of Activin-A+20 ng/ml of WNT-3A (Panel b). Panel c shows the morphology of the EXPRES cells at passage 3.
Figure 4:
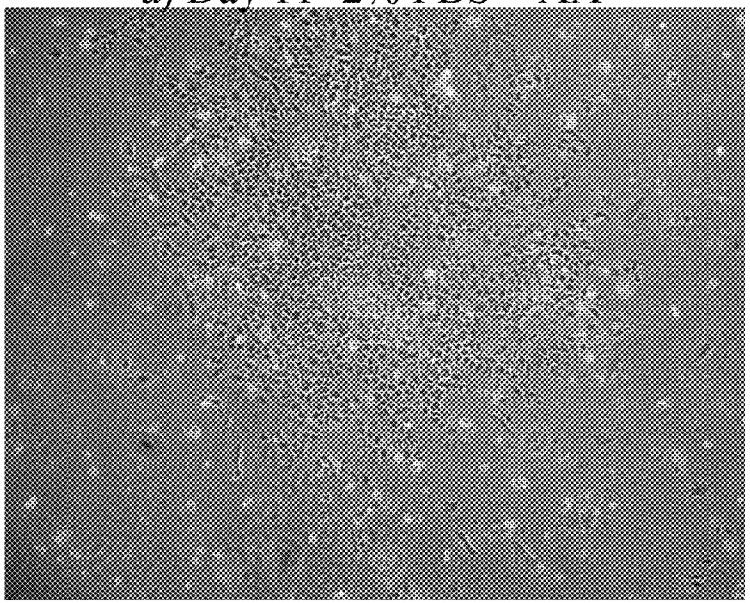
Figure 4:
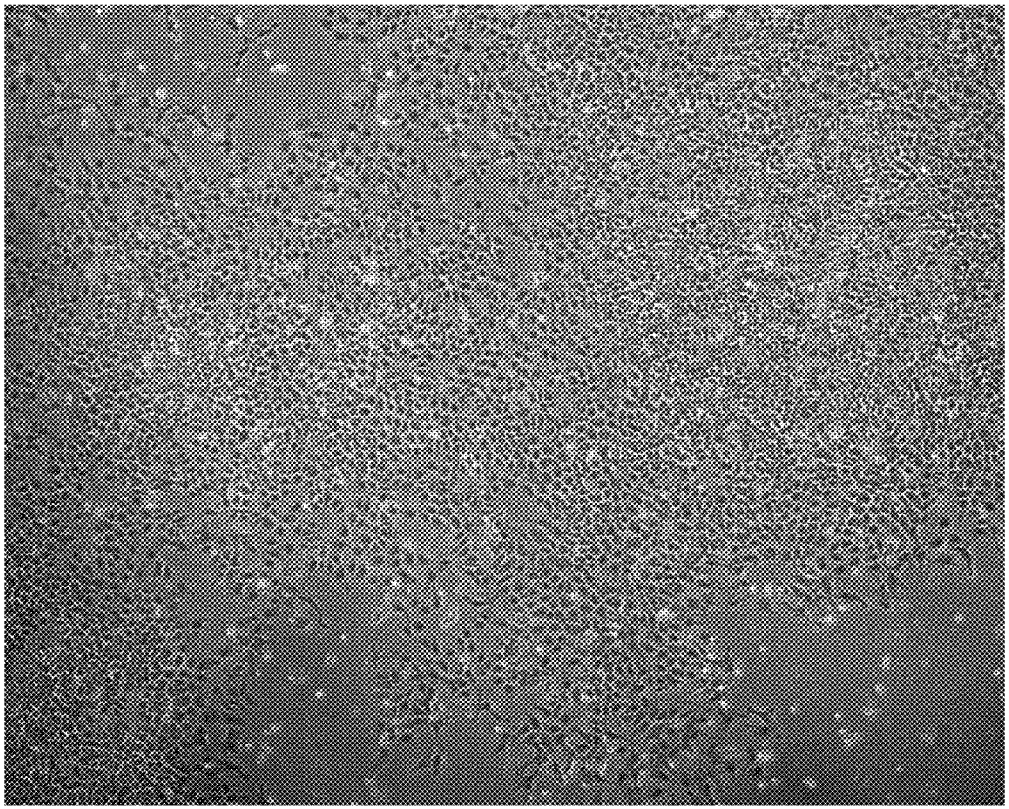

Following 5-15 days of culturing, distinct cell colonies appeared surrounded by a large number of enlarged cells that appear to be in senescence (FIG. 4a-b). At approximately 50-60% confluency, the cultures were passaged by exposure to TrypLE™ Express solution for 5 mins at room temperature. The released cells were resuspended in DMEM-F12+2% FBS medium, recovered by centrifugation, and seeded at 10,000 cells/$cm^2$ on tissue culture polystyrene (TCPS) treated flasks in DMEM-F12+2% FBS+100 ng/ml activin-A+20 ng/ml WNT-3A+/−50 ng/ml of IGF-I. This media will be further referred to as the "growth media". FIG. 4 c depicts the morphology of cells at passage 3 seeded at 10,000 cells/$cm^2$. At passage 3 (panel c) following the initial isolation, the cells appeared to have a uniform epithelial-like morphology with a large nucleus to cytoplasm ratio.

In some cultures the growth media was further supplemented with 1×NEAA plus 0.1 mM mercaptoethanol. Following three to four passages, the attached cells appeared to have a uniform morphology with a large nucleus to cytoplasm ratio. Parallel cultures established under normoxic conditions failed to show robust colony formation by attached cells. Following 2-3 passages, the cultures established under normoxic conditions were abandoned due to poor growth rate.

Example 7

Figure 5:
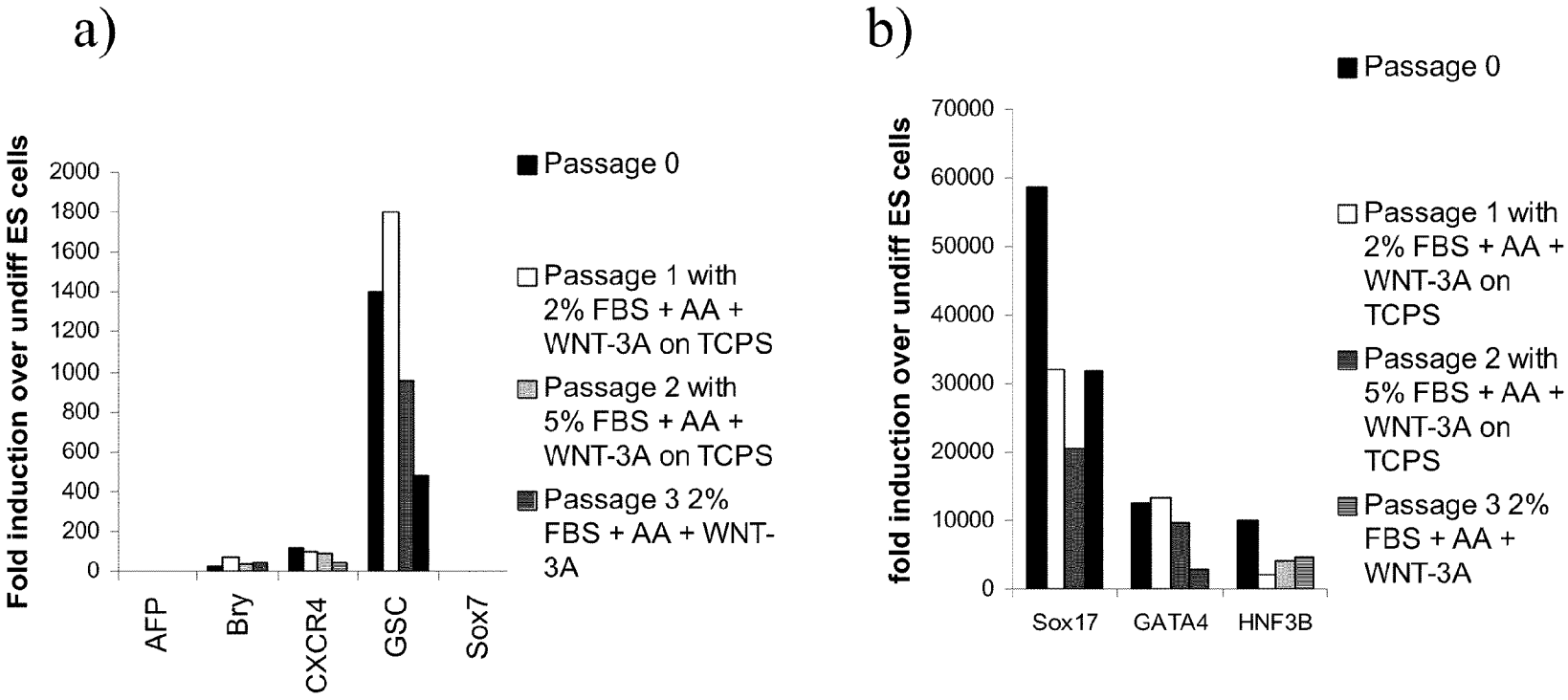
FIG. 5 shows the real-time PCR analysis of expanded EXPRES cells cultured in 2-5% FBS+DMEM-F12+100 ng/ml of Activin-A+20 ng/ml of WNT-3A for three passages. Panel a) depicts expression of AFP, Bry, CXCR4, GSC, and SOX-7. Panel b) depicts the expression of SOX-17, GATA-4, and HNF-3 beta.
Figure 6:
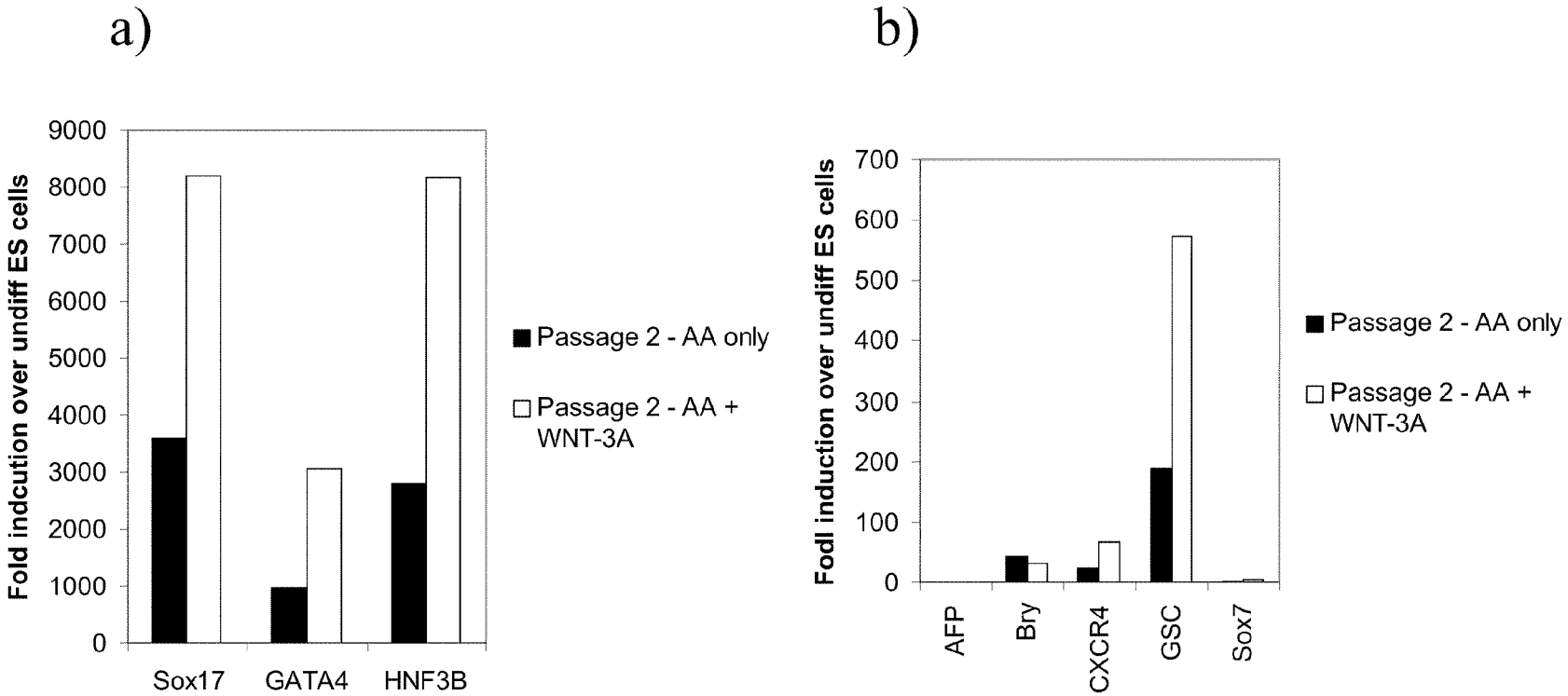
FIG. 6 shows the effect of the addition of Wnt-3A on gene expression in EXPRES cells. Panel a) depicts real-time PCR expression of SOX-17, GATA-4, and HNF-3 beta. Panel b) depicts real-time PCR expression of AFP, Bry, CXCR4, GSC, and SOX-7.
Figure 7:
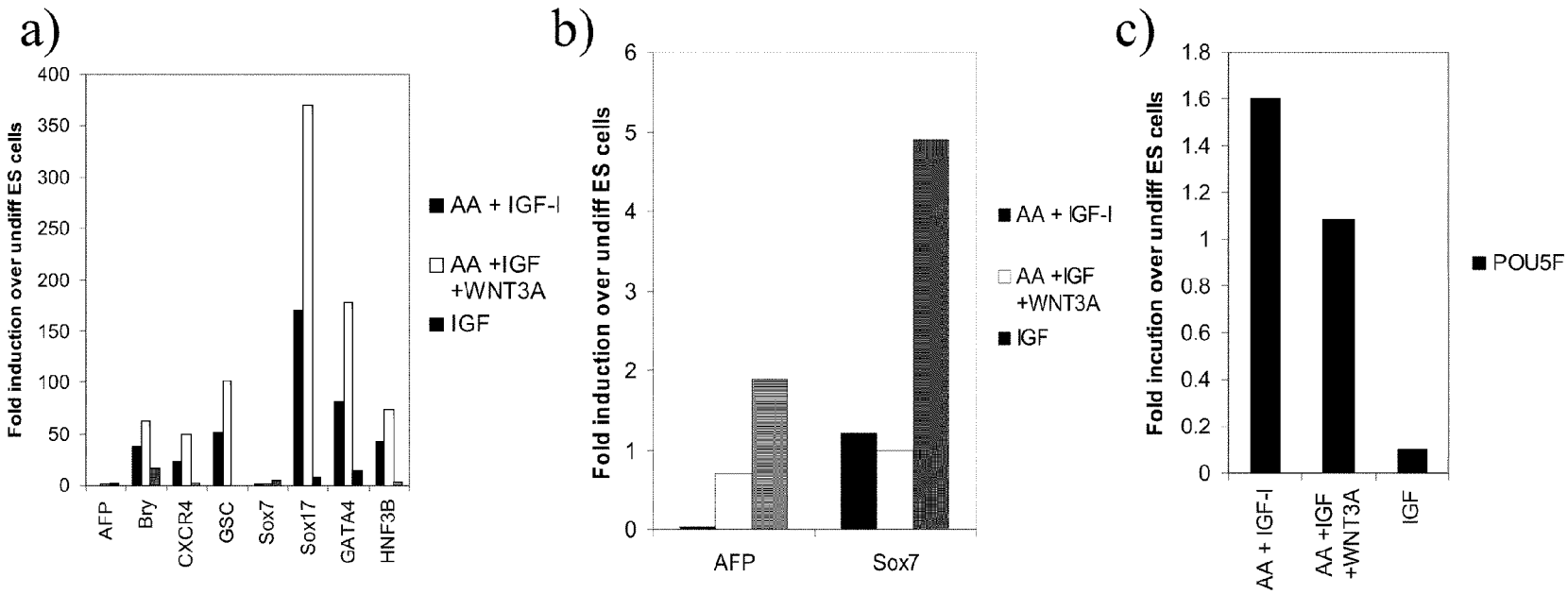
FIG. 7 shows the effect of IGF-1, Wnt-3A and activin-A on gene expression in EXPRES cells. Panel a) depicts real-time PCR expression of SOX-17, GATA-4, HNF-3 beta, Bry, CXCR4, and GSC. Panel b) depicts real-time PCR expression of and SOX-7 and AFP. Panel c) depicts real-time PCR expression of OCT-4.
Figure 8:
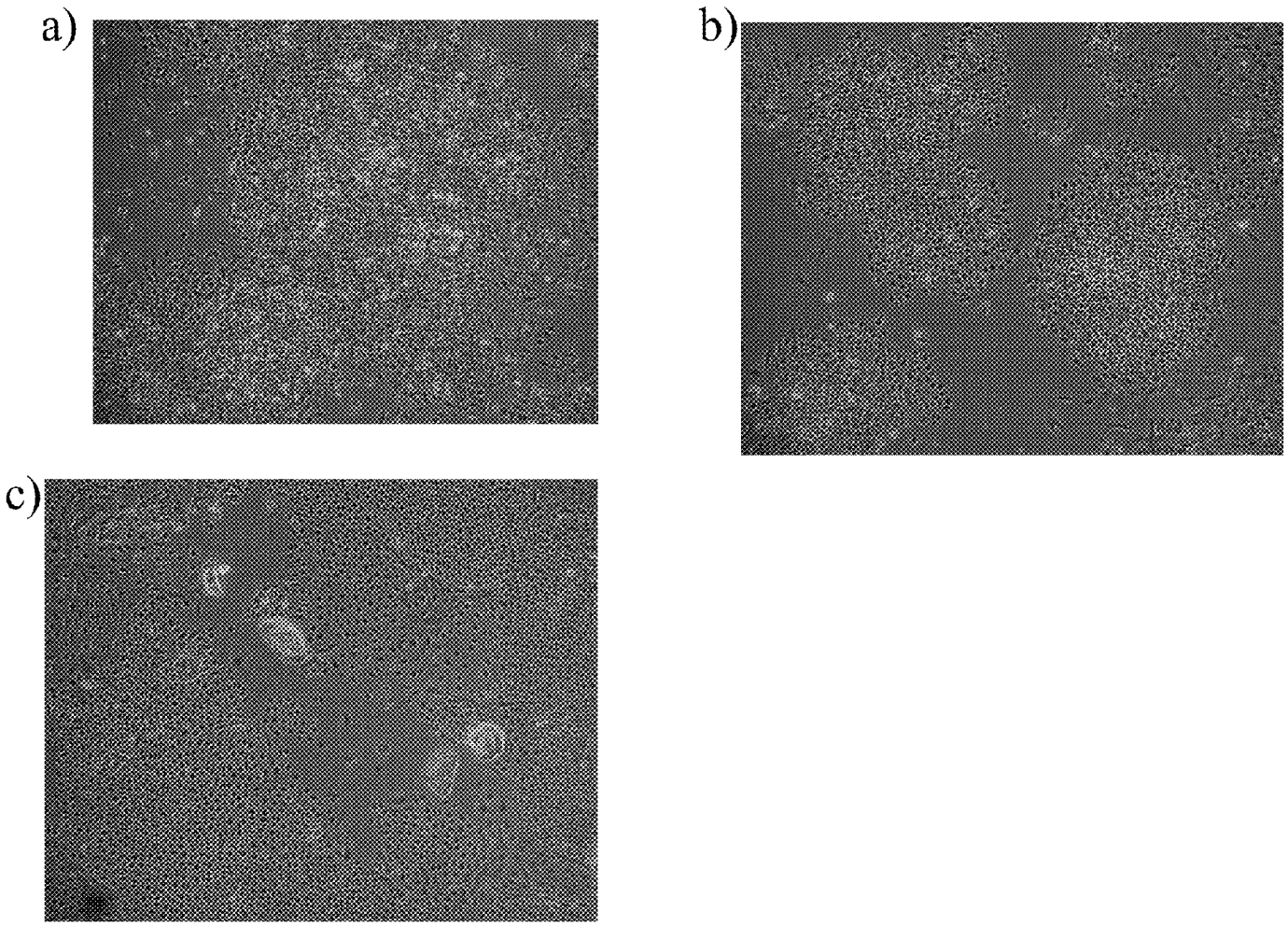
FIG. 8 shows the morphology of expanded EXPRES cells derived from the human embryonic stem cell line H9 at passage 54, cultured in a) 2% FBS+DMEM-F12+100 ng/ml of AA+20 ng/ml of WNT-3A, b) 2% FBS+DMEMF12+100 ng/ml of AA, c) 2% FBS+DMEM-F12+50 ng/ml of IGF-I.

Role of Activin-A, WNT3A, and IGF-I in Expansion and Maintenance of DE Markers Following Multiple Passages Cultures derived from the parental human embryonic stem cell line H9 according to the methods described in Example 6 were passaged every 4-7 days. FIG. 5 depicts real-time PCR results for the expanded cells cultured in 2% FBS+DMEM-F12+100 ng/ml of activin-A+20 of WNT3A for three passages. This data is for a line isolated at day 6 of the DE protocol outlined in Example 5. There is a clear decrease in DE markers, such as SOX-17 and HNF-3 beta following each passage. As shown in FIG. 6, addition of WNT3A to the growth media containing activin-A led to a significant boost in the expression of DE markers. However, addition of 50 ng/ml of IGF-I and withdrawal of Activin-A and WNT-3A (FIG. 7 a-c) led to a precipitous drop in the expression of DE markers along with OCT-4 and an increase in expression of visceral endoderm markers, such as SOX-7 and AFP. FIG. 8 a-c depicts the morphology of expanded cells derived from H9p54 at passage 5 cultured in a) 2% FBS+DMF12+100 ng/ml of activin-A+20 ng/ml of WNT-3A, b) 2% FBS+DM-F12+100 ng/ml of activin-A, c) 2% FBS+DM-F12+50 ng/ml of IGF-I. Morphology of cells cultured in the presence of activin-A or activin-A+WNT3A were very similar and distinct from morphology of cells cultured in 2% FBS+IGF-I.

Example 8

Figure 9:
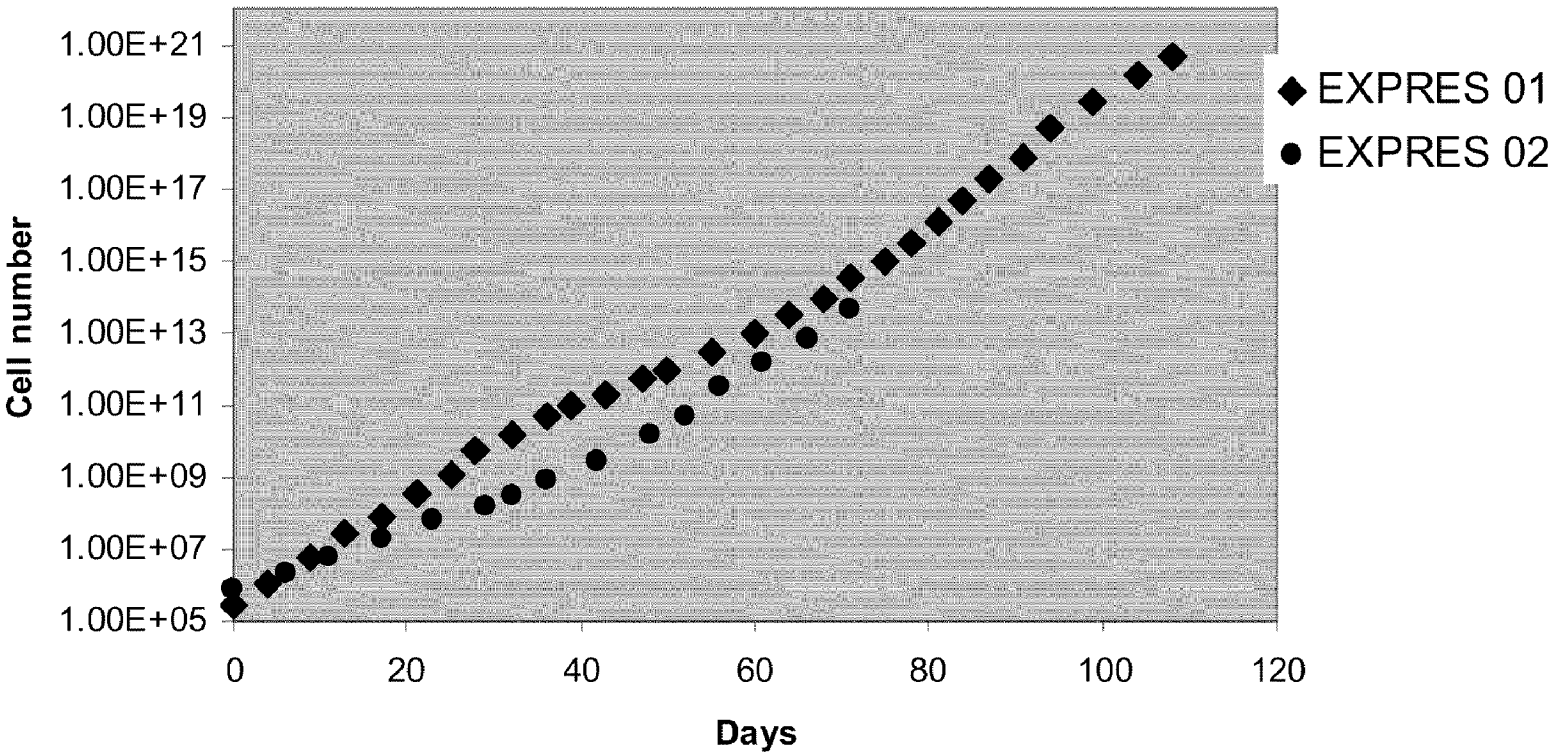
FIG. 9 shows the expansion potential of EXPRES 01 and 02 cells cultured on tissue culture polystyrene under hypoxic conditions. EXPRES 01 was cultured in 2% FBS+DM-F12+

Expansion Potential of Human Embryonic Stem Cell Derived Cells Differentiated to the Definitive Endoderm Stage Cultures established from the parental human embryonic stem cell line H9 according to the methods described in Example 6 were passaged every 4-5 days when the growth media contained 50 ng/ml of IGF-I or ITS. However, cultures fed with growth media lacking the IGF or ITS supplements showed slower growth rate and were passaged every 5-7 days. The population doubling time of cells fed with growth media+50 ng/ml of IGF-I was approximately 55 hrs where as the population doubling time of cultures fed only with the growth media was approximately 75 hrs. The cell population expanded according to Example 6 will be referred to as EXPRES cells (EXpandable PRE-primitive Streak cells). Table III lists various EXPRES cells established according to methods outlined in Example 6. The expansion potential of two cell lines (EXPRES 01 and 02) is depicted in FIG. 9.

Example 9

Derivation of EXPRES Cells from Suspensions of Single Human Embryonic Stem Cells Cells from the human embryonic stem cell lines H1 P33 and H9 P45 were cultured under hypoxic conditions (approximately 3% $O_2$) for at least three passages. The cells were cultured in MEF-CM supplemented with 8 ng/ml of bFGF and plated on MATRIGEL coated plates according to Example 1. At approximately 60% confluency, the cultures were exposed to TrypLE™ Express solution (Invitrogen, CA) for 5 mins Released cells were resuspended in DMEM-F12+2% FBS medium, recovered by centrifugation, and counted using a hemocytometer. The released cells were seeded at 1000 to 10,000 cells/$cm^2$ on tissue culture polystyrene (TCPS) treated flasks and cultured in DM-F12+2% FBS+100 ng/ml activin-A+20 ng/ml WNT-3A+50 ng/ml of IGF-I+0.1 mM mercaptoethanol (Invitrogen, CA) and non-essential amino acids (1×, NEAA from Invitrogen, CA) under hypoxic conditions (approximately 3% $O_2$) at 37° C. in a standard tissue culture incubator. The TCPS flasks were not coated with MATRIGEL or other extracellular matrix proteins. The media was changed daily. The first passage cells are referred to as P1. In parallel, similar cultures were established under normoxic conditions (approximately 21% $O_2$). Cultures established under atmospheric conditions did not result in colony formation and there was poor cell proliferation. However, cultures established under hypoxic conditions resulted in formation of many colonies (FIG. 10) resembling embryonic stem cell colonies cultured on MATRIGEL or on MEF feeders. These cultures closely resemble the properties of EXPRES cells isolated during ES to DE differentiation.

Example 10

Expression of Cell Surface Proteins by EXPRES Cells

The cell lines EXPRES 01 and EXPRES 02 were evaluated for expression of various cell-surface markers including markers associated with pluripotency. Cells from EXPRES 01 were evaluated at passages 9 to 24. Cells from EXPRES 02 were evaluated at passages 7 to 20. Both lines exhibited strong expression of pluripotency markers typically assigned to undifferentiated human embryonic stem cells. However, the EXPRES 02 line showed a higher percentage of expression of differentiation markers, such as CXCR4, LIF receptor, and NCAM as compared to the EXPRES 01 line. Representative FACS plots are depicted in FIG. 11 for EXPRES 01 P24 and in FIG. 12 for EXPRES 02 P21 line. Table IV lists the mean expression levels along with the ranges (in brackets) of the evaluated cell surface markers from three different experiments.

Example 11

Expression of Pluripotency Associated Markers by EXPRES Cells-Immuno Fluorescent (IF) Staining EXPRES 01 and 02 cells maintained in their respective growth media were stained for pluripotency-associated markers using methods outlined in Example 3. FIG. 13 depicts IF images for OCT-4, Nanog, SOX-2, and HNF-3 beta for EXPRES 01 P10 cells cultured in 2% FBS+DM-F12+100 ng/ml activin-A+20 ng/ml WNT3A+50 ng/ml IGF-I. FIG. 14 depicts IF images for OCT-4, Nanog, SOX-2, and HNF-3 beta for EXPRES 02 passage 9 cells cultured in 2% FBS+DM-F12+100 ng/ml activin-A+20 ng/ml WNT3A. EXPRES 01 cells strongly stain positive for OCT-4, Nanog, and SOX-2 and weakly for HNF-3 beta. However, EXPRES 02 cells show stronger expression for HNF-3 beta and weaker expression of OCT-4, NANOG, and SOX-2.

Example 12

Expression of Definitive Endoderm and Undifferentiated Embryonic Stem Cell Markers by Real Time PCR Real-time PCR analysis of embryonic markers (POU5F1, SOX-2, UTF1, ZFP42, Connexin43, Connexin45, FOXD3), extraembryonic markers (AFP, KRT15), ectoderm markers (SOX-1, TUBB3, NESTIN), endoderm markers (FOXA2, IPF1, KRT15, GATA-4), and mesoderm markers (GATA-4, GATA-2, MYOD, MSX1, CFC1, ABCG2) expressed by EXPRES 01 passage 11 and EXPRES 02 passage 7 lines cultured in their respective growth media is depicted in FIG. 15 a-h. All of the data is normalized to fold change with respect to undifferentiated cells from the human embryonic stem cell line H9, cultured in MEF-CM on MATRIGEL coated plates. As a control, EB bodies were formed from H9 cells using standard methods of collagenase digestion and seeding on non-treated surfaces in DMEM-F12+20% FBS for approximately 10 days. Gene expression of various germ layers was upregulated by EB bodies as compared to undifferentiated ES cells. Another reference RNA was collected from undifferentiated SA002 line (Cellartis, Sweden) cultured on MATRIGEL in MEF-CM. As expected gene expression of various germ layers was strongly upregulated by EB bodies as compared to EXPRES 01, EXPRES 02, SA002, and H9 lines. Both EXPRES 01 and 02 lines showed expression of FOXA2 as compared to undifferentiated SA002 and H9 lines. Neither of the EXPRES lines exhibited strong expression of extra embryonic, mesoderm or ectoderm markers. Furthermore, expression of embryonic markers by EXPRES cells was similar to the SA002 and H9 reference cell lines.

Example 13

Various Growth Media Useful for Expansion of EXPRES Cells

EXPRES cells have been successfully cultured in the following media compositions for at least 2-30 passages:

1. DM-F12+2% FBS+100 ng/ml AA+20 ng/ml WNT-3A
2. DM-F12+2% FBS+100 ng/ml AA+20 ng/ml WNT-3A+ 50 ng/ml IGF-I
3. DM-F12+2% FBS+100 ng/ml AA+20 ng/ml WNT-3A+ 10 ng/ml IGF-I
4. DM-F12+2% FBS+50 ng/ml AA+20 ng/ml WNT-3A+ 50 ng/ml IGF-I
5. DM-F12+2% FBS+50 ng/ml AA+10 ng/ml WNT-3A+ 50 ng/ml IGF-I
6. DM-F12+2% FBS+50 ng/ml AA+20 ng/ml WNT-3A+ 10 ng/ml IGF-I
7. DM-F12+2% FBS+100 ng/ml AA+10 ng/ml WNT-3A+ 10 ng/ml IGF-I
8. HEScGRO defined media (Chemicon, CA)

The basal component of the above listed media may be replaced with similar media such as, RPMI, DMEM, CRML, Knockout™DMEM, and F12.

Example 14

Differentiation of EXPRES Cells Cultured on Tissue Culture Substrate to Definitive Endoderm (DE) Cells EXPRES 01 cells at passage 5 and EXPRES 02 cells at passage 4, cultured on TCPS in their respective media were exposed to DMEM/F12 medium supplemented with 0.5% FBS, 20 ng/ml WNT-3a, and 100 ng/ml activin-A (R&D Systems, MN) for two days followed by treatment with DMEM/F12 media supplemented with 2% FBS and 100 ng/ml activin-A (AA) for an additional 3-5 days. FIG. 16 depicts the expression of CXCR4 by FACS at days 4 for EXPRES 01 cells (FIG. 16 a, approximately 17% CXCR4 positive) and EXPRES 02 cells (FIG. 16b, approximately 40% CXCR4 positive). FIG. 17 displays the real-time PCR data for EXPRES 01 cell (FIG. 17a) and EXPRES 02 cell (FIG. 17b) cultures treated with low serum+AA+WNT3A at days 2-5. FIGS. 18 and 19 depict immunofluorescence images of EXPRES 01 and 02 cells, respectively, treated with the same treatment mentioned above for 4 days. Overall EXPRES 02 cells appear to show a stronger expression of DE markers as compared to EXPRES 01 cells. As evident by FACS, immuno staining, and PCR data, lowering of serum concentration and removal of IGF did enhance the expression of DE markers. However, the overall expression level of DE markers such as CXCR4 and HNF-3 beta was lower than what we have routinely observed in undifferentiated human ES cultures differentiated to the DE stage.

In order to enhance expression of DE markers, the DE differentiation protocol was changed to the following: EXPRES 01 cells at passage 19 and EXPRES 02 cells at passage 14 cultured on TCPS in their respective media were exposed to DMEM/F12 medium supplemented with 0.5% FBS, 20 ng/ml WNT-3a, 100 ng/ml activin-A, and 100 nM GSK-3B inhibitor IX (Catalog# 361550, Calbiochem, CA) for 4 to 5 days. FIG. 20 depicts the expression of CXCR4 by FACS at days 4 for EXPRES 01 (FIG. 20 a, approximately 57% CXCR4 positive) and EXPRES 02 (FIG. 20b, approximately 86% CXCR4 positive). FIG. 21 depicts the corresponding immuno fluorescent images at day 5 for EXPRES 01 cells (panels a-f) and EXPRES 02 cells (panels g-l) cells differentiated to the DE stage. FIG. 22 displays the real-time PCR data for EXPRES 01 (FIG. 22a) and EXPRES 02 (FIG. 22b).

Example 15

Effect of Seeding Density on the Differentiation of EXPRES 01 Cells to DE

EXPRES 01 P31 cells were seeded at 5000, 10000, 20000, or 40000 cells/cm$^2$ on TCPS plates in DM-F12+2% FBS+0.1 mM mercaptoethanol+1×, NEAA+100 ng/ml activin-A+20 ng/ml WNT3A under hypoxic conditions (approximately 3% $O_2$) at 37° C. in standard tissue culture incubator. Following two days post seeding, the media was switched to DMEM-F12+0.5% FBS+100 ng/ml activin-A+20 ng/ml WNT3A+ 100 nM GSK-3B inhibitor IX for four days under hypoxic conditions (approximately 3% $O_2$) at 37° C. in standard tissue culture incubator. FIG. 23 depicts the real-time PCR analysis of definitive endoderm markers at day 4 of differentiation. It appears that a seeding density of at least 10000-20000 cells/cm$^2$ is required for the robust formation of definitive endoderm.

Example 16

Telomere Length of EXPRES Cells

The telomere length of two EXPRES lines isolated according to Example 5 along with undifferentiated cells from the human embryonic stem cell line H1 was analyzed by using the Telo TAGGG Telomere Length Assay (Roche, Ind.) and following the manufacturer's instruction. FIG. 24 depicts the telomere length for EXPRES 01 cells at P24, EXPRES 02 cells at P17, H1 cells at P40, high and low telomere controls provided by the kit, along with the scale marker. Both lines appear to have shorter telomere length than undifferentiated ES cells.

Example 17

Further Differentiation of EXPRES Cells Cultured on Tissue Culture Substrate to Pancreatic Endoderm EXPRES 01 cells at passage 21 underwent a 5 day differentiation by treatment with 100 ng/ml activin-A, 10 ng/ml of Wnt3a, and 100 nM GSK3beta inhibitor IX in 0.5% FBS, DMEM:F12 media. Cells were analyzed by FACS and showed 80% of the cells were positive for CXCR4. The cells were then treated for 3 days in each of the following steps: 2% FBS DMEM:F12 containing 50 ng/ml FGF-10, and 0.25 μM KAAD-Cyclopamine (Calbiochem, CA); followed by, 1% B27 DMEM, low glucose containing 50 ng/ml FGF-10, 0.25 μM KAAD-Cyclopamine and 1 μM Retinoic Acid (Sigma, Mo.); followed by, 1% B27 DMEM, low glucose containing 1 μM DAPT (Calbiochem, CA) plus 50 ng/ml Exendin4 (Sigma, Mo.); and lastly followed by, 1% B27 DMEM CMRL containing 50 ng/ml each of IGF, HGF and Exendin4. Samples were taken at the end of each step, and RNA was extracted for the cells. Q-RT PCR was conducted for the markers shown. As depicted in FIG. 25, Insulin levels were increased 100 fold over untreated cells and PDX-1 levels were also increased over 1000 fold.

Example 18

Further Differentiation of EXPRES Cells Cultured on Tissue Culture Substrate to Foregut Endoderm EXPRES 01 cells at passage 35 underwent a 5 day differentiation by treatment with 10 ng/ml activin-A, 20 ng/ml of Wnt3a, and 100 nM GSK3beta inhibitor IX in 0.5% FBS, DMEM:F12 media. Cells were analyzed by FACS and showed approximately 70% of the cells were positive for CXCR4. The cells were then treated for in each of the following steps: 2% FBS DMEM:F12 containing 50 ng/ml FGF-10, and 0.25 μM KAAD-Cyclopamine (Calbiochem, CA) for 3 days; Step 3, 1% B27 DMEM, low glucose containing 50 ng/ml FGF-10, 0.25 μM KAAD-Cyclopamine and 1 μM Retinoic Acid (Sigma, Mo.) for 4 days; and Step 4, 1% B27 DMEM, low glucose containing 1 μM DAPT (Calbiochem, CA) plus 50 ng/ml Exendin4 (Sigma, Mo.) for 4 days. This protocol is based on a prior publication by D'Amour et al (Nature Biotech, 24, 1392, 2006). Cells were fixed at end of stage 4 and stained for PDX-1, HNF-3 beta, SOX-17, Albumin, anti-trypsin, and CDX-2. As depicted in FIG. 26, EXPRES cells can be readily differentiated to foregut endoderm as measured by expression of PDX-1 (approximately 20% of culture stained positive), HNF-3 beta (approximately 90% positive), albumin (approximately 5% positive), anti-1-Trypsin (approximately 70% positive), SOX-17 (approximately 70%), and CDX-2 (approximately 5% positive).

Example 19

Microarray Analysis of EXPRES Cells Versus Undifferentiated Human Embryonic Stem Cells Total RNA was isolated from cultures of the human embryonic stem cell line H9, at passage 44, EXPRES 01 P11 and EXPRES 02 P7 using an RNeasy mini kit (Qiagen): All groups contained three biological replicates and each biological replicate was repeated on two separate gene chips. Sample preparation, hybridization, and image analysis were performed according to the Affymetrix Human Genome U133 Plus 2.0 Array. Following normalization and a log transformation, data analysis was performed using OmniViz® software (MA) and GENESIFTER (VizXLabs, WA) Significant differences in gene expression between the samples were evaluated using analysis of variance and an F-test with adjusted P-value (Benjamini and Hochberg correction) of less than or equal to 0.05. Only genes with a present call in at least one group were included in the analysis. Table V lists the mean normalized log-transformed signal intensity of genes showing at least 5-fold difference between groups (undifferentiated ES, EXPRES 01 and EXPRES 02 cells) along with the adjusted P-value for each gene. Genes representing primitive streak or definite endoderm are highlighted in bold. Only the top 200 genes that are upregulated or down regulated are shown in Table V.

Example 20

Microarray Analysis of EXPRES Cells Differentiated to the DE Stage Versus Human Embryonic Stem Cells Differentiated to the DE Stage Total RNA was isolated from the following cultures using an RNeasy mini kit (Qiagen): A) H9P33 cells cultured on MATRIGEL-coated plates (1:30 dilution) and exposed to DMEM/F12 medium supplemented with 0.5% FBS and 100 ng/ml Activin-A and 20 ng/ml of wnt3A for two days followed by treatment with DMEM/F12 medium supplemented with 2% FBS and 100 ng/ml Activin-A (AA) for an additional three days; B) EXPRES 01 P24 cells cultured on TCPS and exposed to DMEM/F12 medium supplemented with 0.5% FBS, 100 ng/ml Activin-A, 20 ng/ml of WNT3A, and 100 nm GSK-3B IX inhibitor (Catalog# 361550, Calbiochem, CA) for five days C) EXPRES 02 P17 cells cultured on TCPS and exposed to DMEM/F12 medium supplemented with 0.5% FBS, 100 ng/ml Activin-A, 20 ng/ml of WNT3A, and 100 nm GSK-3B IX inhibitor (Catalog# 361550, Calbiochem, CA) for five days, D) H9P39 cells cultured on MATRIGEL-coated plates (1:30 dilution) and exposed to DMEM/F12 medium supplemented with 0.5% FBS and 100 ng/ml Activin-A and 20 ng/ml of wnt3A for two days followed by treatment with DMEM/F12 medium supplemented with 2% FBS and 100 ng/ml Activin-A (AA) for an additional two days RNA samples were collected from group D at 2 hrs, 6 hrs, 24 hrs, 30 hrs, 48 hrs, 72 hrs, and 96 hrs. EXPRES 01 and 02 cultured in their respective growth media were also included as controls. All groups contained three biological replicates and each biological replicate was repeated on two separate gene chips.

Sample preparation, hybridization, and image analysis were performed according to the Affymetrix Human Genome U133 Plus 2.0 Array. Following normalization and a log transformation, data analysis was performed using OmniViz® software (MA) and GENESIFTER (VizXLabs, WA) Significant differences in gene expression between the samples were evaluated using analysis of variance and an F-test with adjusted P-value (Benjamini and Hochberg correction) of less than or equal to 0.05. Only genes with a present call in at least one group were included in the analysis. Table VI lists the mean normalized log-transformed signal intensity of genes showing at least 5-fold between group A, group B, group C, and group D at various time points along with the adjusted P-value for each gene. Only the top 200 genes that are upregulated or down regulated are shown in Table VI. Genes representing primitive streak or definite endoderm are highlighted in bold. Table VII lists the correlation coefficient for each comparison group. Scatter plots corresponding to the correlation coefficients are depicted in FIG. 27. The global expression profile of EXPRES 01 cells appear to resemble the expression profile of samples at 30 hrs or less of the DE stage, whereas the EXPRES 02 cells appear to resemble the expression profile of samples at greater than 48 hrs of the DE stage.

Example 21

Formation of Embryoid Bodies and Differentiation to Various Lineages

EXPRES 01 passage 27 cultures were removed as single cells using TrypLE™ Express solution, spun at 200 g for 4 mins, and resuspended in DMEM-F12+20% FBS. The cell suspension was seeded on low adhesion Petri dishes. 3-4 days post seeding, embryoid body (EB) like structures were formed (FIG. 28). Treatment of the cultures with DMEM-F12+2% FBS+1 micro molar retinoic acid induced expression of ectoderm markers, such as NeuroD.

Example 22

Formation of Teratomas in the Kidney Capsules of NOD-SCID Mice

Undifferentiated cells from the human embryonic stem cell line H9 at passage 42, EXPRES 01 Passage 30, and EXPRES 02 P22 cells were released from cultures using TRYPLE, washed in basal media, and then suspended in DMEM-F12 basal media. Approximately $1\times10^6$ undifferentiated H9 P42, 1.5 million EXPRES 01 and 02 cells were injected into the kidney capsule of six week old NOD-SCID mice. Five weeks following transplantation, the animals were sacrificed; kidneys were excised and fixed in formalin or placed in lysis buffer to collect RNA for subsequent PCR analysis. FIG. 29 depicts expression of markers characteristic of mesoderm, ectoderm, endoderm, extraembryonic visceral endoderm, and pluripotency markers for collected samples. Similar to H9 line, both EXPRES lines show strong expression of all germ layers along with extra embryonic endoderm.

Example 23

Proliferation and Cell Cycle Analysis of EXPRES 03 Cells

Human embryonic stem cells have a unique cell cycle status that is distinguishable from other somatic cells, characterized by high proportion of cells in S-Phase, and shortened or truncated Gap phases (G1 and G2). The cell cycle control mechanisms in hES cells may be functionally linked to their self-renewal and pluripotency capacity of these cells, and may be different from control mechanism in their differentiated/committed counterparts. These experiments were designed to determine the cells cycle nature of EXPRES cells that have been shown to express many of the markers of pluripotency hES cells.

Methods: Cells were seeded at 5,000-10,000 cells/cm$^2$ in Cell Bind tissue culture flasks (Corning) and cultured for 2-4 days. EXPRES 03 cells were cultured either in growth medium containing 2% FBS in DMEM/F12 and Activin-A (100 ng/ml), wnt3a (10-20 ng/ml) and IGF (50 ng/ml). For comparative proliferation analysis, IGF was sometimes omitted from the growth factor cocktail. Cell proliferation was analyzed using the APC BRDU Flow kit according to the Manufacturer's recommendations (BD Biosciences, San Diego, Calif.). Briefly, cells were pulsed with BRDU for 1-2 hrs at the end of culture period, released using Tryple E Express and counted. Cells were fixed in BD Cytofix/Cytosperm Buffer, incubated for 30 min, followed by incubation with BD Cytoperm buffer for 10 minutes on ice. Cells were then treated with DNAse for 1 hr at 37° C. to expose incorporated BRDU, followed by staining with APC conjugated anti-BRDU antibody. For cell cycle analysis, cells were stained with 7AAD, and analyzed on FACS Array.

Results: Similar to the highly hES cells, EXPRES 03 cells retained a highly proliferation rate, as shown by the high percentage of cells that in S-phase determined by their capacity to incorporate BRDU in culture. The frequency of cells in S-Phase was typically greater than 45% (range 40-60%), similar to hES cells (FIG. 30 a-c). Although the number of EXPRES 03 cells grown in the presence of IGF were 2-3 times the number of cells grown in absence of IGF after 3-4 days, there was only marginal differences in frequency of cells in S-phase when cell were exposed to BRDU for 1 hour or more (FIG. 30 f). This high frequency of cell in S-phase and cell cycle structure is unlike that observed in somatic cells, as shown here for human amniotic fluid cells (AFDX002) (FIG. 30 d). Furthermore, mitomycin treated cells Mouse Embryo Fibroblast (MEF, FIG. 30 e) do not proceed into S-phase but show apparent accumulation in the G2/M phase (64%), which may be related to the inability of mitomycin treated cells to separate the DNA strands at mitosis.

Example 24

Transfection Efficiency of ES Cells Vs EXPRES Cells

A major limitation of genetic manipulation of hES is their relative resistance to conventional methods of transfection and viral transduction. In addition to their highly proliferative rates, EXPRES cells are easy to transfect in vitro. To compare transfection efficiency, in EXPRES and hES cells were transfected in culture with EGFP and analyzed by fluorescence microscopy and flow cytometric methods.

Methods: EXPRES 01 cells were seeded on human fibronectin coated (10 ug/ml) 6 well tissue culture plates in growth medium comprising 2% FBS in DMEM/F12, Activin-A (100 ng/ml), wnt3a (10-20 ng/ml) and IGF (50 ng/ml). For cell clusters hES cell were passaged by routine methods using collagenase into MATRIGEL coated 6 well culture plates, and grown in MEF conditioned hES medium. For single cells, hES cells were passaged by exposing cells to TRYPLE for 3 minutes at 37° C., followed by plating onto MATRIGEL coated 6 well culture plates. When cells achieved desired confluency (70-80%), cells were transfected with Lipofectamine 2000 according to the manufacturer's recommendations (Invitrogen, Carlsbad, Calif.). Briefly, 4 μg of DNA was diluted into 250 μl Opti-MEM I Reduced serum medium. Five microliters of Lipofectamine 200 was mixed into total of 250 μl Opti-MEM I medium for 5 minutes and gently mixed with diluted DNA. The DNA/Lipofectamine complexes were allowed to form at room temperature for 20 minutes, and then added to the respective wells with gentle swirling motions of the plates for gentle mixing. Cells were incubated in presence of complexes for another 24 hrs followed by complete change of medium. Cells were analyzed by fluorescence microscopy and flow cytometry 48 hrs following transfection.

Results: The uptake and expression of eGFP was compared by transfection of EXPRES 01 cells and hES cells plated as single cell dispersion or cell clusters, and analyzed 48 hrs later. EXPRES 01 cell showed the highest level of eGFP protein expression, with 75% of cell expressing eGFP by flow cytometric analysis (FIG. 31). In contrast, hES were more resistant to transfection, with only 3% of cell expressing eGFP protein by FACS when cell clusters were used. Preparing a single cell dispersion of hES enhanced the level of DNA uptake and eGFP expression to about 20%, but which is still by about three fold less the expression in EXPRES 01 cells.

Example 25

EXPRES Cells as a Versatile Tool for Screening

EXPRES cells were grown in DMEM:F12 medium containing 2% FBS, 100 ng/ml recombinant human Activin-A (R&D Systems), and 20 ng/ml recombinant mouse Wnt3a (R&D Systems). Growth medium for EXPRES 01 cells also contained 50 ng/ml recombinant human IGF-1 (R&D Systems). Both cell lines were routinely grown at 37° C. in an atmosphere of low oxygen (3%) and 5% $CO_2$. EXPRES 01 and EXPRES 02 cells were released from culture as a single cell suspension using TrypLE enzymatic digestion (Invitrogen, CA) then washed and counted to determine accurate cell numbers and viability (>95%). Aliquots ranging from 1,250 to 80,000 cells were distributed into human fibronectin-coated wells of a 96-well plate (Corning-Costar) in a final volume of 100 μl culture medium. Control wells were also fibronectin-coated and contained an equivalent volume of culture medium without cells. Plates were allowed to equilibrate overnight in a humidified chamber incubated under standard low oxygen, 5% $CO_2$ at 37° C. During this time, the cells attached as monolayer cultures with varying degrees of confluency dependent upon the initial seeding density. After overnight culture, 20 μl of MTS reagent (CellTiter 96 Aqueous Assay; Promega) was added to each well. MTS is reduced to formazan and can be used as a measure of dehydrogenase enzyme activity directly proportional to the number of live cells. One plate was returned to low oxygen culture while an identical parallel plate was incubated in normal oxygen (20%). After 4 hours, absorbance was read at 490 nm on a spectrophormetric plate reader (Molecular Devices). Statistical calculations for mean OD, standard deviation, and percent coefficient of variation (CV) were determined for replicate sample sets within each plate and then compared to similar wells between both plates.

Standard deviation and percent coefficient of variation values demonstrate that EXPRES cells can be evenly distributed between wells for high plating efficiency and good well-to-well reproducibility (Table VIII a-f). As seen with average $OD_{490}$ readings for equivalent numbers of cells, the EXPRES 01 line has a higher metabolic activity than the EXPRES 02 line. For each EXPRES line, percent CV values between the two plates suggest there are no differences in metabolic activity for parallel conditions regardless of atmospheric oxygen levels in this short-term assay. Optimal cell numbers per well within the linear range for this assay were determined by graphing average OD readings (FIG. 32): less than 20,000 cells/well for EXPRES 01 and less than 40,000 cells/well for EXPRES 02. Again, atmospheric differences in oxygen levels did not affect optimal cell number results in this short-term assay. These results suggest that EXPRES cells are amenable to screening protocols that can measure toxicological effects of various agents on cell proliferation and/or metabolic rate.

Example 26

Expansion of DE-Like Cells Derived from EXPRES Cells

Previous examples establish that EXPRES cells can be derived from embryonic stem cells and can be readily expanded on TCPS in various growth media. Most of these media formulation contain IGF as a supplement or insulin/IGF in 2% FBS used in the growth media. These factors have been shown to inhibit DE related genes through the PI-3 kinase pathway (Stem cells, 25:29-38, 2007). An alternative media was formulated based on DM-F12+0.5% FBS+100 ng/ml AA+20 ng/ml WNT3A+100 nM GSK-3B inhibitor IX (further referred to as "growth media for DE cells"). EXPRES 01 at passage 27 cells cultured in the above media were able to propagate at the same rate as cells cultured in DM-F12+2% FBS+100 ng/ml AA+20 ng/ml WNT3A+50 ng/ml IGF-I. Furthermore, cells cultured in the growth media for DE cells expressed strong DE markers by real-time PCR (FIG. 33) through three passages. Approximately 72% of cells expressed CXCR4 (FIG. 34).

Example 27 siRNA Knockdown of Target Genes in EXPRES Cells

Efficient knockdown of target genes in human embryonic stem cells using siRNA is severely limited by the ability to achieve high levels of transfection in human embryonic stem cells grown as cluster colonies. EXPRES cells are easily transfected with siRNA using conventional methods, and thus offer a valuable system to screen siRNA oligo sequences, as well as evaluate the role played by targeted genes.

Methods: EXPRES 03 cells were seeded on fibronectin coated (10 μg/ml) 6 well tissue culture plates in growth medium comprising 2% FBS in DMEM/F12, Activin-A (100 ng/ml), wnt3a (10-20 ng/ml) and IGF (50 ng/ml). For 6 well plates, 200,000 cells were seeded 24 hrs prior to transfection with the siRNA oligo sequences.

To evaluate target gene knockdown, cells at 70-80% confluency cells were transfected using Lipofectamine 2000 according to the manufacturer's recommendations (Ambion (Applied Biosystems), Foster City, Calif.). Briefly, the appropriate amount of siRNA was diluted into 250 μl Opti-MEM I Reduced serum medium to achieve a final concentration of 100 nmol. Five micrometers of Lipofectamine 2000 was diluted in 250 μl Opti-MEM I medium and incubated for 5 minutes. The complexes were incubated for 15-20 min at room temperature, and then added to the cells with gentle swirling motions of the plates for gentle mixing. Cells were incubated in presence of siRNA for another 24 hrs followed by complete change of medium. Cells were visualized with fluorescence microscopy 24-48 hrs following transfection, and RNA harvested for analysis of target gene knockdown by quantitative RT-PCR methods. The following pre-validated siRNA oligo sequences, purchased from Ambion were tested: Beta-catenin (Id. No. 42816) and GSK3b (Id. No. 42839).

Results: Fluorescence microscopy revealed a very high level of siRNA uptake by EXPRES cells (>80%) when using fluorescently labeled siRNA (FIG. 35). RNA harvested from the cells was analyzed by PCR for target gene knockdown, and compared with control siRNA oligo transfected cells. Beta-catenin and GSK3b siRNA oligos achieved very high levels of gene knockdown in EXPRES cells, with greater than 93% gene knockdown. Other non-validated oligo sequences to other gene targets eg Hes-1, Oct-4 achieved lower and variable levels of target gene knockdown. Specificity of oligo sequences was verified by analysis of other gene transcripts, which did not show any appreciable knockdown.

Example 28

Cytokine Antibody Array Analysis for EXPRES 01 and 02 Lines

EXPRES 01 and 02 lines at passage 22 and 23, respectively, were grown to approximately 70% confluency in their respective media and then cell lysates was collected using mammalian cell lysis kit (Sigma-Aldrich, MO). Cytokine array analysis was completed using Cytokine Array panels provided by RayBiotech, GA (http://www.raybiotech.com/). Table IX a-c lists cytokine, cytokine and growth factor receptor expression following normalization of the data and background subtraction. For each panel, positive and negative controls are also included. The panels were run for two different samples per cell type.

Example 29

Karyotype Analysis

The karyotype of EXPRES 01 cells at passage 20 and EXPRES 02 cells at passage 15 was determined by G-band analysis. Cytogenetic analysis was performed on twenty-one G-banded cells from EXPRES 01 and on twenty G-banded cells from EXPRES 02. Half of the G-banded EXPRES 01 cells showed a normal 46XX karyotype while the rest showed abnormal karyotype such as trisomy 17. The EXPRES 02 line also showed a chromosome rearrangement with a duplication of almost all of the chromosome 1 short-arm.

Example 30

Derivation of EXPRES Cells from a Suspension of Single Human Embryonic Stem Cells in the Presence of a Rho-Kinase (ROCK) Inhibitor Cells from the human embryonic stem cell line H9 at passage 35 lines were cultured under hypoxic conditions (approximately 3% $O_2$) for at least three passages. The cells were cultured in MEF-CM supplemented with 8 ng/ml of bFGF and plated on MATRIGEL coated plates according to Example 1. At approximately 60% confluency, the cultures were exposed to TrypLE™ Express solution (Invitrogen, CA) for 5 mins Released cells were resuspended in DM-F12+2% FBS medium, recovered by centrifugation, and counted using a hemocytometer. The released cells were seeded at 1000-10,000 cells/$cm^2$ on tissue culture polystyrene (TCPS) flasks and cultured in DM-F12+2% FBS+100 ng/ml activin-A+20 ng/ml WNT-3A+50 ng/ml of IGF-I+0.1 mM mercaptoethanol (Invitrogen, CA), non-essential amino acids (1×, NEAA from Invitrogen, CA)+/−10 μm ROCK inhibitor (Y-27632, Calbiochem, CA) under hypoxic conditions (approximately 3% $O_2$) at 37° C. in a standard tissue culture incubator. The TCPS flaks were not coated with MATRIGEL or other extracellular matrix proteins. The media was changed daily. The first passage cells are referred to as P1. As shown in FIG. 37, 24 hrs after seeding, addition of the ROCK inhibitor resulted in a significantly larger number of attached cells as compared to cultures derived in the absence of the ROCK inhibitor. EXPRES cells derived using the ROCK inhibitor, Y27632 were designated as EXPRES 15.

Example 31

Karyotype Analysis

The karyotype of EXPRES 15 cells at passage 5 and 12 were determined by G-band analysis. Cytogenetic analysis was performed on twenty-one G-banded cells from EXPRES 15 all of the cells showed a normal 46XX karyotype (FIG. 38). FISH analysis of chromosomes 12 and 17 also showed that all cells demonstrated a normal signal pattern for the ETV6 BAP (TEL) gene located on chromosome 12 and all cells demonstrated a normal signal pattern for the Her2/neu gene and 17 centromere on chromosome 17.

Example 32

EXPRES Cells can be Maintained in Media Containing a Range of Concentrations of IGF, WNT3A, Activin-A, and GSK-3B Inhibitors EXPRES 11 cells were grown in DMEM/F12 (Invitrogen) containing 2% FBS, 100 ng/ml activin-A, 20 ng/ml Wnt3a and 50 ng/ml IGF. At 80% confluency, cells were passed using TrypLE Express (Invitrogen) into 96-well plates at a density of 4000 cells/well in DMEMF12 containing 2% FBS. Cells were allowed to adhere to the substrate for 1 hour in a humidified incubator held at 37° C. with 5% CO2, prior to the addition of activin-A ranging from 50 to 100 ng/ml, Wnt3a ranging from 10 to 20 ng/ml, IGF ranging from 10 to 50 ng/ml, and 50 to 100 nM GSK-3B inhibitor (IX). At 24, 48 and 96 hours, cell viability was determined using the CellTiter® 96 AQueous One Solution Cell Proliferation Assay (Promega). Briefly, MTS reagent was added to the 96-well plates and allowed to incubate with the cells for 1-4 hours and then reading the absorbance at 490 nm on a plate reader. The absorbance reading was directly proportional to the number of living cells. FIG. 39 a-c shows the absorbance readings at a) 24 hrs, b) 48 hrs, and c) 96 hrs post seeding.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

Lengthy table referenced here

[US07939322-20110510-T00001]
*USRE043876-20121225-T00001*

Please refer to the end of the specification for access instructions.

Lengthy table referenced here

[US07939322-20110510-T00002]
*USRE043876-20121225-T00002*

Please refer to the end of the specification for access instructions.

Lengthy table referenced here

[US07939322-20110510-T00003]
*USRE043876-20121225-T00003*

Please refer to the end of the specification for access instructions.

Lengthy table referenced here

[US07939322-20110510-T00004]
*USRE043876-20121225-T00004*

Please refer to the end of the specification for access instructions.

Lengthy table referenced here

[US07939322-20110510-T00005]
*USRE043876-20121225-T00005*

Please refer to the end of the specification for access instructions.

Lengthy table referenced here

[US07939322-20110510-T00006]
*USRE043876-20121225-T00006*

Please refer to the end of the specification for access instructions.

Lengthy table referenced here

[US07939322-20110510-T00007]
*USRE043876-20121225-T00007*

Please refer to the end of the specification for access instructions.

Lengthy table referenced here

[US07939322-20110510-T00008]
*USRE043876-20121225-T00008*

Please refer to the end of the specification for access instructions.

Lengthy table referenced here

[US07939322-20110510-T00010]
*USRE043876-20121225-T00010*

Please refer to the end of the specification for access instructions.

Lengthy table referenced here

[US07939322-20110510-T00009]
*USRE043876-20121225-T00009*

Please refer to the end of the specification for access instructions.

Lengthy table referenced here

[US07939322-20110510-T000011]
*USRE043876-20121225-T00011*

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=[US07939322B1]*USRE043876E1*). An electronic copy of the table will also be available from the USPTO upon request and payment of the fee set forth in 37 CFR 1.19(b)(3).

SEQUENCE LISTING

```
<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: SYNTHETIC CONSTRUCT

<400> SEQUENCE: 1

tggcgcagca gatacca                                                  17


<210> SEQ ID NO 2
<211> LENGTH: 18
<212> TYPE: DNA
<213> ORGANISM: Artificial Sequence
<220> FEATURE:
<223> OTHER INFORMATION: SYNTHETIC CONSTRUCT

<400> SEQUENCE: 2

agcgccttcc acgacttg                                                 18


<210> SEQ ID NO 3
<211> LENGTH: 23
<212> TYPE: DNA
<213> ORGANISM: Artificial Sequence
<220> FEATURE:
<223> OTHER INFORMATION: SYNTHETIC CONSTRUCT

<400> SEQUENCE: 3

ccagcatctt gctcaactcg gcg                                           23
```

What is claimed is:

1. A method for deriving a population of cells expressing pluripotency markers and expressing markers characteristic of the definitive endoderm lineage comprising the steps of:

a. [Obtaining] *obtaining* a population of cells expressing markers HNF-3β, GATA-4, Mixl1, CXCR4 and SOX-17, characteristic of the definitive endoderm lineage, and b. [Culturing] *culturing* the population of cells under hypoxic conditions, on a tissue culture substrate that is not pre-treated with a protein or an extracellular matrix in a medium supplemented with Activin A and [wnt-3A] *a wnt ligand*, and IGF-1 or insulin, transferrin and selenium, wherein the cultured cells express the markers of the definitive endoderm lineage and pluripotency markers.

2. The method of claim 1, wherein the population of cells expressing markers characteristic of the definitive endoderm lineage are cultured in normoxic conditions prior to culturing the cells under hypoxic conditions, on a tissue culture substrate that is not pre-treated with a protein or an extracellular matrix.

3. The method of claim 1, wherein the population of cells expressing markers characteristic of the definitive endoderm lineage are cultured in hypoxic conditions prior to culturing the cells under hypoxic conditions, on a tissue culture substrate that is not pre-treated with a protein or an extracellular matrix.

4. The method of claim 1, wherein the hypoxic conditions are an $O_2$ level from about 1% to about 20%.

5. The method of claim 1, wherein the hypoxic conditions are an $O_2$ level from about 2% to about 10%.

6. The method of claim 1, wherein the hypoxic conditions are an $O_2$ level of about 3%.

7. The method of claim 1, wherein the cells are cultured under hypoxic conditions, on a tissue culture substrate that is not pre-treated with a protein or an extracellular matrix, in medium containing serum at a concentration from about 2% to about 5%.

8. The method of claim 1, wherein the cells are cultured under hypoxic conditions, on a tissue culture substrate that is not pre-treated with a protein or an extracellular matrix, in medium containing serum at a concentration of about 2%.

9. The method of claim 1, wherein the population of cells expressing markers characteristic of the definitive endoderm lineage are cultured under hypoxic conditions, on a tissue culture substrate that is not pre-treated with a protein or an extracellular matrix, in medium containing IGF-1 at a concentration from about 25 ng/ml to about 50 ng/ml.

10. The method of claim 1, wherein the population of cells expressing markers characteristic of the definitive endoderm lineage are cultured under hypoxic conditions, on a tissue culture substrate that is not pre-treated with a protein or an extracellular matrix, in medium containing IGF-1 at a concentration of about 50 ng/ml.

11. The method of claim 1, wherein the population of cells expressing pluripotency markers express at least one of the pluripotency markers selected from the group consisting of ABCG2, cripto, FoxD3, Connexin43, Connexin45, Oct4, SOX-2, Nanog, hTERT, UTF-1, ZFP42, SSEA-3, SSEA-4, Tral-60, and Tral-81.

12. The method of claim 1, wherein the cells are cultured under hypoxic conditions, on a tissue culture substrate that is not pre-treated with a protein or an extracellular matrix, in medium containing Activin-A at a concentration from about 50 ng/ml to about 100 ng/ml.

13. The method of claim 1, wherein the cells are cultured under hypoxic conditions, on a tissue culture substrate that is not pre-treated with a protein or an extracellular matrix, in medium containing Activin-A at a concentration of about 100 ng/ml.

14. The method of claim 1, wherein the cells are cultured under hypoxic conditions, on a tissue culture substrate that is not pre-treated with a protein or an extracellular matrix, in medium containing a Wnt ligand at a concentration from about 10 ng/ml to about 20 ng/ml.

15. The method of claim 1, wherein the cells are cultured under hypoxic conditions, on a tissue culture substrate that is not pre-treated with a protein or an extracellular matrix, in medium containing a Wnt ligand at a concentration of about 200 ng/ml.

16. The method of claim 1, wherein the Wnt ligand is Wnt-3a.

* * * * *